(12) United States Patent
Kleckner et al.

(10) Patent No.: US 9,101,772 B2
(45) Date of Patent: Aug. 11, 2015

(54) SECURE AND EFFICACIOUS THERAPY DELIVERY FOR A PACING ENGINE

(75) Inventors: Karen J. Kleckner, New Brighton, MN (US); Kathleen A. Prieve, Shoreview, MN (US); Jeffrey M. Gillberg, Coon Rapids, MN (US); Ren Zhou, Blaine, MN (US); Kenneth M. Anderson, Bloomington, MN (US); D. Curtis Deno, Andover, MN (US); Glenn C. Zillmer, Hudson, WI (US); Ruth N. Klepfer, St. Louis Park, MN (US); Vincent E. Splett, Apple Valley, MN (US); David E. Euler, Plymouth, MN (US); Lawrence J. Mulligan, Andover, MN (US); Edwin G. Duffin, North Oaks, MN (US); David A. Igel, Lino Lakes, MN (US); John E. Burnes, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 704 days.

(21) Appl. No.: 12/633,893

(22) Filed: Dec. 9, 2009

(65) Prior Publication Data

US 2010/0152804 A1    Jun. 17, 2010

Related U.S. Application Data

(63) Continuation of application No. 11/765,260, filed on Jun. 19, 2007, now abandoned, which is a continuation-in-part of application No. 10/703,956, filed on Nov. 7, 2003, now Pat. No. 7,233,824.

(60) Provisional application No. 60/509,335, filed on Oct. 7, 2003.

(51) Int. Cl.
*A61N 1/365*    (2006.01)
*A61N 1/368*    (2006.01)
(Continued)

(52) U.S. Cl.
CPC .......... *A61N 1/3627* (2013.01); *A61N 1/36114* (2013.01); *A61N 1/36585* (2013.01);
(Continued)

(58) Field of Classification Search
CPC ............ A61N 1/36114; A61N 1/3427; A61N 1/36585; A61N 1/36521
USPC ...................................... 607/9, 11, 14, 15, 17
See application file for complete search history.

(56) References Cited

U.S. PATENT DOCUMENTS

| 4,674,518 A | 6/1987 | Salo |
| 5,117,824 A | 6/1992 | Kiemel et al. |

(Continued)

FOREIGN PATENT DOCUMENTS

| EP | 0494487 | 7/1992 |
| WO | 9725098 A1 | 7/1997 |

(Continued)

OTHER PUBLICATIONS

Hirotsugu Yamada, David O. Martin, Kent A. Mowrey, Neil L. Greenberg and Don W. Wallick. "Effects of coupled pacing on cardiac performance during acute atrial tachycardia and fibrillation: an old therapy revisited for a new reason," Am J Physiol Heart Circ Physiol 285:H2630-H2638, 2003. First published Jul. 31, 2003.*

*Primary Examiner* — Tammie K Heller
(74) *Attorney, Agent, or Firm* — Carol F. Barry

(57) ABSTRACT

A method of stimulation therapy and an apparatus for providing the therapy which addresses cardiac dysfunction including heart failure. The therapy employs atrial pacing pulses delivered to a heart after the atrial refractory period and timed so that they will not cause a ventricular contraction. These atrial pacing are timed to achieve beneficial effects on myocardial mechanics (efficacy) while maintaining an extremely low level of risk of arrhythmia induction. These methods may be employed individually or in combinations in an external or implantable ESS therapy delivery device.

20 Claims, 37 Drawing Sheets

(51) Int. Cl.
*A61N 1/362* (2006.01)
*A61N 1/36* (2006.01)
*A61N 1/39* (2006.01)

(52) U.S. Cl.
CPC ........... *A61N1/3684* (2013.01); *A61N 1/36521* (2013.01); *A61N 1/36564* (2013.01); *A61N 1/36578* (2013.01); *A61N 1/3962* (2013.01)

(56) References Cited

U.S. PATENT DOCUMENTS

| | | | |
|---|---|---|---|
| 5,158,078 A | 10/1992 | Bennett et al. | |
| 5,213,098 A | 5/1993 | Bennett et al. | |
| 5,224,475 A | 7/1993 | Berg et al. | |
| 5,226,513 A | 7/1993 | Shibayama | |
| 5,314,448 A | 5/1994 | Kroll et al. | |
| 5,318,593 A | 6/1994 | Duggan | |
| 5,331,966 A | 7/1994 | Bennett et al. | |
| 5,366,485 A | 11/1994 | Kroll et al. | |
| 5,417,717 A | 5/1995 | Salo et al. | |
| 5,564,434 A | 10/1996 | Halperin et al. | |
| 5,626,623 A | 5/1997 | Kieval et al. | |
| 5,713,924 A | 2/1998 | Min et al. | |
| 5,800,464 A | 9/1998 | Kieval | |
| 5,835,975 A | 11/1998 | Peeters et al. | |
| 6,104,949 A | 8/2000 | Pitts Crick et al. | |
| 6,438,408 B1 | 8/2002 | Mulligan et al. | |
| 7,233,824 B2 | 6/2007 | Kleckner et al. | |
| 7,245,967 B1 | 7/2007 | Shelchuk | |
| 7,292,888 B2 | 11/2007 | Deno et al. | |
| 2002/0147468 A1 | 10/2002 | Kim et al. | |
| 2003/0032986 A1 | 2/2003 | Kupper | |
| 2004/0049235 A1* | 3/2004 | Deno et al. | 607/9 |
| 2005/0090872 A1 | 4/2005 | Deno et al. | |
| 2007/0250124 A1 | 10/2007 | Burnes et al. | |

FOREIGN PATENT DOCUMENTS

| | | |
|---|---|---|
| WO | 9802209 A2 | 1/1998 |
| WO | 0158518 A2 | 8/2001 |
| WO | 02053026 A2 | 7/2002 |
| WO | 03020364 A2 | 3/2003 |

* cited by examiner

SECURE AND EFFICACIOUS THERAPY DELIVERY FOR A PACING ENGINE

CROSS-REFERENCE TO RELATED APPLICATIONS

This patent disclosure is a continuation of Ser. No. 11/765,260, filed Jun. 19, 2007, now abandoned, which is a continuation-in-part of non-provisional U.S. patent application Ser. No. 10/703,956 entitled, "SECURE AND EFFICACIOUS THERAPY DELIVERY FOR AN EXTRA-SYSTOLIC STIMULATION PACING ENGINE," filed Nov. 7, 2003, and issued 19 Jun. 2007 as U.S. Pat. No. 7,233,824, which also claims the benefit of U.S. Provisional Application No. 60/509,335, filed on Oct. 7, 2003. The disclosure of the above application is incorporated herein by reference.

FIELD OF THE INVENTION

The present invention relates generally to implantable medical devices and more specifically to providing appropriate therapies for acute or chronic cardiac mechanical dysfunction such as heart failure (HF), cardiogenic shock, pulseless electrical activity (PEA), or electromechanical dissociation (EMD).

BACKGROUND OF THE INVENTION

Patients suffering from chronic HF manifest an elevation of left ventricular end-diastolic pressure and frequently volume, according to the well-known heterometric autoregulation principles espoused by Frank and Starling. This may also occur while left ventricular end-diastolic volume remains normal due to a decrease in left ventricular compliance concomitant with increased ventricular wall stiffness. HF due to chronic hypertension, ischemia, infarct or idiopathic cardiomyopathy is associated with compromised systolic and diastolic function involving decreased atrial and ventricular muscle compliance. These may be conditions associated with chronic disease processes or complications from cardiac surgery with or without specific disease processes. Most heart failure patients do not normally suffer from a defect in the conduction system leading to ventricular bradycardia, but rather suffer from symptoms which may include a general weakening of the contractile function of the cardiac muscle, attendant enlargement thereof, impaired myocardial relaxation and depressed ventricular filling characteristics in the diastolic phase following contraction. Pulmonary edema, shortness of breath, and disruption in systemic blood pressure are associated with acute exacerbations of heart failure. All these disease processes lead to insufficient cardiac output to sustain mild or moderate levels of exercise and proper function of other body organs, and progressive worsening eventually results in cardiogenic shock, arrhythmias, electromechanical dissociation, and death.

Such patients are normally treated with drug therapies, including digitalis, which may lead to toxicity or lose effectiveness over time. Many inotropic drugs have recently become available, targeted at various receptors in the myocyte and designed for the purpose of directly stimulating cardiac tissue in order to increase contractility. However, there exist many possible undesirable side effects, in addition to the fact that these drugs do not always work for their intended purpose. This is especially characteristic of the patient suffering from end-stage heart failure.

Since dual chamber pacing was developed, conventional, atrioventricular (AV) synchronous pacing systems, including DDD and DDDR pacing systems, marketed by Medtronic, Inc. and other companies, have also been prescribed for treatment of HF as well as a variety of bradycardia conditions. Certain patient groups suffering heart failure symptoms with or without bradycardia tend to do much better hemodynamically with AV synchronous pacing due to the added contribution of atrial contraction to ventricular filling and subsequent contraction. However, fixed or physiologic sensor driven rate responsive pacing in such patients does not always lead to improvement in cardiac output and alleviation of the symptoms attendant to such disease processes because it is difficult to assess the degree of compromise of cardiac output caused by HF and to determine the pacing parameters that are optimal for maximizing cardiac output. Selection of an optimal AV delay often requires obtaining pressure data involving an extensive patient work-up as set forth in commonly assigned U.S. Pat. No. 5,626,623.

A series of PCT publications including, for example, PCT WO 97/25098 describe the application of one or more "non-excitatory" anodal or cathodal stimulation pulses to the heart and maintain that improvements in LV performance may be realized without capturing the heart. In a further commonly assigned U.S. Pat. No. 5,800,464, the contents of which are hereby incorporated by reference herein, sub-threshold anodal stimulation is provided to the heart to condition the heart to mechanically respond more vigorously to the conventional cathodal supra-threshold pacing pulses.

Thus, various stimulation regimens have been proposed for the treatment of cardiac dysfunction including HF which involve application of supra-threshold and/or sub-threshold stimulation paired or coupled pacing pulses or pulse trains. Moreover, various electrodes have been proposed for single site and multi-site delivery of the stimulation pulses to one or more heart chambers in the above-referenced patents and publications. However, it remains difficult to economically determine appropriate candidates that would benefit from such stimulation and to measure the efficacy of a given stimulation regimen and/or electrode array. Extensive catheterization procedures must be conducted of a heart failure patient to determine if he or she is a candidate for implantation of such a system. Then, the efficacy of any given treatment must be assessed at implantation and in periodic post-implant follow-up clinical tests. The patient work-up and follow-up testing must take into account or simulate known patient activities, patient posture, and whether the patient is awake or asleep in order to be representative of the heart failure condition over a daily time span. Furthermore, these therapies are susceptible to losing efficacy or causing arrhythmias with shifts in stimulation timing or the physiologic response to stimulation.

Physiologic and device operating data gathering capabilities have been included in modern implantable cardiac pacemakers and implantable cardioverter/defibrillators (ICDs) in order to provide a record of bradycardia or tachyarrhythmia episodes and the response to same provided by the pacemaker or ICD. The stored physiologic device operations and patient data as well as real-time electrogram (EGM) data can be uplink telemetered to an external programmer for display and analysis by medical heath care providers, as is well known in the art.

In addition, implantable cardiac monitors have been clinically used or proposed for use for monitoring hemodynamic and electrical signals of a patient's heart that do not presently include any stimulation capabilities, e.g., cardiac pacing or cardioversion/defibrillation. Such implantable monitors are implanted in patients to develop data over a longer time period than in the clinical setting that can be retrieved in the same manner and used to diagnose a cardiac dysfunction, including HF, that manifests itself sporadically or under certain loads and stresses of daily living.

One such implantable EGM monitor for recording the cardiac electrogram from electrodes remote from the heart as disclosed in commonly assigned U.S. Pat. No. 5,331,966 and PCT publication WO 98/02209 is embodied in the Medtronic® REVEAL® Insertable Loop Recorder having spaced housing EGM electrodes. More elaborate implantable hemodynamic monitors (IHMs) for recording the EGM from electrodes placed in or about the heart and other physiologic sensor derived signals, e.g., one or more of blood pressure, blood gases, temperature, electrical impedance of the heart and/or chest, and patient activity have also been proposed. The Medtronic® CHRONICLE® IHM is an example of such a monitor that is coupled through a lead of the type described in commonly assigned U.S. Pat. No. 5,564,434 having capacitive blood pressure and temperature sensors as well as EGM sense electrodes. Such implantable monitors when implanted in patients suffering from cardiac arrhythmias or heart failure accumulate date and time stamped data that can be of use in determining the condition of the heart over an extended period of time and while the patient is engaged in daily activities.

A HF monitor/stimulator is disclosed in commonly assigned U.S. Pat. No. 6,104,949 that senses the trans-thoracic impedance as well as patient posture and provides a record of same to diagnose and assess the degree and progression of HF. The sensed trans-thoracic impedance is dependent on the blood or fluid content of the lungs and assists in the detection and quantification of pulmonary edema symptomatic of HF. Trans-thoracic impedance is affected by posture, i.e. whether the subject is lying down or standing up, and the sensed trans-thoracic impedance is correlated to the output of the patient posture detector to make a determination of presence of and the degree of pulmonary edema for therapy delivery and/or physiologic data storage decisions.

A monitor/stimulator is disclosed in U.S. Pat. No. 5,417,717, that monitors and assesses the level of cardiac function then permits a physician to arbitrate the therapy mode, if therapy is indicated. The monitor/stimulator assesses impedance, EGM, and/or pressure measurements, and then calculates various cardiac parameters. The results of these calculations determine the mode of therapy to be chosen. Therapy may be administered by the device itself or a control signal may be telemetered to various peripheral devices aimed at enhancing the heart's function. Alternatively, the device may be programmed to monitor and either store or telemeter information without delivering therapy.

Particularly, the implantable monitor/stimulator monitors conventional parameters of cardiac function and contractile state, including all phases of the cardiac cycle. Thus, assessments of contractile state measured include indices of both cardiac relaxation and contraction. Utilizing the dual source ventricular impedance plethysmography technique described in U.S. Pat. No. 4,674,518, the monitor/stimulator monitors cardiac function by assessing hemodynamic changes in ventricular filling and ejection or by calculating isovolumic phase indices by known algorithms. The primary calculations involve: (1) the time rate of change in pressure or volume, dP/dt or dV/dt, as isovolumic indicators of contractility; (2) ejection fraction as an ejection phase index of cardiac function according to the known quotient of stroke volume divided by end diastolic volume; (3) Maximal elastance, $E_M$; (4) regression slope through maximal pressure-volume points as a further ejection phase index of contractility using the method of Sagawa; (5) stroke work according to the known pressure-volume integration; (6) the time course of minimum (end) diastolic pressure-volume measurements according to the method of Glantz as a measure of diastolic function; and (7) cardiac output calculation according to the known product of heart rate and stroke volume as an index of level of global function.

While measurement and storage of this group of parameters of cardiac function and contractile state can provide valuable information about the state of heart failure, there are other parameters that of even greater value. Momentary changes to a patient's autonomic state can change blood pressure (P), heart rate, and pressure rate of change (dP/dt) contractility measures and not be reflective of a "true" functional state change of the heart. Such momentary changes in autonomic state are caused by excitement and postural changes as noted in the above-referenced '949 patent and other movements, such as bending down to pick up an object or suddenly standing up from a sitting or reclining position. It would be desirable to obtain cardiac data that provides an enhanced assessment of cardiac contractile dysfunction state (rather than a measure of pulmonary edema as in the '949 patent) that are less sensitive to such patient mental states, movements and posture changes by enhanced signal processing of relatively simple to measure cardiac signals and states.

Preferably, the parameter data is associated with a date and time stamp and with other patient data, e.g., patient activity level, and the associated parameter data is stored in implantable medical device (IMD) memory for retrieval at a later date employing conventional telemetry systems. Incremental changes in the parameter data over time, taking any associated time of day and patient data into account, provide a measure of the degree of change in the condition of the heart.

BACKGROUND OF THE INVENTION

Millions of patients in the U.S. have been diagnosed with heart failure. Heart failure (HF) is not a specific disease, but rather a compilation of signs and symptoms, all of which are caused by an inability of the heart to appropriately increase cardiac output during exertion. HF may be caused by chronic hypertension, ischemia, tachyarrhythmias, infarct or idiopathic cardiomyopathy. The cardiac diseases associated with symptoms of congestive failure include dilated cardiomyopathy, restrictive/constrictive cardiomyopathy, and hypertrophic cardiomyopathy. The classical symptoms of the disease include shortness of breath, edema, and overwhelming fatigue. As the disease progresses, the lack of cardiac output may contribute to the failure of other body organs, leading to cardiogenic shock, arrhythmias, electromechanical dissociation, and death.

Delivering pacing during the refractory period is a type of non-excitatory stimulation (NES) that causes the release of catecholamines such as norepinephrine within the tissue of the heart. This chemical release results in an increased contractility of the cardiac tissue, which in turn, results in increased cardiac output, fewer symptoms of heart failure and improved exertional capacity.

The treatment of severe cardiac dysfunction and decompensated heart failure may include inotropic drug therapies such as the catecholamines dopamine and dobutamine or phosphodiesterase inhibitors milrinone or aminone. Although these agents may be beneficial in specific settings, they require administration of a drug, often by intravenous route, with systemic side effects and the time-consuming involvement of skilled clinicians. Electrical stimulation therapies are attractive alternatives because they may be administered by implanted or external devices very shortly after dysfunction appears or worsens and because their actions may be confined to the heart.

Delivering stimulation during the refractory period is a type of non-excitatory stimulation (NES) also denoted herein as refractory period stimulation (RPS) causes release of catecholamines such as norepinephrine within the tissue of the heart. This chemical release (modulated or regulated as described herein) results from selective electrical stimulation of innervated portions of the myocardial substrate. Because the electrical stimulation is delivered during the non-excitatory or refractory period wherein the discrete myocytes cannot contract, only the interstitial nerve fibers effectively receive stimulation. This results in increased contractility of the cardiac tissue which, in turn, results in increased pressure or flow, fewer symptoms of heart failure, and improved exertional capacity. NES neurostimulation employs one or more pulses applied shortly after a sensed depolarization or an initial pacing pulse is delivered and a resulting ventricular contraction occurs. These NES pulses are delivered during the refractory period of the cardiac tissue such that they do not result in another mechanical contraction or electrical depolarization.

Another type of electrical stimulation can be provided during the nonrefractory period of the cardiac cycle. This type of stimulation results in an additional electrical depolarization and, when appropriately timed, results in post extrasystolic potentiation (RPS). The additional depolarization, coming shortly after a first depolarization, is likely not associated with a sizable mechanical contraction. The contractility of subsequent cardiac cycles is increased as described in detail in commonly assigned U.S. Pat. No. 5,213,098. The mechanism is understood to depend on calcium cycling within the myocytes. The early extrasystole tries to initiate calcium release from the sarcoplasmic reticulum (SR) too early and as a result does not release much calcium. However, the SR continues to take up further calcium with the result that the subsequent cardiac cycle causes a large release of calcium from the SR and the myocyte contracts more vigorously. Excitatory RPS stimulation requires an extra electrical depolarization that is accompanied by a small mechanical contraction.

Another known treatment for HF patients involves using atrioventricular (AV) synchronous pacing systems, including DDD and DDDR pacing devices, cardiac resynchronization therapy (CRT) devices, and defibrillation systems, to treat certain patient groups suffering heart failure symptoms. These systems generally pace or sense in both the right atrium and right ventricle to synchronize contractions and contribute to ventricular filling. Cardiac resynchronization devices extend dual chamber pacing to biventricular pacing to achieve better filling and a more coordinated contraction of the left and right ventricles. These pacing therapies result in greater pulse pressure, increased dP/dt, and improved cardiac output. However, determining the appropriate pacing parameters is difficult. For example, optimizing the length of the AV delay requires obtaining pressure data involving an extensive patient work-up as set forth in commonly assigned U.S. Pat. No. 5,626,623. These pacing systems may also include atrial and ventricular defibrillators or other therapies for tachyarrhythmias. As a direct result of a tachycardia or as a sequela, cardiac function may deteriorate to the point of greatly reduced cardiac output and elevated diastolic pressure. Rapid termination of tachycardias prevents worsening of heart failure.

The above-described therapies, including pacing, CRT, NES, and defibrillation capability, may be used alone or in combination to treat cardiac dysfunction including HF. However, prior art systems have not achieved a comprehensive therapy regimen that coordinates these mechanisms in a manner that is both safe and effective. Delivery of electrical stimulation as the heart tissue is becoming non-refractory can trigger a tachyarrhythmia. This is particularly true if multiple high-amplitude pacing pulses are utilized. A second problem may be a shift in the magnitude of resulting potentiation or refractory interval due to the course of disease or medication. These may lead to unacceptable levels of potentiation performance, or loss of effect altogether. Therefore, readily obtaining the appropriate timing parameters associated with this type of therapy is essential.

What is needed is a system and method that combines the known therapies available for treating cardiac dysfunction including HF in a manner that optimizes mechanical function or cardiac output, while also minimizing any risks associated with possibly inducing an arrhythmia.

As discussed herein and in the related, incorporated-by-reference applications, an RSP therapy involves providing one or more pulses (e.g., one to a plurality of electrical pulses having programmable values, such as for instance 50 Hz pulse(s) with a pulse amplitude of 4-10 volts, nominal pulse width of 1 to 3 ms) during the refractory period of at least one ventricle. The pulses are delivered such that the ventricles do not experience a second depolarization following delivery of the pulse(s). The RPS therapy increases contractile function and stroke volume on subsequent contractions. The magnitude of the enhanced function is dependent on simulation timing, location, waveform characteristics, duration and frequency of RPS therapy delivery and the like. The delivery location can include multi-site locations within one or both ventricles (or via a coronary vein, a pericardial location, and/or single ventricular sites. The pulse or pulses can be bi-polar or uni-polar and the vectors of said pulse(s) can vary between any available electrodes.

SUMMARY OF THE INVENTION

The current invention provides a system and method for delivering therapy for cardiac hemodynamic dysfunction, which without limitation, may include one of the following features:

Therapy for cardiac dysfunction that might otherwise require inotropic drugs such as dobutamine, calcium, or milrinone;

Therapy for cardiac dysfunction that might otherwise require mechanical aids such as intra-aortic balloon pumps, cardiac compression devices, or LV assist device pumps;

An implantable or external device that continuously monitors the patient, automatically administering therapy when physiologic sensors indicate need or the patient experiences symptoms;

Treatment for cardiac dysfunction as a result of drug overdose or hypothermia;

Combined with negative inotrope drug treatments such as beta blockers to improve patient tolerance of these treatments;

Therapy for post ischemic cardiac dysfunction or stunning such as following coronary vessel occlusion, thrombolytic drugs, angioplasty, or cardiac bypass surgery;

Support for the dysfunction that is associated with coming off cardiac bypass and the use of cardioplegia;

Therapy for rapid and poorly tolerated supra-ventricular tachycardias (SVT) by regularizing 2:1 AV block, lowering mechanical heart rate and improving mechanical function, and may facilitate arrhythmia termination;

Management of dysfunction following tachycardic events including AT, AF, SVT, VT, or VF including elective cardioversion and urgent defibrillation and resuscitation;

Severe bouts of heart failure, worsening to cardiogenic shock, electromechanical dissociation (EMD) or pulseless electrical activity (PEA)

Acute deterioration of cardiac function associated with hypoxia or metabolic disorders;

Intermittent therapy for HF such as prior or during exertion or for worsening symptoms;

Continuous therapy for HF to modify heart rate, improve filling and mechanical efficiency, and facilitate reverse remodeling and other recovery processes;

Scheduled therapy for HF including use for a specified interval of time at a particular time of day or scheduled delivery every N cardiac cycles; and/or Reducing AF burden as a result of reduced atrial loading and better ventricular function during therapy Overview of a System Operating According to the Present Invention A system constructed and operated according to the present invention that may be used to deliver the therapies discussed above may include a signal generator, timing circuit, and/or microprocessor control circuit of the type included in existing pacemaker or ICD systems as is known in the art. Exemplary systems are shown in U.S. Pat. Nos. 5,158,078, 5,318,593, 5,226,513, 5,314,448, 5,366,485, 5,713,924, 5,224,475 and 5,835,975 each of which is incorporated herein by reference, although any other type of pacing and/or ICD system may be used for this purpose. In such systems, EGM sensing is performed by electrodes carried on leads placed within the chambers of the heart, and/or on the housing of the device. Alternatively, subcutaneous and/or external pad or patch electrodes may be used to sense cardiac signals. Physiological sensors may likewise be carried on lead systems according to any of the configurations and/or sensing systems known in the art.

The following introductory material is intended to familiarize the reader with the general nature and some of the features of the present invention.

Brief Description of Electrodes and Leads for Use with the Present Invention.

All embodiments of the present invention share a common need for electrode configurations to deliver electrical stimulation energy where necessary and to time the delivery of this energy to achieve beneficial effects while avoiding unsafe delivery (as further described hereinbelow). For each therapy component described above, specific electrode locations and geometries may be preferred. The locations for the electrodes of this invention for stimulation include: use of large surface area defibrillation coil electrodes in the heart or adjacent to the heart; pacing electrodes at locations including RV apex, outflow tract, atrial locations, HIS bundle site, left side epicardium, pericardium or endocardium; sympathetic nerve regions near the cervical or thoracic spine or nerves or adjacent vessels on or near the heart; transthoracic electrodes including paddles and patches, can electrode, temporary electrodes (e.g., epicardial, transvenous or post-operative electrodes), subcutaneous electrodes and multiple site stimulation.

In accordance with common biomedical engineering practices, stimulation therapy is applied with minimized net charge delivery to reduce corrosion and counteract polarization energy losses. Both energy efficient therapy delivery and electrogram (EGM) sensing benefit from low polarization lead systems. Finally, the electrodes are preferably connected to fast recovery amplifiers that allow EGM sensing soon after therapy delivery.

Brief Description of Sensors for Use with the Present Invention.

The most fundamental sensors are those based on electrograms (ECG or EGMs) and reflect cardiac electrical activity. These sensors require electrodes located where they can readily detect depolarization and repolarization signals as well as sense amplifiers for the monitoring of heart rhythm and diagnosis of arrhythmias.

According to one embodiment, blood pressure sensors, accelerometers, flow probes, microphones, or sonometric crystals may be used to measure flow, force, velocity, movement of the walls of the heart, and/or to estimate the volume of the cardiac chambers. Parameters derived from these sensors can also be used to detect the onset and severity of cardiac hemodynamic dysfunction. For example, HF decompensation may be indicated when a change in long-term diastolic cardiac pressure has increased while contractility of the heart derived from dP/dt rate of rise of ventricular pressure has diminished.

Another embodiment of the invention may utilize changes in transthoracic or intracardiac impedance signals to sense cardiac motion and respiratory movement. Changes in intrathoracic impedance as a result of pulmonary edema may also be used trigger RPS and/or NES stimulation therapy.

In implantable or external devices, metabolic or chemical sensors such as expired $CO_2$ and blood oxygen saturation, pH, $pO_2$, and/or lactate) may be employed to reflect cardiac dysfunction.

Brief Description of Atrial Coordinated Pacing ("ACP") According to the Invention.

According to one form of the invention, electrical stimulation to the upper and/or lower chambers of the heart may be delivered both during refractory and non-refractory periods to coordinate atrial contraction, stabilize the rhythm, and optimize cardiac output. This stimulation is implemented via the present invention in a manner that minimizes the dangers associated with induced arrhythmias. Intrinsic atrial events are followed by ventricular events and manifest as sharp deflections of atrial and ventricular electrograms ("AEGMs" and "VEGMs," respectively).

According to one form of the invention, pacing occurs in the atrium at a rate that is higher than the intrinsic rate. Even though 2:1 conduction is still present, the intrinsic ventricular depolarizations occur more frequently because of the increased atrial rate. Yet another waveform "D" can be used to illustrate another form of ACP which the inventors consider a special case of ACP. In this case, an atrial coordinated pace is initiated a relatively short time period following a ventricular (or atrial) beat. Because of the AV block and the refractory state of the ventricles, this Acp paced event does not conduct to the ventricle. Following this ACP paced beat an intrinsic depolarization is allowed to occur in the atrium (As). This intrinsic beat conducts to the ventricle, resulting in a ventricular depolarization (Vs).

This aspect of the present invention allows a patient's natural AV conduction and intrinsic rate to emerge during the cardiac cycle, providing better rate control during RPS therapy. Extensions to provide a lower rate limit by atrial and/or ventricular pacing are well known in the art of pacing. ACP may be provided by an implantable device as illustrated here or be provided by transcutaneous pacing (TCP) stimulation timed from the surface ECG's R wave by stimuli of sufficient amplitude to capture both atria and ventricles.

Brief Description of NES/Sympathetic Neurostimulation per the Invention.

According to another aspect of the invention, non-excitatory electrical neural stimulation therapies are directed at sympathetic nerves in the neck, chest, mediastinum, and heart to enhance mechanical function by local release of catecholamines, such as norepinephrine. These therapies are known as nonexcitatory electrical stimulation (NES) therapies because they are not intended to cause cardiac tissue depolarization and can be accomplished with electrode locations and stimulation timing that avoid electrically exciting cardiac tissue. Electrodes near the heart deliver one or more NES pulses within the refractory period of the myocardium. Of course, electrodes that direct electrical current away from the myocardium may deliver electrical stimuli at various times throughout the cardiac cycle without directly exciting cardiac tissue.

Brief Description of Safety Lockout Rule(s) Per the Present Invention.

Another aspect of the invention involves delivering electrical stimulation to the atrium and ventricles in a manner that optimizes resulting mechanical function including pressures and flows while minimizing associated risks. Several features of the present invention are provided to achieve this goal, including regulation of NES and RPS therapy delivery to attain the desired level of enhanced function, the use of atrial coordinated pacing, or ACP, to improve rhythm regularity and hemodynamic benefit over NES and/or RPS alone, and a safety rule to inhibit or lockout RPS therapy when it is at risk of being proarrhythmic, diminishing diastole and coronary blood flow, and/or reducing the beneficial effect on hemodynamics. Rapid heart rates are prime examples of when RPS therapy is counter productive and motivate use of a safety lockout rule.

A safety lockout rule operates on a short term or beat-by-beat basis to disable RPS (and ACP, if enabled) if the V-V interval from the prior cycle is too short. Thus, ectopy will suppress RPS therapy as will sinus tachycardia, other SVTs, VTs, and VF. The inventors have discovered that this rule is a key component of safe and effective RPS stimulation therapy in a variety of situations.

As set forth in the '956 application, the present invention maintains adequate arrhythmia detection and in the event that detection occurs, delivery of an ESS therapy is inhibited. Maintaining robust detection of ventricular tachycardia (VT) and ventricular fibrillation (VF) is deemed a prerequisite for secure and efficacious delivery of an ESS therapy.

Representative rules according to the present invention include

Inhibit delivery of an ESS therapy in the event that a PVC occurs on a preceding cardiac cycle.

Withhold delivery of an ESS therapy during VT/VF episodes.

Avoid potential under-sensing of VT by withholding delivery of an ESS therapy in the event that an evidence counting-type VT detection algorithm has reached a threshold (prior to declaring positive detection of VT).

Brief Description of Therapy Start and Stop Rules Per the Invention.

The application of RPS and NES therapy according to the present invention may be altered by (i) a physician (based on laboratory results and the patient's signs and symptoms), (ii) by the patient (to help with anticipated or present symptoms such as associated with exertion), or (iii) automatically by device sensors that detect conditions responsive to these stimulation therapies. In each of these cases there may be distinct maximal therapy durations and termination criteria (or therapy may be ended by the physician or patient).

Automated sensor-governed initiation of stimulation therapies are described herein. If there is no current arrhythmia, physiologic sensors are employed to determine if cardiac hemodynamic dysfunction therapy is to be initiated. Blood pressure signals such as arterial, right ventricular, and/or left ventricular pressure sensors (which may be utilized to derive other discrete cardiovascular pressure measurements) may be used to obtain respective pressure measurements. Therapy may be initiated when these measurements indicate a pressure change that drops below or exceeds a predetermined threshold for an established period of time. In one example depicted in detail herein, a severe level of dysfunction (LV dP/dt max<400 mmHg/s) is observed during normal sinus rhythm for over six seconds. The pressure measurements may be weighted and/or combined to obtain a statistic used to trigger therapy delivery. The statistic may be used to develop long-term trend data used to indicate the onset and severity of HF and hemodynamic dysfunction.

In another aspect of the invention, RV pressure is used to derive RV end-diastolic and developed pressure, maximum pressure change as a function of time (dP/dtmax), an estimate of pulmonary artery diastolic pressure (ePAD), an RV relaxation or contraction time constant (tau), or RV recirculation fraction (RF). These derived parameters are then used to determine when the degree of dysfunction has exceeded an acceptable level such that therapy delivery is initiated. Parameters could be measured or computed as above and compared to thresholds, or sensor signals could be processed and cardiac dysfunction identified through template matching and classification. Thresholds and/or classification schemes may be periodically updated to reject any natural changes in the condition of the patient as cause for therapy.

The present invention may also incorporate predicted hemodynamic compromise through an extended analysis of cardiac cycle-length. For example, a long duration and rapid SVT, VT, or VF has a high likelihood of producing dysfunction including acute HF decompensation, cardiogenic shock, or even electromechanical dissociation (EMD) or pulseless electrical activity (PEA) after spontaneous termination or cardioversion. In such cases, a trial of stimulation therapy might be programmed without mechanical, metabolic, or chemical sensor confirmation.

Other signals such as surface electrocardiogram (ECG) or electrogram (EGM) signals from electrodes within the patient's body may be used to detect dysfunction and heart failure (HF). For example, the ST segment level of a cardiac cycle (PQRST) detected by an ECG may be monitored. An elevated or depressed ST segment level has been found to be reliable indicator of ischemia, a condition known to be associated with dysfunction and HF. Alternatively, the duration of the Q-T interval may also be used to detect hemodynamic dysfunction. For example, a shortened Q-T interval may indicate myocardial dysfunction. A template matching algorithm such as a wavelet classification algorithm may be used to identify electrogram signals that are associated with hemodynamic dysfunction.

Chemical sensors may be used to initiate therapy, including sensors that analyze the blood to detect changes in lactate, $O_2$ saturation, $PO_2$, $PCO_2$ and pH. Expired gas may be analyzed for $PCO_2$ as an indicator of cardiac output during resuscitation procedures. Pulse oximetry may provide noninvasive assessments of oxygen saturation and pulse plethysmogram signals which have particular utility in the context of applying the inventive cardiac therapy with an automatic external defibrillator (AED) following cardioversion of a tachyarrhythmia. Therapy is then continued until the degree of dysfunction or HF reflected by these variables is less than a predetermined amount for a sufficient period of time.

Although pressure sensors figure prominently in the examples above (and in the '631 disclosure) a number of other sensors could reflect mechanical function. Intracardiac or transthoracic impedance changes reflect mechanical function, stroke volume, and cardiac output. Accelerometers or microphones within the body or applied externally sense serious cardiac dysfunction and monitor the response to therapy. Heart volume, dimension changes, and velocities may be measured by implanted or external applications of ultrasound.

Physiologic signals may continue to be sensed to determine if a therapy termination condition is met so that therapy may be terminated. In the context of an AED, for example, this may involve determining that a tachyarrhythmia has terminated and that arterial pulse pressure has reached levels compatible with recovery. The use, however, of a mechanical sensor such as a pressure sensor or an accelerometer to determine whether or not to apply therapy has the drawback in that external treatments of PEA/EMD such as cardiac chest compressions may introduce error into the physiologic signals, inhibiting or delaying therapy when it may be needed. An additional aspect of the invention is to include not only a mechanical sensor in or on the heart to detect cardiac function, but a second sensor or a multitude of sensors away from the heart, such as inside the implantable device housing or can (acting as an indifferent electrode). From this second sensor, CPR artifact (due to chest compressions and the like) could be identified and subtracted to reveal a more accurate assessment of true cardiac function.

Therapy is ordinarily automatically interrupted on detection of an arrhythmic event. Upon termination of the arrhythmic event, the therapy may be automatically reconfigured to reduce risk of re-induction. Therapy could also be interrupted on detection of a sufficient quantity of abnormal depolarizations such as a premature ventricular contraction (PVC). One or more PVCs could be detected through the use of rate limits or through a template matching type algorithm such as a template matching algorithm like a wavelet classification algorithm, or using a PR-logic® type rhythm discrimination scheme which is a proprietary detection technique of Medtronic, Inc.

Brief Description of Identifying the Refractory Interval Per the Invention.

Although beneficial for cardiac function, the delivery of RPS stimulation pulses must be controlled so as to minimize the risk of inducing an arrhythmia. This is best realized with reference to the traces of an ECG or EGM signal aligned with a stimulus-intensity curve to show the intensity of pulses required to induce an extra systole during the time period following a ventricular depolarization which coincides to the QRS complex at an initial time zero (0). During the absolute refractory period, the ventricles are refractory so that another depolarization will not be induced by delivery of electrical stimulation either directly or by applying electrical stimulation to an atrial chamber. Following this time, the tissue recovers so that another electrical depolarization is possible upon the delivery of electrical stimulation to the cardiac tissue. The amount of electrical current required to cause the extra systole during this time is represented by the stimulus-intensity curve.

Initially the electrical current level required to capture the tissue is high but thereafter sharply decreases to a baseline level of roughly 0.5-1 mA for an implanted pacing lead. For TCP via electrode pads or paddles of an AED or external defibrillator the baseline level may be on the order of 50-100 mA.

Also, the "vulnerable period" of the ventricles must be considered when administering RPS therapy. The vulnerable period represents a time period during which an electrical pulse delivered at, or above, a pre-determined amplitude has the risk of causing a VT or VF episode. For example, a pulse delivered at about 170 ms having an amplitude of 40 mA or more may induce an tachyarrhythmia.

The importance of identifying and techniques for identifying the refractory-nonrefractory boundary is described herein. Nonexcitatory neurostimulation benefits arise from pulses anywhere in the refractory period. NES neurostimulation delivered outside the refractory period is frequently excitatory (and will be addressed in the excitatory RPS analysis which follows herein below).

The level of enhancement or potentiation resulting from excitatory RPS stimulation therapy follows a potentiation response curve as further described herein. The inventors have found that such electrical stimulation pulses delivered shortly after the refractory period ends produce strong subsequent contractions. Further delays of the stimulation diminish the amount of potentiation. Stimulation too early (i.e., prematurely) results in no additional potentiation at all since the myocardium is refractory. As discussed with respect to the vulnerable period, the risk of arrhythmia induction is confined to a relatively narrow time interval just slightly longer than the refractory period. However, the inventors have discovered that such a risk is quite low if single RPS pulses are delivered according to the safety lockout rule (briefly described above).

As a result, it is apparent that stimulation timing with respect to the refractory-nonrefractory period boundary is a critical aspect of obtaining the desired response (NES or RPS) and controlling risks and benefits of therapy delivery. The present invention provides for means to determine this time from electrical, and/or mechanical sensor signals and thereby enable safer and more effective stimulation therapies.

The inventors exploit the fact that the refractory period is closely associated with the Q-T interval, which may be derived from electrogram signals or other physiologic sensor signals by techniques known in the art. The Q-T interval length is used to estimate the duration of the refractory period either directly, or by incorporating a function of heart rate and sensing delays. In the case of RPS therapy, the Q-T interval length can be estimated by the time interval from an extra systole stimulation pulse to an evoked T wave and would be slightly longer than during a cardiac cycle not associated with PESP. This is because the extra depolarization caused by the RPS prolongs the QT interval slightly.

Alternatively, an evoked response of the RPS stimulation could be monitored to indicate whether the RPS therapy was delivered in the refractory period or not. For example, a number of electrical pulses are applied to the myocardium, beginning during the refractory period. The result of each pulse is sensed on an EGM from either the stimulating electrode or an auxiliary electrode until an evoked response is sensed, indicating that the pulse caused an extra systole. At this point, no further pulses would be applied to minimize the risk of inducing arrhythmias.

In another example, a single pulse's amplitude and timing may be manipulated until capture is detected by an evoked R wave. If capture is lost, the stimulus pulse is delayed more, or amplitude increased, or the number of pulses in a RPS pulse train is increased. Also, the characteristics of a pressure waveform (or any other mechanical response variable) used to assess whether the RPS stimulation is/was capturing the ventricles can be utilized when practicing the present invention. The presence of the extra systole could be identified by a small ventricular pressure pulse 5-80% of the size of the preceding pressure pulse or through a suitable algorithm such as a template matching algorithm.

The inventive system may also deliver optional non-excitatory neurostimuli using a waveform including one or more pulses during the refractory period. To ensure that the NES stimulation does not enter the vulnerable period, the length of the refractory period is estimated using the mechanisms discussed above. If NES is exclusively intended, then detection of an extra systole—due to a capturing pulse delivered outside the refractory period—should result in a reduction of the stimulus delay time, amplitude, or pulse number.

As the refractory-nonrefractory boundary is very important and varies from patient to patient and even with a patient over time, with disease and drugs, these methods are to be employed periodically or continually to the stimulation timing algorithm portion of the device. If this boundary information is not used to set pulse timing directly, it may be employed to establish limits for the timing that is in turn set by a clinician or some automatic control algorithm such as that described next.

Brief Description of Feedback Control of Stimulation Therapy Per the Invention.

According to yet another aspect of the invention, closed-loop feedback from physiologic sensors is used to adjust the timing of the electrical stimulation so that therapy delivery may be tuned to further optimize cardiac function, maintain safety, and accommodate variations in the heart's responsiveness. The basic nonexcitatory neurostimulation (NES) response curve (a function of stimulus intensity in the refractory period). Changes from patient to patient or within a patient (over time) may lead to different levels of enhanced function for a fixed NES stimulus. Conversely, maintenance of a desired level of enhancement may require different stimulation times or intensities.

Sensor signal feedback may be used to govern stimulation timing in a closed loop fashion to accommodate variations in responsiveness. A physician may react to physiologic information and adjust the electrical stimulation amplitude and timing. In the alternative, this reaction may be accomplished by the device according to an algorithm referred to as a controller. An elementary but useful and widely used family of controllers is referred to as PID or P+I+D control. PID controllers work with an error signal that reflects how far the sensor level is from a target level or setpoint. The controller's output is a combination of the error signal, the integral of the error, and the derivative of the error each scaled by a constant denoted P, I, and D, respectively. Practical controllers incorporate limits on their outputs and integrators so as to keep the input to system they influence (called a plant) within reasonable bounds and maintain responsiveness.

An illustration of a functioning P+I controller based on RV dP/dtmax is disclosed herein for use in conjunction with the present invention. As an example, a setpoint of 700 mmHg/s was chosen for RPS stimulation from a baseline of 280 mmHg/s and the controller and therapy begun. The RPS stimulation pulse was automatically adjusted each cardiac cycle based on the P+I controller within upper and lower limits. In the course of our research we increased the controller's gains which led to oscillation. Using less gain it was possible to trade a little sluggishness in response for a great deal of robustness to variations in the plant's response by exploiting feedback control.

It may be noted that stimulation time, as well as the maximum amplitude, pulse intervals, number of pulses in a train, change in the amplitude of sequential pulses in the pulse train, and other parameters may be adjusted to achieve optimal cardiac performance for a given patient. This may be accomplished by monitoring sensed physiologic parameters in a closed-loop manner. The pulse train may then be adjusted accordingly to maximize cardiac output or other indices of physiologic function. For example, rather than altering the timing of a single RPS pulse, the controller may alter the number and duration of a pulse train.

The NES stimulation may also be modulated to further improve cardiac function using physiologic signal monitoring in a closed-loop environment very similar to that discussed above for RPS therapy. The various pulse trains found to be most effective for use in NES and RPS therapies are described in more detail in the related applications incorporated herein. The number of pulses, pulse amplitude, pulse shape, and any other aspect of the signal may be varied based on physiologic measurements to maximize cardiac output. Both the NES and RPS pulse trains may be optimized to achieve maximum cardiac function. Both NES and RPS therapies need not be applied every cardiac cycle but could skip a specific number of cycles between applications (e.g., for one hour out of every six hours, manually triggered by a patient, triggered based on detected physiologic state of a patient such as high or variable heart rate, etc.). The number of cycles skipped could also serve as a control variable.

Brief Description of Extensions to Tachyarrhythmia Management Devices.

An additional aspect of this invention is to change existing regimens for the delivery of anti-tachycardia pacing (ATP) and shocks for cardioversion and defibrillation, given that cardiac stimulation therapy may be activated following these therapies. A flowchart illustrating this aspect of the invention appears herein and is applicable for both ICDs (implantable cardiovertor defibrillators) and AEDs (automated external defibrillators).

The first change to existing and prior art regimens is to increase the number of shocks beyond the present upper limit.

A second change is to increase the time between the later shocks in the sequence. With greater spacing, higher detection specificity would be possible and minimize the potential risk of shock-induced myocardial damage.

A third change would be to monitor the EGM for increased regularity and/or increased amplitude which may be an indicator as to when it would be most efficacious to deliver the extra shocks.

An additional aspect of this invention is to modify existing rhythm recognition algorithms of implanted and external therapy devices to accommodate operating concurrently with therapy pulses delivered by a preexisting external or implanted device respectively. The sharp changes in electrogram slew rate associated with stimulation pulses may be recognized and ignored for the purpose of automated rhythm recognition. The devices analyze the effective heart rate and rhythm accordingly and do not falsely detect or treat tachyarrhythmias.

Brief Description of a System Comprising the Present Invention.

A comprehensive flowchart depicting a high level view of the present invention showing the integration significant aspects for non-excitatory RPS stimulation is included herewith. A representative heart and cardiovascular system is influenced by electrical therapies including pacing, defibrillation, CRT, RPS and, optionally, NES stimulation therapy. The heart and cardiovascular system may be monitored by electrical, mechanical, and metabolic/chemical sensors. The signals from these sensors influence decisions to start or stop therapy, closed loop control, refractory period detection, therapy safety lockout rules, and atrial coordinated pacing.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views. The drawings are not drawn to scale and do not necessarily include all elements of every embodiment of the present invention.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention.

Figure 1:
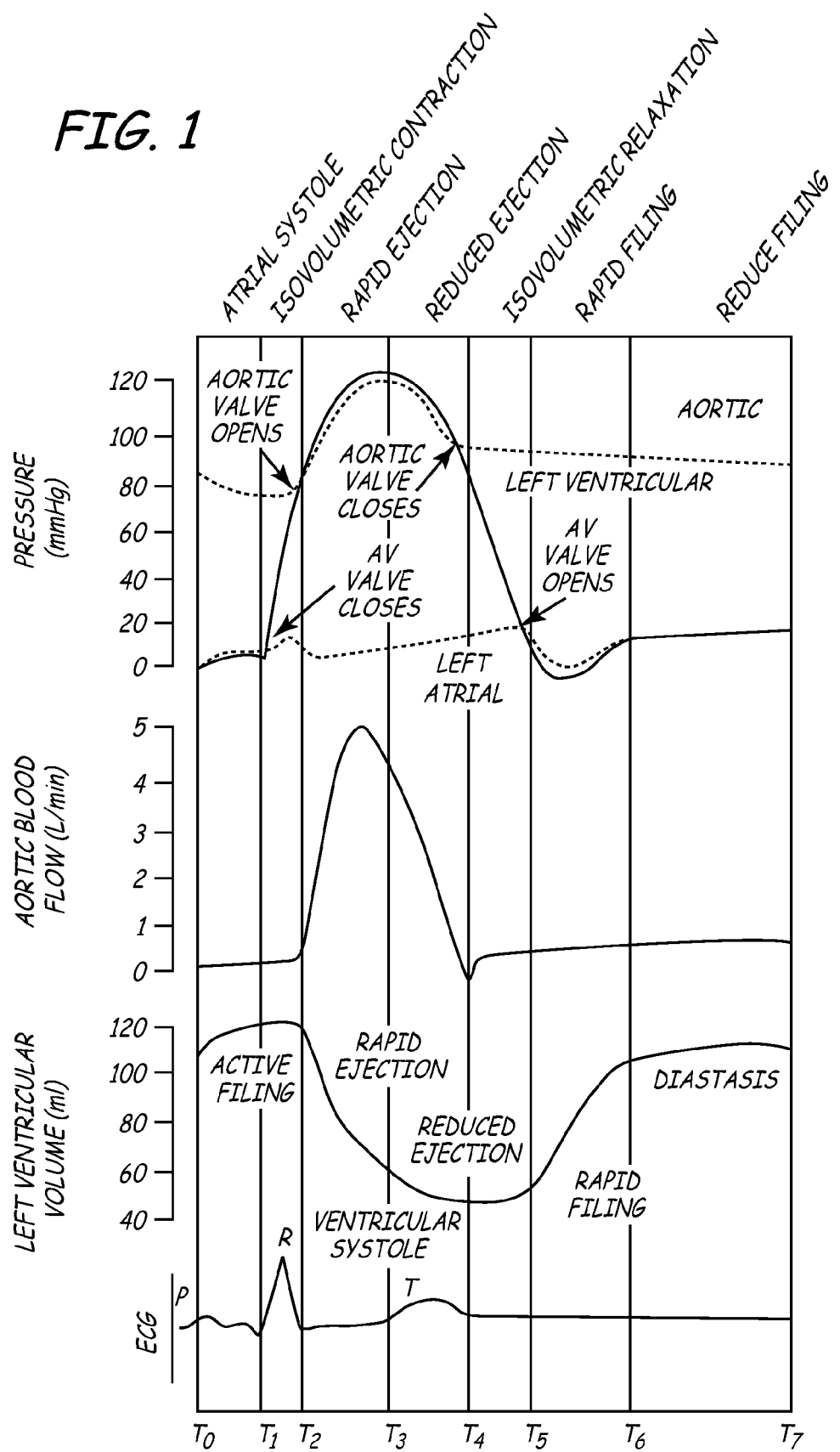
FIG. 1 depicts the relationship of heart chamber EGM, pressure, flow, and volume during a cardiac cycle.

Before describing the preferred embodiments, reference is made to FIG. 1 reproduced from the above-referenced '464 patent which depicts the electrical depolarization waves attendant a normal sinus rhythm cardiac cycle in relation to the fluctuations in absolute blood pressure, aortic blood flow and ventricular volume in the left heart. The right atria and ventricles exhibit roughly similar pressure, flow and volume fluctuations, in relation to the PQRST complex, as the left atria and ventricles. It is understood that the monitoring and stimulation therapy aspects of this invention may reside and act on either or both sides of the heart. The cardiac cycle is completed in the interval between successive PQRST complexes and following relaxation of the atria and ventricles as the right and left atria re-fill with venous blood and oxygenated blood. In sinus rhythm, the interval between depolarizations may be on the order of 500.0 ms to 1,000.0 ms for a corresponding sinus heart rate of 120 bpm to 60 bpm, respectively. In this time interval, the atria and ventricles are relaxed, and overall atrial size or volume may vary as a function of pleural pressure and respiration. In the blood pressure diagrams of FIG. 1, it may be observed that the atrial and ventricular blood pressure changes track and lag the P-waves and R-waves of the cardiac cycle. The time period $T_0$-$T_1$ encompasses the AV interval.

In patients suffering from cardiac insufficiency arising from bradycardia due to an incompetent SA node or AV-block, atrial and/or ventricular conventional pacing may be prescribed to restore a sufficient heart rate and AV synchrony. In FIG. 1 for example, atrial and/or ventricular pacing pulses would precede the P-wave and the deflection of the QRS complex commonly referred to as the R-wave. Cardiac output may be reduced by the inability of the atrial or ventricular myocardial cells to relax following atrial ($T_0$-$T_1$) and ventricular ($T_1$-$T_2$) systolic periods. Prolonged systolic time periods reduce passive filling time $T_4$-$T_7$ as shown in FIG. 1. Thus, the amount of blood expelled from the atria and/or ventricles in the next cardiac cycle may be less than optimum. This is particularly the case with HF patients or other patients in whom the stiffness of the heart is increased, cardiac filling during the passive filling phase ($T_4$-$T_7$) and during atrial systole ($T_0$-$T_1$) is significantly limited.

It will be appreciated from the following description that the monitor/therapy delivery IMD of the present invention may be utilized to obtain the aforementioned parameters as stored patient data over a period of time and to deliver therapies for treating the heart failure. The physician is able to initiate uplink telemetry of the patient data in order to review it to make an assessment of the heart failure state of the patient's heart. The physician can then determine whether a particular therapy is appropriate, prescribe the therapy for a period of time while again accumulating the stored patient data for a later review and assessment to determine whether the applied therapy is beneficial or not, thereby enabling periodic changes in therapy, if appropriate. Such therapies include drug therapies and electrical stimulation therapies, including RPS and/or NES stimulation, and pacing therapies including single chamber, dual chamber and multi-chamber (bi-atrial and/or bi-ventricular) pacing. Moreover, in patients prone to malignant tachyarrhythmias, the assessment of heart failure state can be taken into account in setting parameters of detection or classification of tachyarrhythmias and the therapies that are delivered.

Accordingly, an embodiment of the invention is disclosed in detail in the context of a multi-chamber pacing system that is modified to derive the aforementioned parameters indicative of cardiac mechanical dysfunction from sensors, sense electrodes and electrical stimulation electrodes located in operative relation to one or more heart chamber. This embodiment of the invention may be programmed to operate as an AV sequential, bi-atrial and bi-ventricular, pacing system operating in demand, atrial tracking, and triggered pacing for restoring synchrony in depolarizations and contraction of left and right ventricles in synchronization with atrial sensed and paced events for treating HF and/or bradycardia. This embodiment of the invention is therefore programmable to operate as a two, three or four channel pacing system having an AV synchronous operating mode for restoring upper and lower heart chamber synchronization and right and left atrial and/or ventricular chamber depolarization synchrony. However, it will be understood that only certain of the components of the complex multi-chamber pacing system described below can be selectively programmed to function or physically only incorporated into a simpler, single chamber, monitoring/stimulation system for deriving the parameters indicative of heart failure state.

Figure 2:
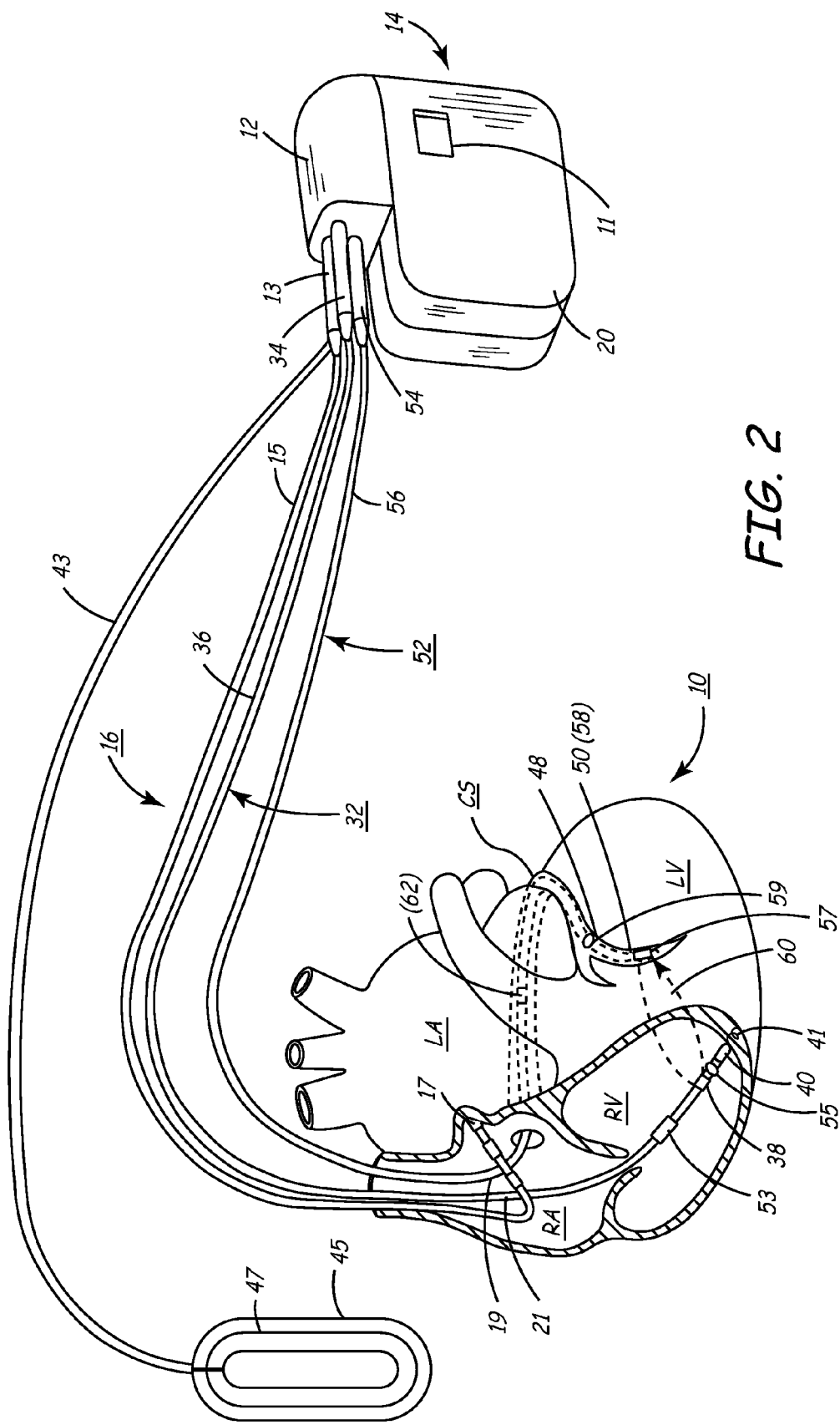
FIG. 2 is a schematic diagram depicting a multi-channel, atrial and bi-ventricular, monitoring/pacing IMD in which the present invention is preferably implemented.

In FIG. 2, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein that extends further inferiority into branches of the great vein. The cardiac cycle commences normally with the generation of the depolarization impulse at the SA Node in the right atrial wall. The impulse then conducts through the right atrium by way of Internodal Tracts, and conducts to the left atrial septum by way of Bachmann's Bundle. The RA depolarization wave reaches the Atrio-ventricular (AV) node and the atrial septum within about 40 msec and reaches the furthest walls of the RA and LA within about 70 msec. Approximately 50 ms following electrical activation, the atria contract. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node conducts down the bundle of His in the intraventricular septum after a delay of about 120 msec. The depolarization wave reaches the apical region of the heart about 20 msec later and is then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent to the RV or LV exceeds a threshold amplitude, it is detected as a sensed R-wave. Although the location and spacing of the external ECG electrodes or implanted unipolar ventricular pace/sense electrodes has some influence on R-wave sensing, the normal R-wave duration does not exceed 80 msec as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The normal electrical activation sequence becomes highly disrupted in patients suffering from advanced HF and exhibiting Intra-atrial conduction delay (IACD), Left Bundle Branch Block (LBBB), Right Bundle Branch Block (RBBB), and/or Intraventricular Conduction Delay (IVCD). These conduction defects give rise to great asynchrony between RV activation and LV activation. Inter-ventricular asynchrony can range from 80 to 200 msec or longer. In RBBB and LBBB patients, the QRS complex is widened far beyond the normal range to between 120 msec and 250 msec as measured on surface ECG. This increased width demonstrates the lack of synchrony of the right and left ventricular depolarizations and contractions.

FIG. 2 also depicts an implanted, multi-channel cardiac pacemaker, ICD, IPG or other IMD of the above noted types for restoring AV synchronous contractions of the atrial and ventricular chambers and simultaneous or sequential pacing of the right and left ventricles. The pacemaker IPG 14 is implanted subcutaneously in a patient's body between the skin and the ribs. Three endocardial leads 16, 32 and 52 connect the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV CS lead 52 is passed through a vein and the RA chamber of the heart 10, into the CS and then inferiority in a branching vessel of the great vein 48 to extend the distal LV CS pace/sense electrode 50 alongside the LV chamber. The distal end of such LV CS leads is advanced through the superior vena cava, the right atrium, the ostium of the coronary sinus, the coronary sinus, and into a coronary vein descending from the coronary sinus, such as the great vein. Typically, LV CS leads and LA CS leads do not employ any fixation mechanism and instead rely on the close confinement within these vessels to maintain the pace/sense electrode or electrodes at a desired site. The LV CS lead 52 is formed with a small diameter single conductor lead body 56 coupled at the proximal end connector 54 fitting into a bore of IPG connector block 12. A small diameter unipolar lead body 56 is selected in order to lodge the distal LV CS pace/sense electrode 50 deeply in a vein branching inferiority from the great vein 48.

Preferably, the distal, LV CS active pace/sense electrode 50 is paired with the proximal ring RV indifferent pace/sense electrode 38 for delivering LV pace pulses across the bulk of the left ventricle and the intraventricular septum. The distal LV CS active pace/sense electrode 50 is also preferably paired with the distal tip RV active pace/sense electrode 40 for sensing across the RV and LV as described further below.

Moreover, in a four-chamber embodiment, LV CS lead 52 could bear a proximal LA CS pace/sense electrode positioned along the lead body to lie in the larger diameter coronary sinus CS adjacent the LA. In that case, the lead body 56 would encase two electrically insulated lead conductors extending proximally from the more proximal LA CS pace/sense electrode(s) and terminating in a bipolar connector 54. The LV CS lead body would be smaller between the proximal LA CS electrode and the distal LV CS active pace/sense electrode 50. In that case, pacing of the RA would be accomplished along the pacing vector between the active proximal LA CS active electrode and the proximal ring RA indifferent pace/sense electrode 21.

Typically, in pacing/defibrillation systems of the type illustrated in FIG. 2, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors. Separate or shared indifferent pace and sense electrodes can also be designated in pacing and sensing functions. For convenience, the following description separately designates pace and sense electrode pairs where a distinction is appropriate. With respect to the present invention, a subcutaneous electrode 45 coupled to medical electrical lead 43 may be added to or substituted for one or more of the leads or electrodes depicted in FIG. 2. If a subcutaneous electrode 45 is utilized, a suitable defibrillation coil 47 may be coupled to appropriate high voltage circuitry to deliver a timed defibrillation pulse. While coil electrode 53 is depicted coupled to a portion of RV lead 32, such an electrode may be coupled to other portions of any of the leads depicted in FIG. 2, such as LV electrode 57. The coil electrode 53, subcutaneous electrode 45 or other types of suitable electrode configurations may be electrically coupled to low voltage pacing/sensing circuitry in addition to high voltage circuitry. As is known, such electrodes may be disposed in a variety of locations in, around and on the heart.

Also depicted in FIG. 2 is an RV sensor 55 and an LV sensor 59 which may comprise one or more of a variety of sensors as is known in the art. Preferably RV sensor 55 comprises an absolute pressure sensor, but other pressure sensors may be utilized. In addition, RV sensor 55 may comprise an accelerometer, an impedance electrode, a saturated oxygen sensor, a pH sensor, and the like. In addition, each of the leads could carry a mechanical sensor for developing systolic and diastolic pressures and a series of spaced apart impedance sensing leads for developing volumetric measurements of the expansion and contraction of the RA, LA, RV and LV.

Of course, such sensors must be rendered biocompatible and reliable for long-term use. With respect to embodiments of the invention delivering NES therapy, the preferred location for at least one electrode is in the coronary venous system in close proximity to adjacent sympathetic nerves. In addition, one or more sensors may be disposed in or on the housing 20 of IMD 14 such as sensor 11 depicted in FIG. 2.

Figure 3A:
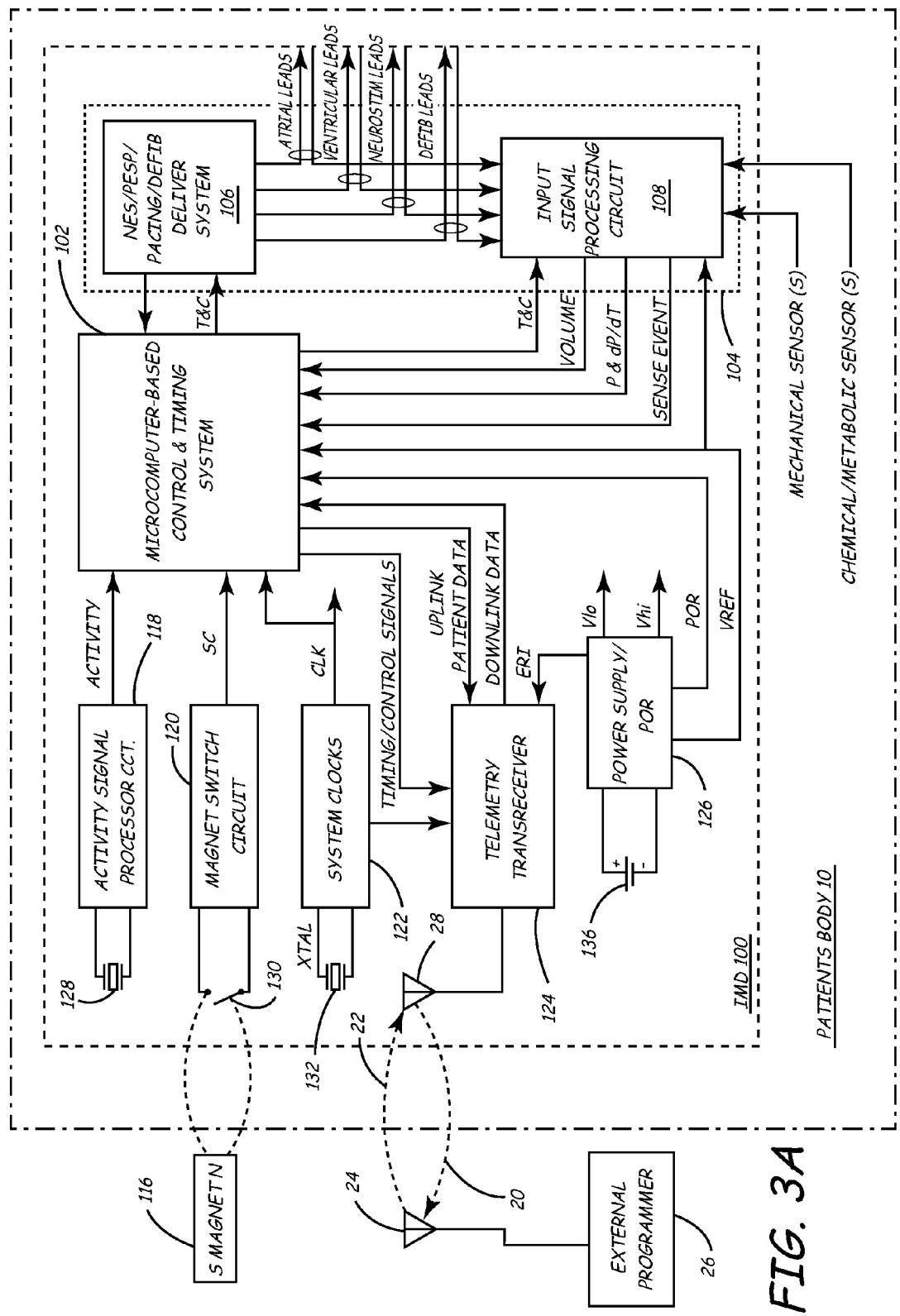
FIG. 3 is a simplified block diagram of one embodiment of IPG circuitry and associated leads employed in the system of FIG. 1 enabling selective therapy delivery and heart failure state monitoring in one or more heart chamber.

FIG. 3A depicts a system architecture of an exemplary multi-chamber monitor/sensor 100 implanted into a patient's body 10 that provides delivery of a therapy and/or physiologic input signal processing. The typical multi-chamber monitor/sensor 100 has a system architecture that is constructed about a microcomputer-based control and timing system 102 that varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU, ALU, etc., of a typical microprocessor core architecture. Of course, such firmware and software may be modified in situ (e.g., in vivo) and the operational characteristics may be adapted for a particular situation or patient. A physician or clinician may change or more parameter which will cause a change in the detection or response of such algorithms. Oftentimes, discrete values may be changed such that a desired software routine is advantageously altered, although sometimes an entirely new set of operating software may be substituted for an existing set of operating software, as is known in the art. The microcomputer-based multi-chamber monitor/sensor control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber monitor/sensor 100 can be accomplished with dedicated circuit hardware or state machine logic rather than a programmed micro-computer.

The multi-chamber monitor/sensor 100 also typically includes patient interface circuitry 104 for receiving signals from sensors and pace/sense electrodes located at specific sites of the patient's heart chambers and/or delivering RPS stimulation to derive heart failure parameters or a pacing therapy to the heart chambers. The patient interface circuitry 104 therefore comprises a RPS stimulation delivery system 106 optionally including pacing and other stimulation therapies and a physiologic input signal processing circuit 108 for processing the blood pressure and volumetric signals output by sensors. For purposes of illustration of the possible uses of the invention, a set of lead connections are depicted for making electrical connections between the therapy delivery system 106 and the input signal processing circuit 108 and sets of pace/sense electrodes located in operative relation to the RA, LA, RV and LV.

As depicted in FIG. 3A, chemical/metabolic sensor input and/or mechanical sensor inputs are provided to the input signal processing circuit 108. As described with respect to FIG. 2, a wide variety of such sensors may be utilized when practicing the present invention.

A battery provides a source of electrical energy to power the multi-chamber monitor/sensor operating system including the circuitry of multi-chamber monitor/sensor 100 and to power any electromechanical devices, e.g., valves, pumps, etc. of a substance delivery multi-chamber monitor/sensor, or to provide electrical stimulation energy of an ICD shock generator, cardiac pacing pulse generator, or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106.

In order for the exemplary circuit of FIG. 3A to implement NES or cardiac defibrillation therapy according to the present invention, the therapy delivery system 106 needs to utilize appropriate NES and high voltage circuitry, respectively. If an NES therapy delivery electrode is disposed remotely from the heart the delivery of NES therapy may occur independent of the cardiac cycle (e.g., periodically approximately between 10 ms and about ten seconds). While many different types of pulses may be employed for NES therapy, one or more pulses of about 0.1 to about 10 ms duration have been shown to provide the desired results. Effective NES therapy may be delivered using a variety of electrode configuration (e.g., between one and several discrete electrodes). Also, standard tip, ring, coil, can, and subcutaneous electrodes may be utilized to effectively deliver NES therapy. While not specifically depicted in the drawings, suitable external circuitry may be adapted for NES therapy delivery including use of surface electrode patches, pads or paddles as well as pericardial electrodes. In particular, one or more electrodes disposed in the pericardial sac will be well positioned to stimulate the sympathetic nerves.

Virtually all current electronic multi-chamber monitor/sensor circuitry employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 3A, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers may be used for storing data compiled from sensed cardiac activity and/or relating to device operating history or sensed physiologic parameters for uplink telemetry transmission on receipt of a retrieval or interrogation instruction via a downlink telemetry transmission. The criteria for triggering data storage can also be programmed in via downlink telemetry transmitted instructions and parameter values The data storage is either triggered on a periodic basis or by detection logic within the physiologic input signal processing circuit 108 upon satisfaction of certain programmed-in event detection criteria. In some cases, the multi-chamber monitor/sensor 100 includes a magnetic field sensitive switch 130 that closes in response to a magnetic field, and the closure causes a magnetic switch circuit to issue a switch closed (SC) signal to control and timing system 102 which responds in a magnet mode. For example, the patient may be provided with a magnet 116 that can be applied over the subcutaneously implanted multi-chamber monitor/sensor 100 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later interrogation session.

In the multi-chamber monitor/sensor 100, uplink and downlink telemetry capabilities are provided to enable communication with either a remotely located external medical device or a more proximal medical device on the patient's body or another multi-chamber monitor/sensor in the patient's body as described above with respect to FIG. 2 and FIG. 3A (and FIG. 3B described below). The stored physiologic data of the types described above as well as real-time generated physiologic data and non-physiologic data can be transmitted by uplink RF telemetry from the multi-chamber monitor/sensor 100 to the external programmer or other remote medical device 26 in response to a downlink telemetered interrogation command. The real-time physiologic data typically includes real time sampled signal levels, e.g., intracardiac electrocardiogram amplitude values, and sensor output signals. The non-physiologic patient data includes currently programmed device operating modes and parameter values, battery condition, device ID, patient ID, implantation dates, device programming history, real time event markers, and the like. In the context of implantable pacemakers and ids, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/sensor thus develops a variety of such real-time or stored, physiologic or non-physiologic, data, and such developed data is collectively referred to herein as "patient data."

The physiologic input signal processing circuit 108 therefore includes at least one electrical signal amplifier circuit for amplifying, processing and in some cases detecting sense events from characteristics of the electrical sense signal or sensor output signal. The physiologic input signal processing circuit 108 in multi-chamber monitor/sensors providing dual chamber or multi-site or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an ASENSE or VSENSE event signal to the control and timing system 102. Timing and control system 102 responds in accordance with its particular operating system to deliver or modify a pacing therapy, if appropriate, or to accumulate data for uplink telemetry transmission or to provide a Marker Channel® signal in a variety of ways known in the art.

In addition, the input signal processing circuit 108 includes at least one physiologic sensor signal processing channel for sensing and processing a sensor derived signal from a physiologic sensor located in relation to a heart chamber or elsewhere in the body.

Figure 3B:
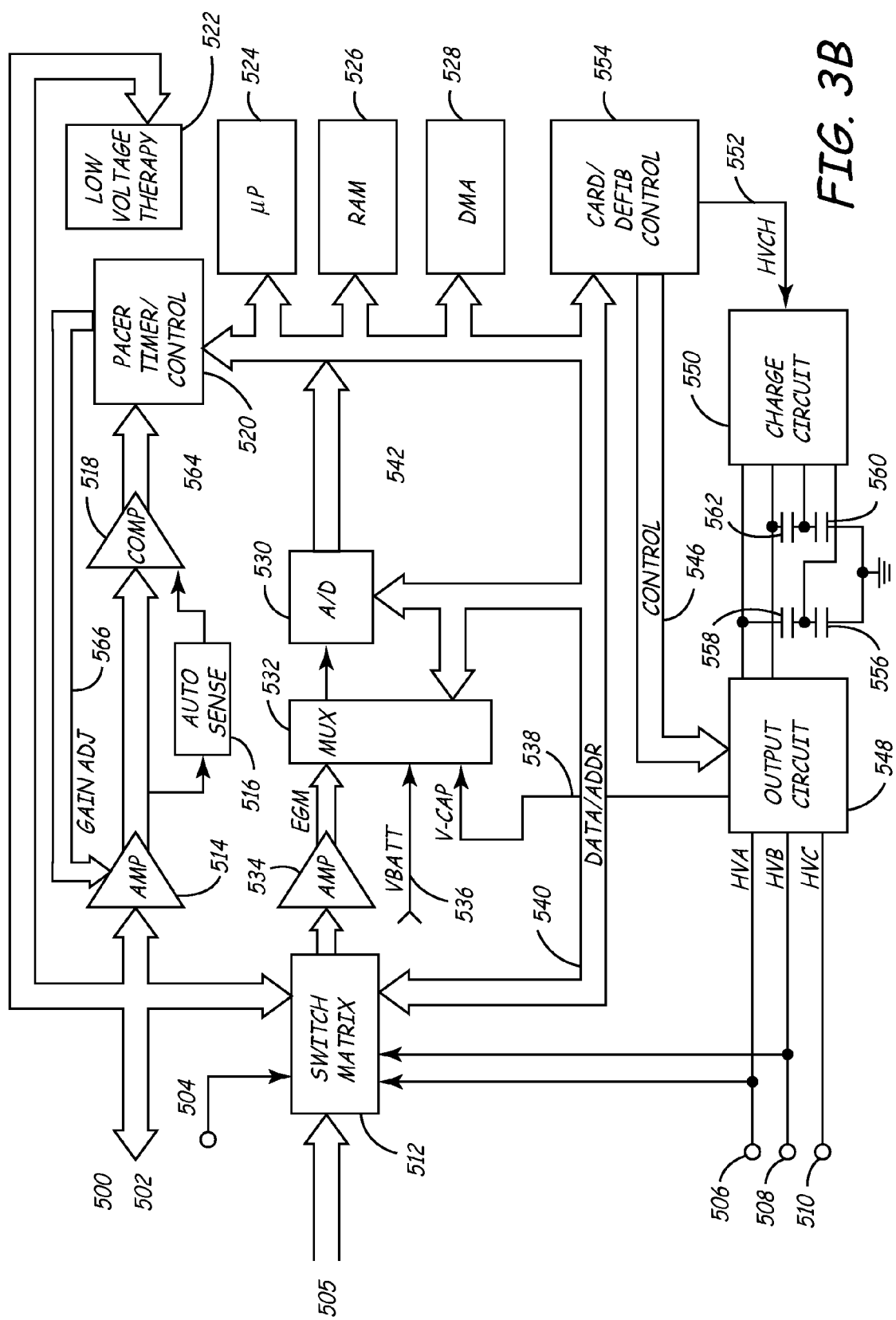

Now turning to FIG. 3B, another system architecture for use in conjunction with the present invention is depicted. FIG. 3B is an exemplary system that may be utilized to deliver therapy by incorporating the system and method described above. Notably, the depicted system includes a sense amplifier 534 to sense electrical signals such as EGM signals using one or more leads placed within a respective chamber of the heart. These signals are used to determine atrial and ventricular depolarizations and Q-T length so that NES and RPS delivery is provided in a safe manner. One or more physiological or hemodynamic signals may be sensed using sensors such as those discussed above. These additional signals, which are shown collectively provided on line 505, may be used to determine cardiac output so that therapy may be initiated, terminated, and/or optimized.

The system of FIG. 3B further includes a timer/controller to control the delivery of pacing pulses on output lines 500 and 502. This circuit, alone or in conjunction with microprocessor 524, controls interval lengths, pulse amplitudes, pulse lengths, and other waveform attributes associated with the NES and RPS pulses. Output circuit 548 delivers high-voltage stimulation such as defibrillation shocks under the control of defibrillation control circuit 554.

Not all of the conventional interconnections of these voltages and signals are shown in either FIG. 3A or FIG. 3B and many other variations on the illustrated electronic circuitry are possible, as is known to those of skill in the art.

Figure 4:
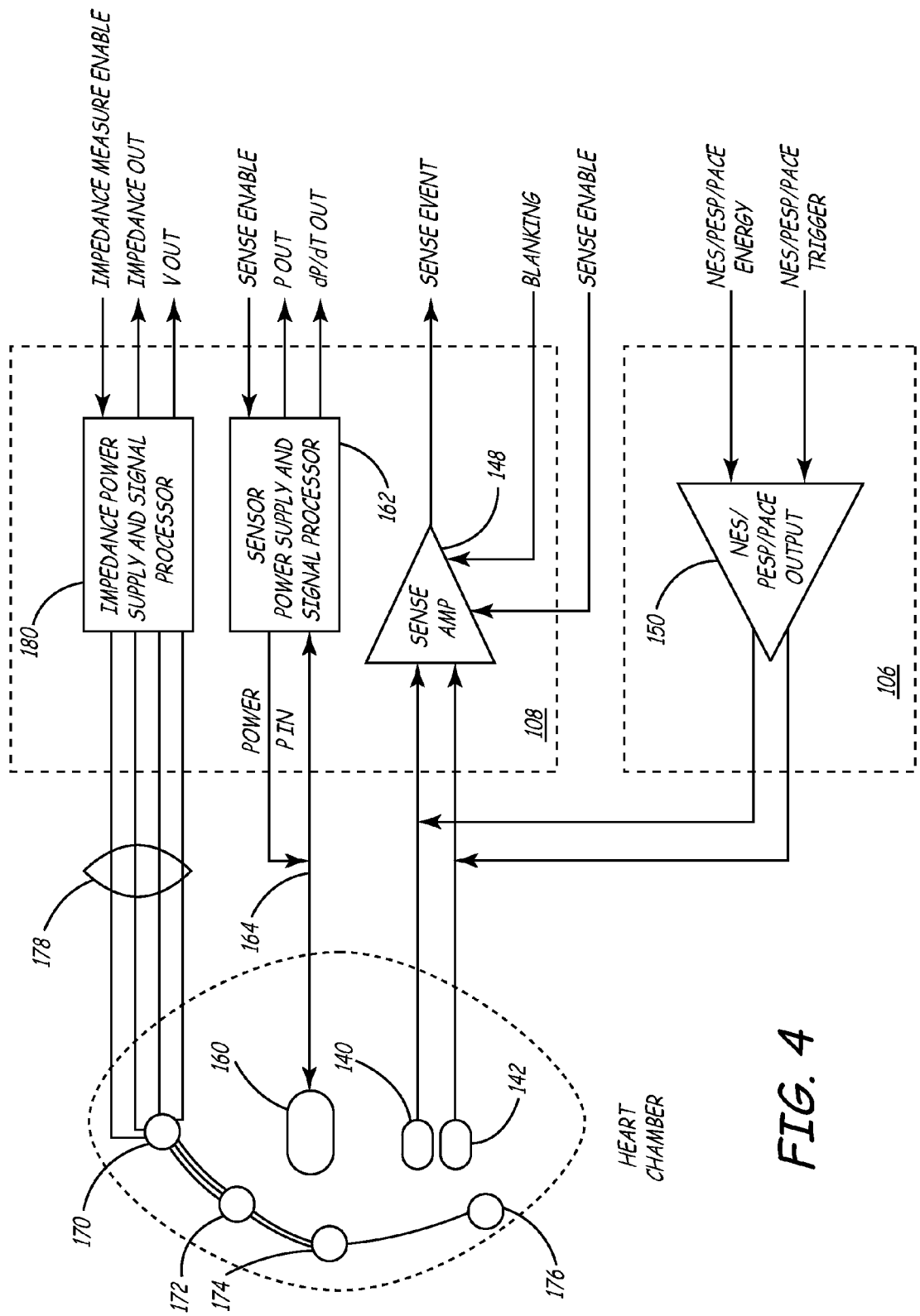
FIG. 4 is a simplified block diagram of a single monitoring and pacing channel for deriving pressure, impedance and cardiac EGM signals employed in monitoring HF and optionally pacing the heart and delivering RPS therapy in accordance with the present invention.

FIG. 4 schematically illustrates one pacing, sensing and parameter measuring channel in relation to one heart chamber. A pair of pace/sense electrodes 140,142, a sensor 160 (e.g., a pressure, saturated oxygen, flow, pH or the like), and a plurality, e.g., four, impedance measuring electrodes 170, 172,174,176 are located in operative relation to the heart chamber. The pair of pace/sense electrodes 140, 142 are located in operative relation to the heart chamber and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled as described below in reference to the measurement of the parameters of heart failure. The blanking signal is provided by control and timing system 102 upon delivery of a pacing or RPS pulse or pulse train to disconnect the sense amplifier inputs from the lead conductors 144 and 146 for a short blanking period in a manner well known in the art. When sense amplifier 148 is enabled and is not blanked, it senses the electrical signals of the heart, referred to as the EGM, in the heart chamber. The sense amplifier provides a sense event signal signifying the contraction of the heart chamber commencing a heart cycle based upon characteristics of the EGM, typically the P-wave when the heart chamber is the RA or LA and the R-wave, when the heart chamber is the RV or LV, in a manner well known in the pacing art. The control and timing system responds to non-refractory sense events by restarting an escape interval (EI) timer timing out the EI for the heart chamber, in a manner well known in the pacing art.

The pair of pace/sense electrodes 140, 142 are also coupled through lead conductors 144 and 146, respectively, to the output of a pulse generator 150. The pulse generator 150, within RPS/pacing delivery system 106, selectively provides a pacing pulse to electrodes 140, 142 in response to a RPS/PACE trigger signal generated at the time-out of the EI timer within control and timing system 102 in a manner well known in the pacing art. Or, the pulse generator 150 selectively provides a RPS pulse or pulse train to electrodes 140, 142 in response to a RPS/PACE trigger signal generated at the time-out of an ESI timer within control and timing system 102 in the manner described in the above-referenced '098 patent to cause the heart chamber to contract more forcefully, the increased force depending upon the duration of the ESI.

The sensor 160 and/or other physiologic sensor is coupled to a sensor power supply and signal processor 162 within the input signal processing circuit 108 through a set of lead conductors 164 that convey power to the sensor 160 and sampled blood pressure P signals from the sensor 160 to the sensor power supply and signal processor 162. The sensor power supply and signal processor 162 samples the blood pressure impinging upon a transducer surface of the sensor 160 located within the heart chamber when enabled by a sense enable signal from the control and timing system 102. As an example, absolute pressure P, developed pressure DP and pressure rate of change dP/dt sample values can be developed by sensor power supply and signal processor unit 162 or by the control and timing system 102 for storage and processing as described further below. The sensor 160 and a sensor power supply and signal processor 162 may take the form disclosed in commonly assigned U.S. Pat. No. 5,564,434.

The set of impedance electrodes 170, 172, 174 and 176 is coupled by a set of conductors 178 and is formed as a lead of the type described in the above-referenced '717 patent that is coupled to the impedance power supply and signal processor 180. Impedance-based measurements of cardiac parameters such as stroke volume are known in the art as described in the above-referenced '417 patent which discloses an impedance lead having plural pairs of spaced surface electrodes located within the heart chamber. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

A measure of heart chamber volume V is provided by the set of impedance electrodes 170, 172, 174 and 176 when the impedance power supply and signal processor 180 is enabled by an impedance measure enable signal provided by control and timing system 102. A fixed current carrier signal is applied between the pairs of impedance electrodes and the voltage of the signal is modulated by the impedance through the blood and heart muscle which varies as distance between the impedance electrodes varies. Thus, the calculation of the heart chamber volume V signals from impedance measurements between selected pairs of impedance electrodes 170, 172, 174 and 176 occurs during the contraction and relaxation of the heart chamber that moves the spaced apart electrode pairs closer together and farther apart, respectively, due to the heart wall movement or the tidal flow of blood out of and then into the heart chamber. Raw signals are demodulated, digitized, and processed to obtain an extrapolated impedance value. When this value is divided into the product of blood resistivity times the square of the distance between the pairs of spaced electrodes, the result is a measure of instantaneous heart chamber volume V within the heart chamber.

In accordance with the present invention, the IMD measures a group of parameters indicative of the state of heart failure employing EGM signals, measures of absolute blood pressure P and/or dP/dt, saturated oxygen, flow, pH or the like and measures of heart chamber volume V over one or more cardiac cycles.

The steps of deriving the RF, MR, $E_{ES}$, and tau parameters indicative of the state of heart failure are more fully described in the '631 disclosure and will not be repeated here. For the uninitiated the following description is provided; however, if additional details are desired the reader is directed to the '631 disclosure. These parameters are determined periodically throughout each day regardless of patient posture and activity. However, the patient may be advised by the physician to undertake certain activities or movements at precise times of day or to simultaneously initiate the determination of the parameters though use of a magnet or a remote system programmer unit (not depicted) that is detected by the IMD. Certain of the parameters are only measured or certain of the parameter data are only stored when the patient heart rate is within a normal sinus range between programmed lower and upper heart rates and the heart rhythm is relatively stable. The parameter data and related data, e.g., heart rate and patient activity level, are date and time stamped and stored in IMD memory for retrieval employing conventional telemetry systems. Incremental changes in the stored data over time provide a measure of the degree of change in the heart failure condition of the heart. Such parameter data and related data may be read, reviewed, analyzed and the like and the parameter data may be changed based on a current patient condition, a patient history, patient or physician preference(s) and the like.

Figure 5:
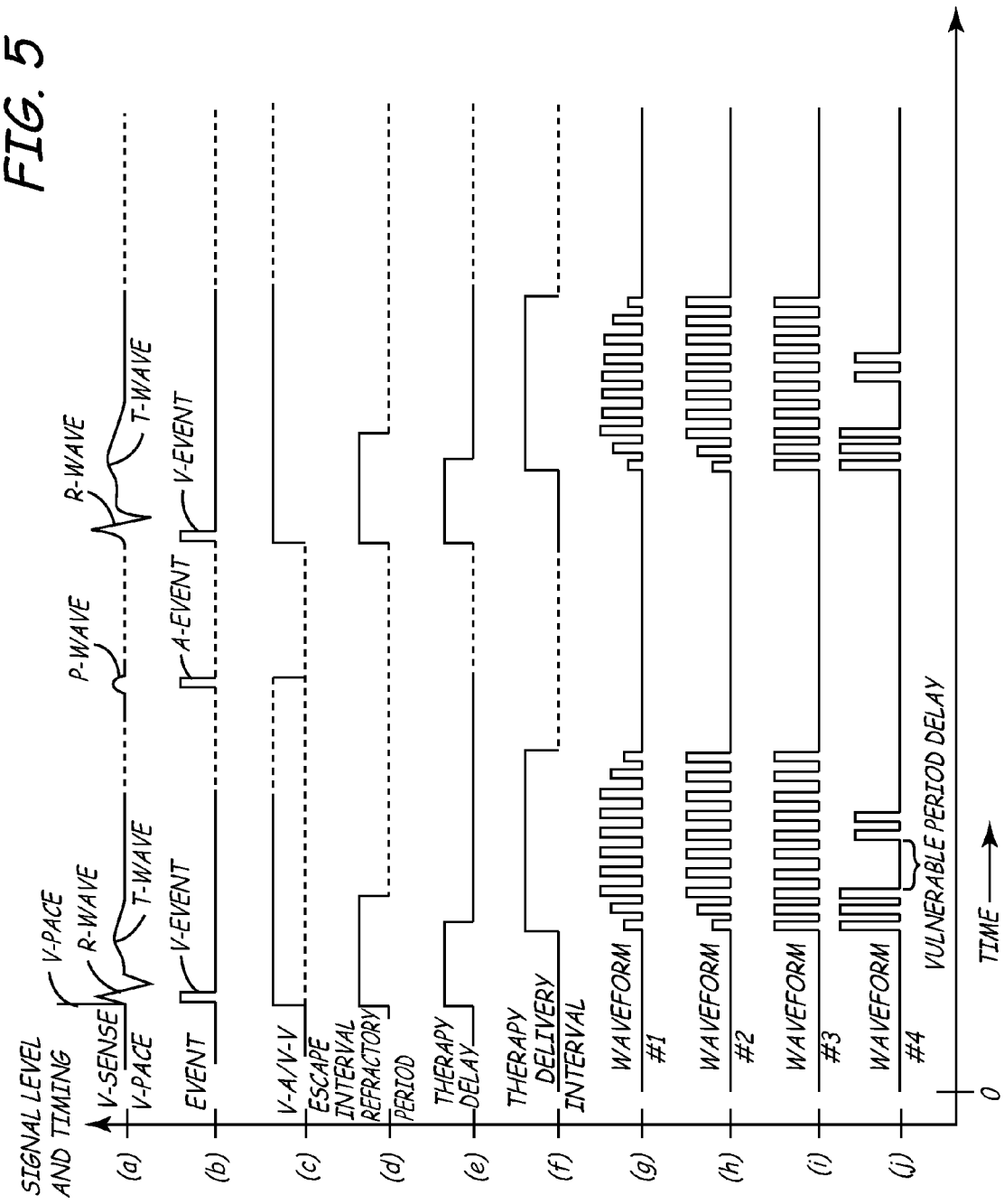
FIG. 5 depicts the delivery of therapeutic RPS stimulation, particularly, pacing energy pulse trains commenced during the refractory period of the heart and continuing for a RPS delivery interval.

Turning to FIG. 5, the timing diagram illustrates the timing of delivery of stimulation to a heart chamber in relation to a timed interval from a sensed or paced event as well as alternative pulse waveforms of the RPS/NES stimulation. In accordance with one aspect of the present invention, a therapeutic stimulation delay illustrated in tracing (e) is timed out from a sensed or paced event (e.g., the illustrated V-EVENTs) that for NES is shorter than the refractory period of the heart persisting from the sensed or paced event. A stimulus pulse train is delivered to the atria and/or ventricles in the depicted therapy delivery interval of tracing (f) commencing after time-out of the delay so that for NES therapy delivery at least the initial pulse(s) of the pulse train fall within the end portion of the refractory period. The pulses for RPS therapy delivery is intended to be supra-threshold in nature, that is, of sufficient energy to depolarize the heart when they are delivered in the non-refractory period of the heart cycle so that the heart is captured by at least one of the RPS pulses falling outside the refractory period. The initial pulses delivered during the refractory period can also potentiate the heart. For simplicity of illustration, the tracings (f)-(j) are expanded in length, and the depolarization of the heart that they cause is not depicted in tracing (a). The amplitude and number of refractory interval pulses and RPS pulses in each therapy pulse train and the spacing between the pulses may also differ from the illustrated tracings (g)-(j).

The ventricular sense or pace event detected in tracing (b) also triggers the timing out of an escape interval in tracing (c) which may be terminated by the sensing of a subsequent atrial or ventricular event, depending on the operating mode of the system. The first depicted sequence in FIG. 5 shows the full time-out of the escape interval in tracing (c), the refractory period in tracing (d), and the therapy delay and delivery intervals in tracings (e) and (f). The therapy delay and therapy delivery intervals can be derived as a function of an intrinsic V-V or V-A escape interval derived by measuring and averaging intervals between intrinsic ventricular and/or atrial sense events or paced events. The therapy delay can also be determined from a measurement of the Q-T interval. As illustrated, the therapy delay in tracing (e) delays delivery of the therapy pulse train until the QRS complex ends or about 40-60 ms after the V-EVENT well before the start of the vulnerable period of the heart which occurs near the end of the T-wave. The therapy delivery interval is timed to time-out well before the end of the previously derived V-V or V-A escape interval, but is extended for ease of illustration of the pulse trains in tracings (f)-(j).

The therapy stimulation energy is delivered in the form of a burst of X constant or variable energy stimulation pulses separated by a pulse separation interval between each pulse of the burst. All of the pulses can have the same amplitude and energy as shown in waveform 3 of tracing (i). Or the leading and/or trailing pulses of the pulse train can have ramped amplitudes similar to the waveforms 1 and 2 illustrated in tracings (g) and (h). In tracings (g) and (h), the ramp up leading edge amplitudes of a sub-set of the pulses of the burst are shown increasing from an initial amplitude to a maximum amplitude. In tracing (g), the ramp down trailing edge amplitudes of a further sub-set of the pulses of the burst are shown decreasing from the maximum amplitude to a terminating amplitude.

Alternatively, the initial set of pulses delivered during the refractory period can have a higher pulse amplitude or width as shown by waveform 4 illustrated in tracing (j). The high energy pulses delivered during the refractory period can enhance potentiation during subsequent heart cycles. Tracing (j) also illustrates alternative numbers and spacing of the pulses of the pulse train, and it will be understood that this embodiment can also employ the number of pulses and pulse spacing of waveforms 1-3.

In addition, it may be desirable to avoid delivering any therapy pulses in the vulnerable period of the heart near the end of the T-wave, particularly if high energy pulses are delivered during the refractory period. Tracing (j) also illustrates a vulnerable period delay between the high energy pulses delivered during the refractory period and the lower energy RPS pulses to avoid delivering any pulses during the vulnerable period of the heart. It would also be possible to lower the pulse energy of the pulses delivered later in the refractory period.

The therapy delivery capability is preferably implemented into a system that may include conventional pacing therapies and operating modes as well as cardioversion/defibrillation capabilities or as a stand alone system for simply providing pulse therapies to effect potentiation of myocardial cells between sensed PQRST complexes shown in FIG. 5.

Detailed Description of Atrial Coordinated Pacing Per the Invention.

Figure 6:
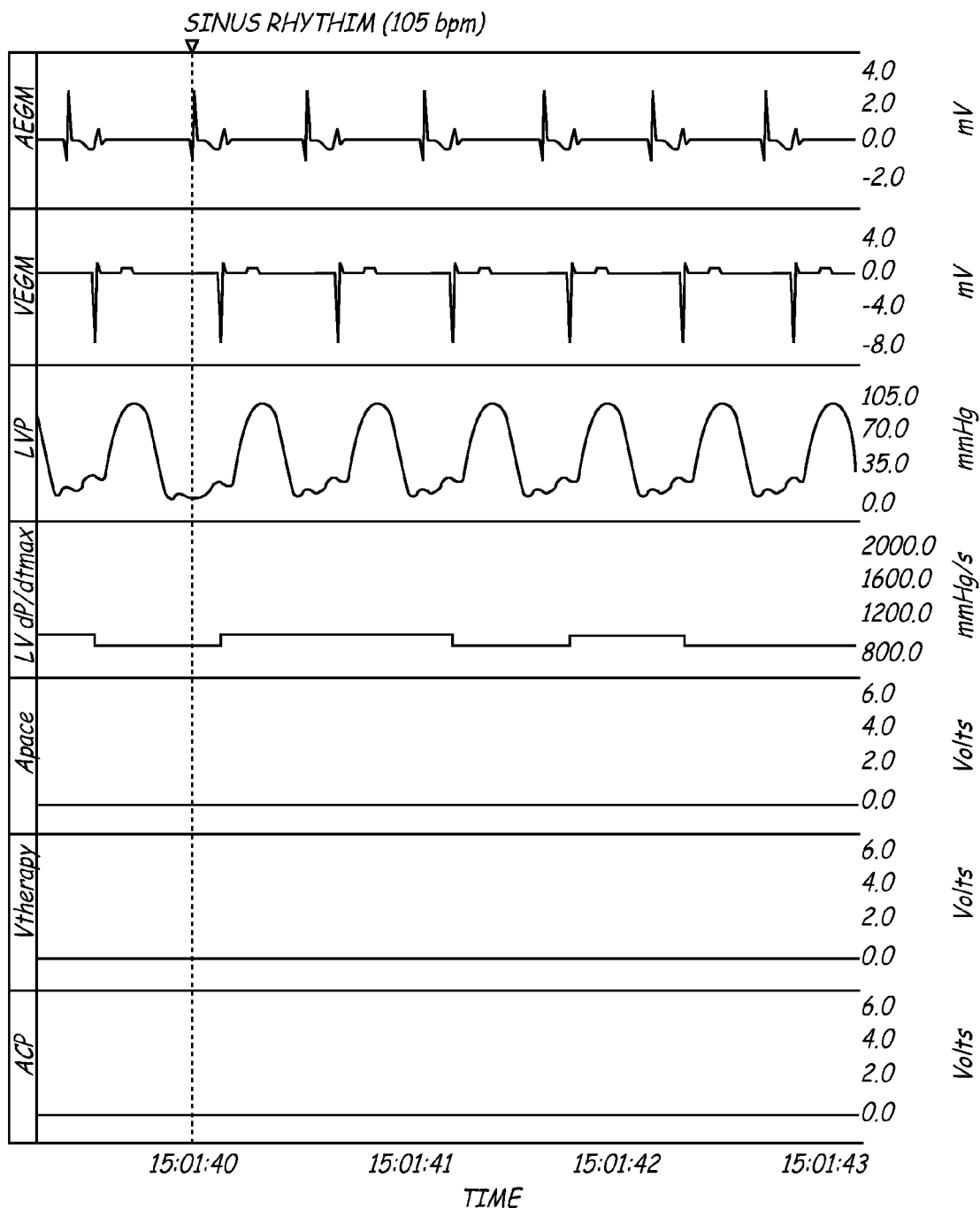
FIG. 6 is a set of traces representing physiologic and therapy activity according to the present invention.

FIG. 6 illustrates untreated chronic HF dysfunction with a rapid sinus rhythm (100 bpm) in an ambulatory model of chronic HF. In FIG. 6, regular atrial and ventricular electrograms (AEGM and VEGM) are illustrated, and a measurement of an index of contractile function (LV dP/dtmax) is shown which is derived from LV pressure (LVP). In FIG. 6 the valued of LV dP/dtmax is shown to be about 900 mmHg/s.

Figure 7:
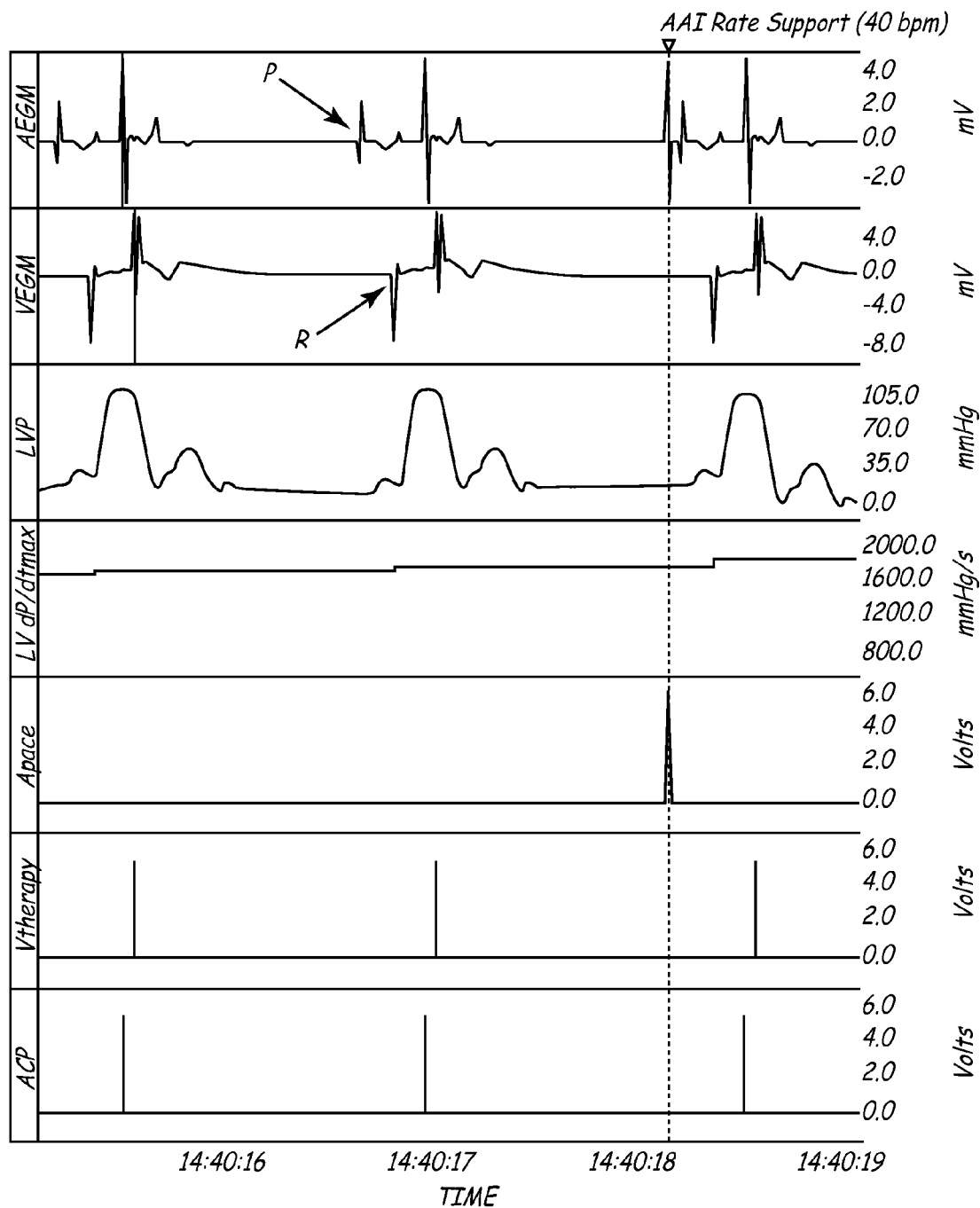
FIG. 7 is a set of traces representing physiologic and therapy activity according to the present invention.

FIG. 7 illustrates HF dysfunction treated with RPS therapy and atrial coordinated pacing (ACP) according to the present invention. In FIG. 7, the subject with chronic HF is continuously treated with ventricular RPS therapy (channel marked Vtherapy) and atrial coordinated pacing ACP (channel marked ACP). The result is a stable rhythm at a lower rate (around 50 bpm) with sustained contractile enhancement (LV dP/dtmax is improved to about 1800 mmHg/s). It can be seen that occasionally, when the intrinsic atrial rate drops, an atrial pace event occurs to initiate a cardiac cycle (see Apace event aligned with the vertical line labeled "AAI rate support" (at the right of FIG. 7). One result of RPS therapy and ACP therapy is a slower rhythm with enhanced mechanical function occurring on the portion of the cardiac cycle with intrinsic AV conduction and natural ventricular depolarization. This therapy regimen causes a forced deceleration of the cardiac rhythm. This type of stimulation therapy also appears suitable for HF patients having intact AV conduction that suffer from SVT (supraventricular tachyarrhythmia) as will be further described and illustrated with respect to FIG. 36 (below).

Figure 8:
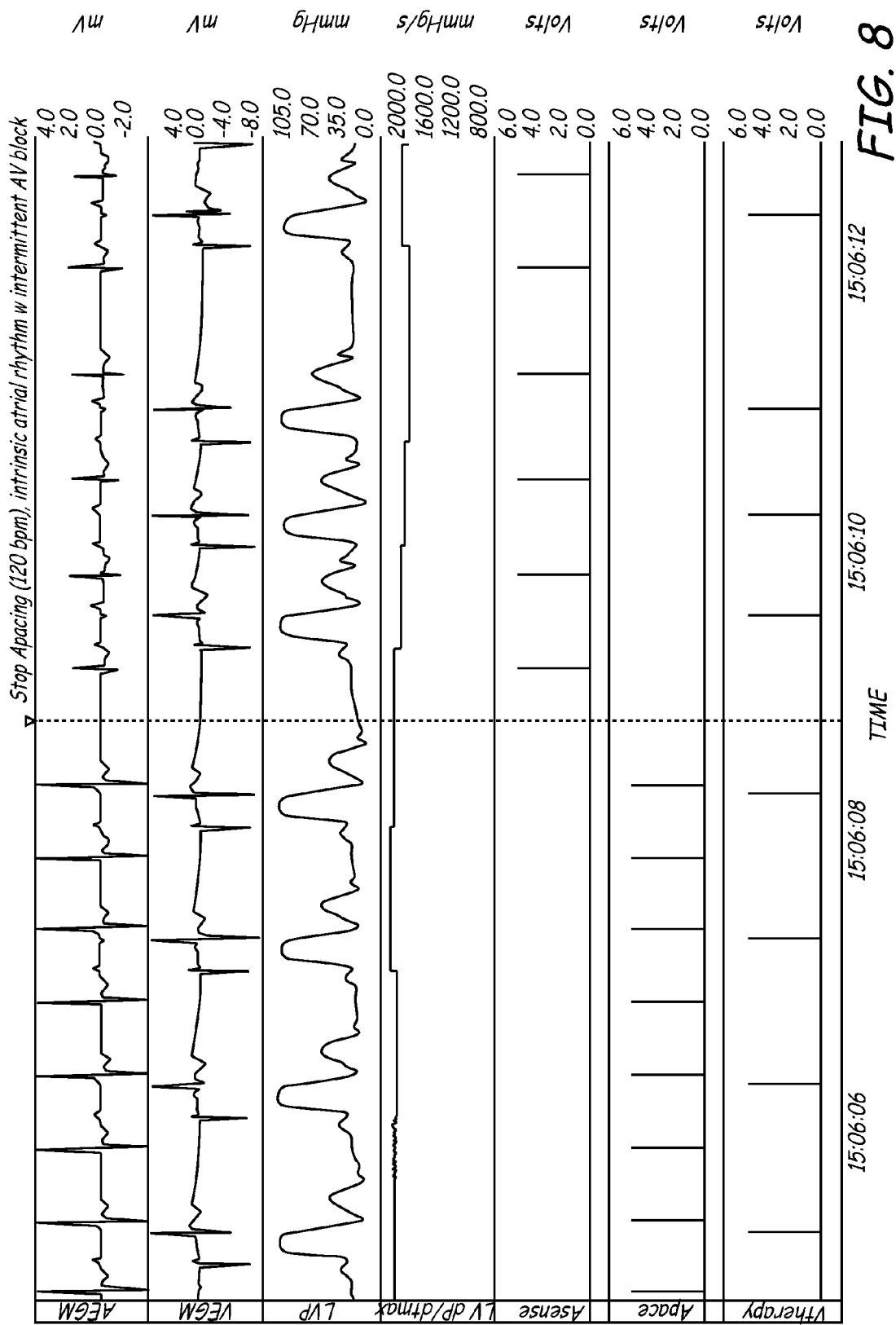
FIG. 8 is a set of traces representing physiologic and therapy activity according to the present invention.

Referring now to FIG. 8, rhythm irregularities are depicted during RPS therapy (without ACP). In the left portion of FIG. 8, HF dysfunction is treated with RPS therapy and a form of ACP consisting of AAI pacing at 120 bpm with 2:1 AV block. In the right portion of FIG. 8, HF dysfunction is treated with RPS therapy without AAI pacing. Although it can be appreciated that contractility remains improved (about 1900 mmHg/s), variations in refractoriness and intrinsic intervals commonly result in intermittent 1:1 and 2:1 AV conduction (seen at right of FIG. 8). The heart tissue is not guaranteed sufficient time in diastole for good filling, coronary flow, and ion flux stabilization. As a result, the peripheral pulse rate is variable, mechanical enhancement is less consistent, and the heart more prone to arrhythmias and metabolic intolerance.

Figure 9:
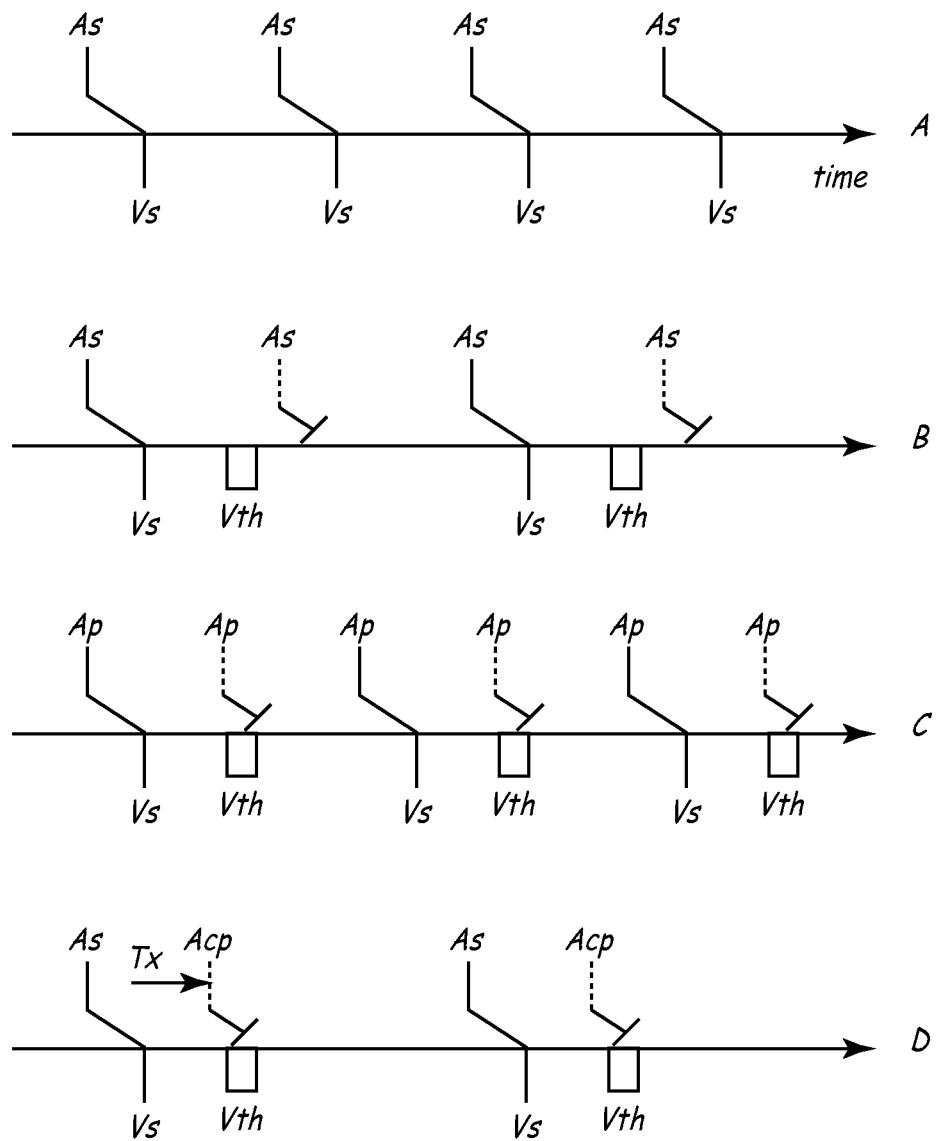
FIG. 9A through 9D are simple exemplary timing diagrams of various embodiments of the therapy delivery according to the present invention.

FIG. 9A-9D is a schematic of atrial coordinated pacing (ACP) from the perspective of an implantable medical device, such as an ICD or pacemaker. In FIG. 9A, a normal sinus rhythm is depicted in which each atrial instrinsic depolarization (denoted As for atrial sense event) conducts to the ventricles and produces an intrinsically conducted ventricular depolarization (labeled Vs for ventricular sense event). If the intrinsic atrial rate is too low, atrial pacing (denoted Ap) may substitute for atrial sense events shown. With respect to FIG. 9B, introduction of ventricular stimulation therapy pulses (either RPS alone or combined RPS and NES—denoted Vth) occurs and the ventricles become refractory a second time. As a result, a 2:1 conduction pattern may arise in which every other atrial sense event is blocked. This pattern is often unstable (see FIG. 8 above) and may result in effective ventricular rates that are too slow (brady) or too fast (tachy).

With respect to FIG. 9C, which depicts a simple form of ACP, the atria are paced at a rate faster than the intrinsic rate and the 2:1 block is regularized. This approach helps when the result of the case depicted in FIG. 9B was an effective ventricular rate that was too slow or too irregular, but does not allow the subject's physiology to set heart rate, paces the atrium frequently, and may result in an excessive heart rate.

With respect to FIG. 9D, which depicts a preferred implementation of ACP, the atria are paced for the purpose of coordination (denoted "Acp") after the ventricular sense event and around the same time as the Vth pulse or pulses. The ACP pace events do not conduct to the ventricles but reset the sinus node. Thus, the next atrial sense event occurs at a time governed by physiologic demand. The resulting "potentiated" beats are thus advantageously preceded by adequate filling time, better coronary flow, and more time for myocye ion fluxes to normalize.

Of course, as is well known in the art, atrial pacing may be employed if the intrinsic atrial rate drops too low (see FIG. 7—above) and maintain the advantages discussed. Furthermore, if AV or ventricular conduction is impaired, ventricular pacing at an appropriate AV interval may also be employed. This may take the form of single or multiple site (e.g. biventricular) pacing.

For TCP or transthoracic pacing such as employed with an AED, although atrial sensing is not readily available (nor is atrial pacing) ACP as illustrated by FIG. 9D can still be performed. To practice such ACP, a TCP therapy pulse triggered from a sensed R-wave (or pacing pulse) would induce depolarization in both atria and ventricles simultaneously and achieve RPS and ACP according to the present invention.

As is known in the art, timing and delivery of ACP pulses are preferably under microprocessor control, such as depicted in the system diagrams of FIG. 3A and FIG. 3B. Also, such timing parameters are programmable and may be adjusted or modified by a clinician.

With general reference to FIG. 6 through FIG. 9, it should be appreciated that ventricular therapy, denoted Vth, includes RPS and optionally nonexcitatory neurostimulation (NES). The determinants of timing and amplitude of the Vth pulse or pulses have been discussed previously in the '631 disclosure and elsewhere in this invention disclosure. Intervals from the preceding Vs or Vp event are chosen to yield the desired effects (excitatory or nonexcitatory) and amplitude of potentiation (RPS). Furthermore, the choice of ACP timing to implement safe and physiologic enhancement of cardiac function is also important. If the Vth therapy pulse is vetoed by safety rules or other reasons or does not capture, the ACP pulse is withheld. When excitatory ventricular therapy is discontinued, so too is ACP. If this is not done, there results a form of pacemaker mediated tachycardia (PMT). Unless potentiation is intended to come from conduction of the ACP pulse's depolarization, the goal of ACP is to guarantee atrial depolarization and AV block. These considerations result in bounds for ACP timing that will be discussed for the case of therapy delivered every cardiac cycle.

For example, let X represent the time from the potentiated Vs (or Vp) to the scheduled delivery of ACP. Let Y similarly represent the time from the potentiated Vs (or Vp) to the scheduled delivery of Vth. These rules behind calculation of the value of Y are described in the '631 disclosure, and in the present patent disclosure with respect to discussion and illustrations regarding feedback control, the safety lockout rules, and the identification and determination of refractory interval. The value of X must be larger (i.e., longer) than the A-A refractory period (which is often approximately 200-300 ms). The value of X must also be chosen such that the resulting depolarization passes the AV node or ventricle while in a refractory state. Let $R_V$ denote the V-V refractory period and $R_A$ denote the A-A refractory period. Further let AV denote the AV conduction delay (that is the time from an Apace to a Vsense event, less any delays associated with sensing itself). Then X must satisfy the following pair of inequalities:

$$X > R_A \text{ and } Y-AV < X < Y-AV+R_V$$

Experience has shown values of X in the range of 150 to 200 ms to satisfy both inequalities and yield the desired effects. This generally places ACP shortly before excitatory Vth pulses. The reader should note that ACP is subject to the same safety veto rules as Vth (discussed in relation to safety lockout rules section of this patent disclosure) but faces an additional challenge. That is, if the Vth pulse amplitude(s) is sub-threshold or entirely within the refractory period, no potentiation results. Although the arrhythmia risk is essentially zero, the subject is deprived of the benefit of RPS therapy. However, if ACP is delivered above threshold in this setting, this could raise the ventricular rate by conducting to the ventricles. The resulting Vsense initiates another ACP and establishes a PMT with cycle length of X+AV. The present invention therefore incorporates an additional ACP lockout rule that ends this type of PMT after a single beat. This lockout rule requires that if there is no atrial event (sense or pace) over the previous cardiac cycle (from Vsense to Vsense) or in a sufficient interval, then the ACP is selectively vetoed for the next N cardiac cycles and evidence sought of extrasystole capture.

Detailed Description of Non-Excitatory Neurostimulation.

Figure 10:
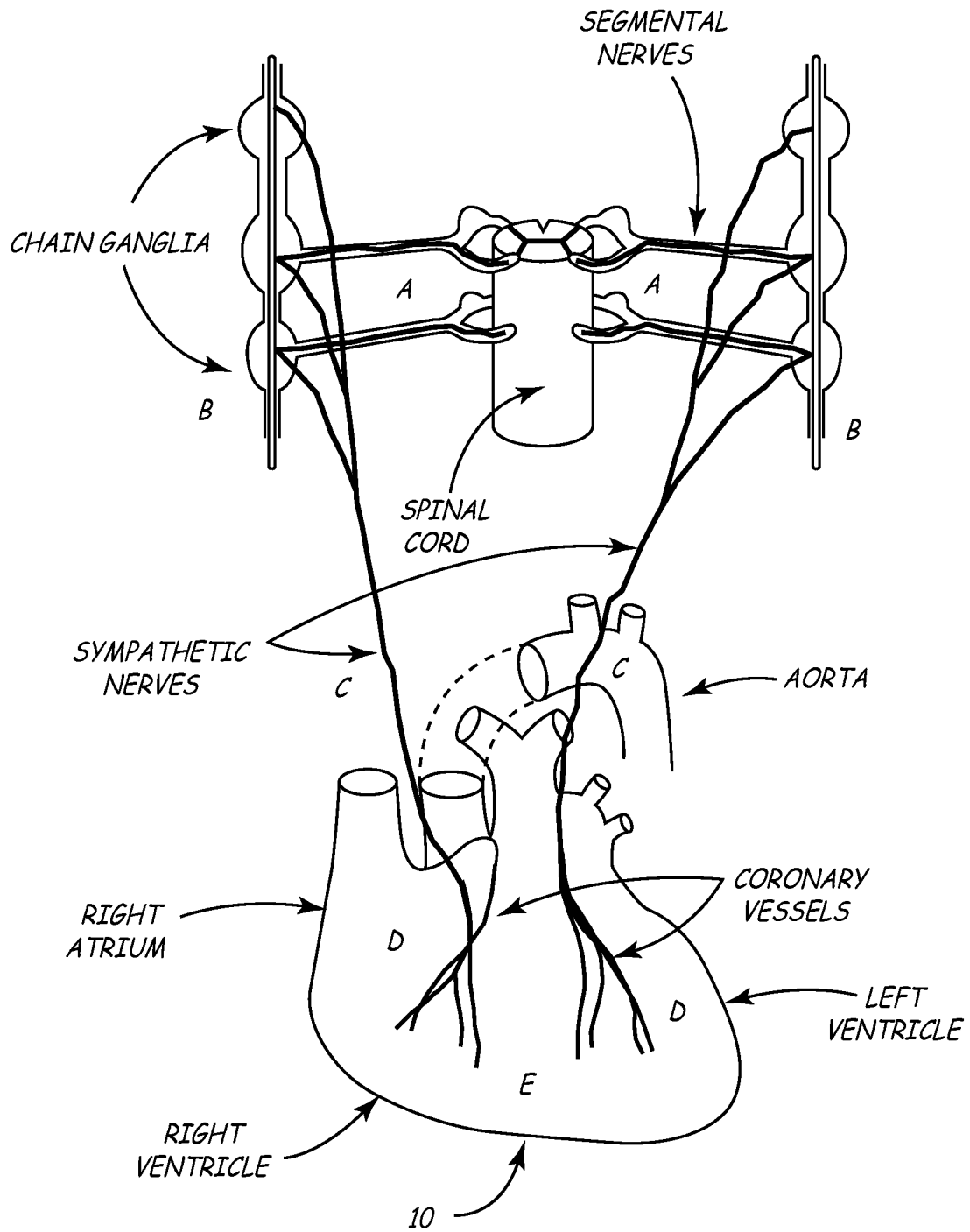
FIG. 10 is a perspective view with portions exploded (and with some portions not depicted) of a heart and related sympathetic nerves which may be advantageously stimulated according to certain embodiments of the present invention.

Now turning to FIG. 10 in which sympathetic innervation of the heart and electrode locations for nonexcitatory stimulation (NES) is depicted in a partially exploded perspective view with portions removed for ease of inspection. Significant elements in FIG. 10 are identified as the following: spinal cord, cervical and thoracic segmental nerves (collectively denoted by the letter "A"), cervical and thoracic chain ganglia (up and down near the vertebral bodies at back of thorax (denoted with the letter "B"), autonomic nerves traveling through the thorax and mediastinum toward great vessels and the heart 10 and including the ansa subclavia (denoted with the letter "C"), various cardiac nerves often traveling near coronary vessels (denoted with the letter "D"), and cardiac nerves in the myocardium (denoted with the letter "E"). Electrodes (such as depicted in FIG. 2) may be positioned anywhere along these pathways to direct electrical stimulation current to these sympathetic nerves and avoid painful stimulation of other nerves or organs and avoid pacing the heart 10. Alternatively, subcutaneous electrodes such as the can electrode or other subcutaneous patch electrodes may be employed to stimulate broadly regions A-E and reserved for severe dysfunction including cardiogenic shock and electromechanical dissociation (EMD) or pulseless electrical activity (PEA). Furthermore, subcutaneous patch, pad electrodes or paddle electrodes may be similarly employed to direct electrical current to related sympathetic neural tissue in accordance with this aspect of the present invention.

Figure 11:
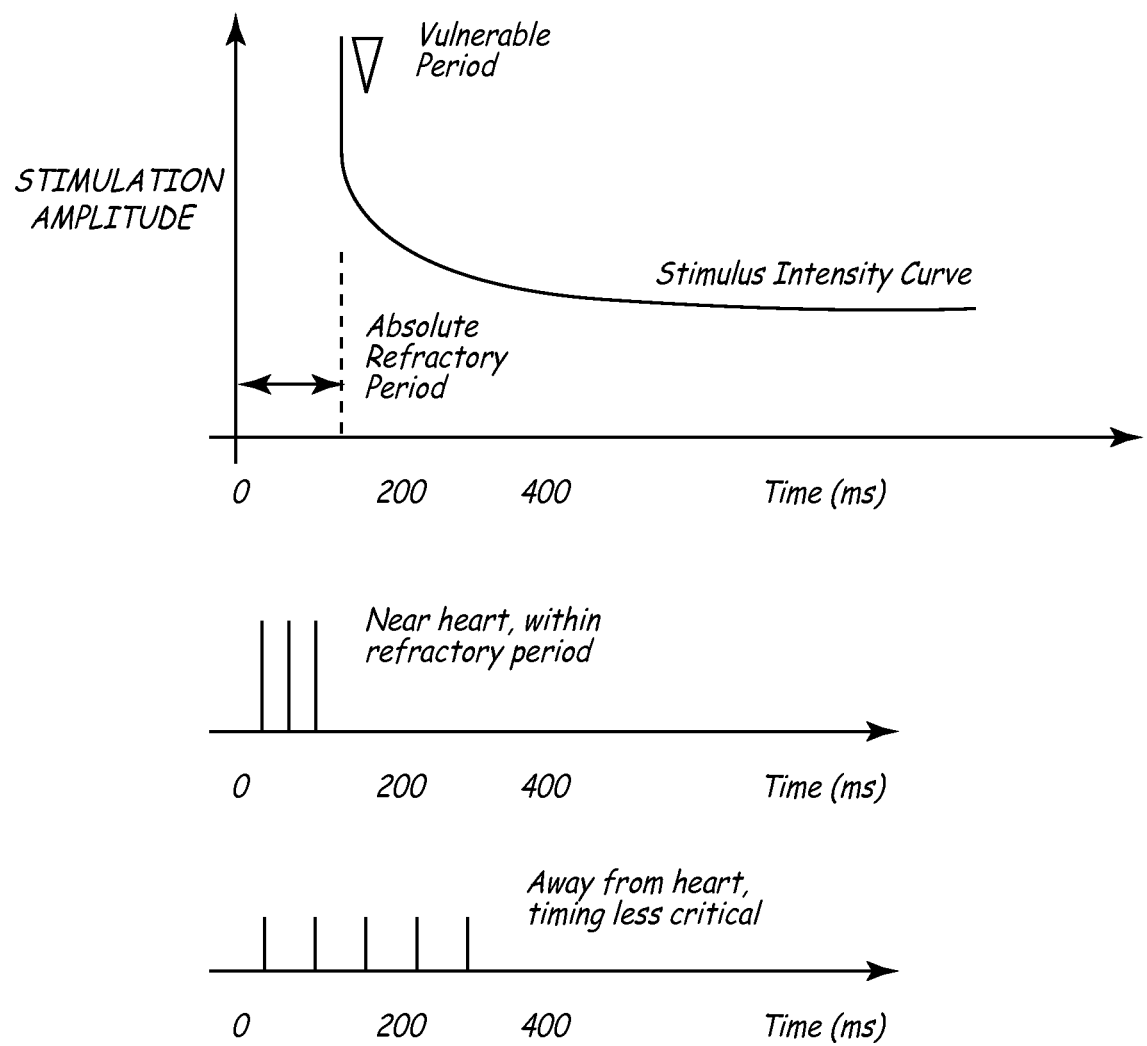
FIG. 11 is a depiction of neurostimulation timing for electrodes disposed near the cardiac tissue and relatively remotely from the cardiac tissue of a patient.

Now turning to FIG. 11 which depicts neurostimulation and the cardiac refractory period, it can be seen that a stimulation threshold curve of cardiac muscle and the electrode location for nonexcitatory neurostimulation govern stimulation pulse timing. Adjacent to the heart where stimulation could cause capture, the NES pulses are delivered during the refractory period and/or remain subthreshold (i.e., below a threshold magnitude). Further from the cardiac tissue, the stimulation pulses may have different amplitude and may be more widely spaced.

Figure 12:
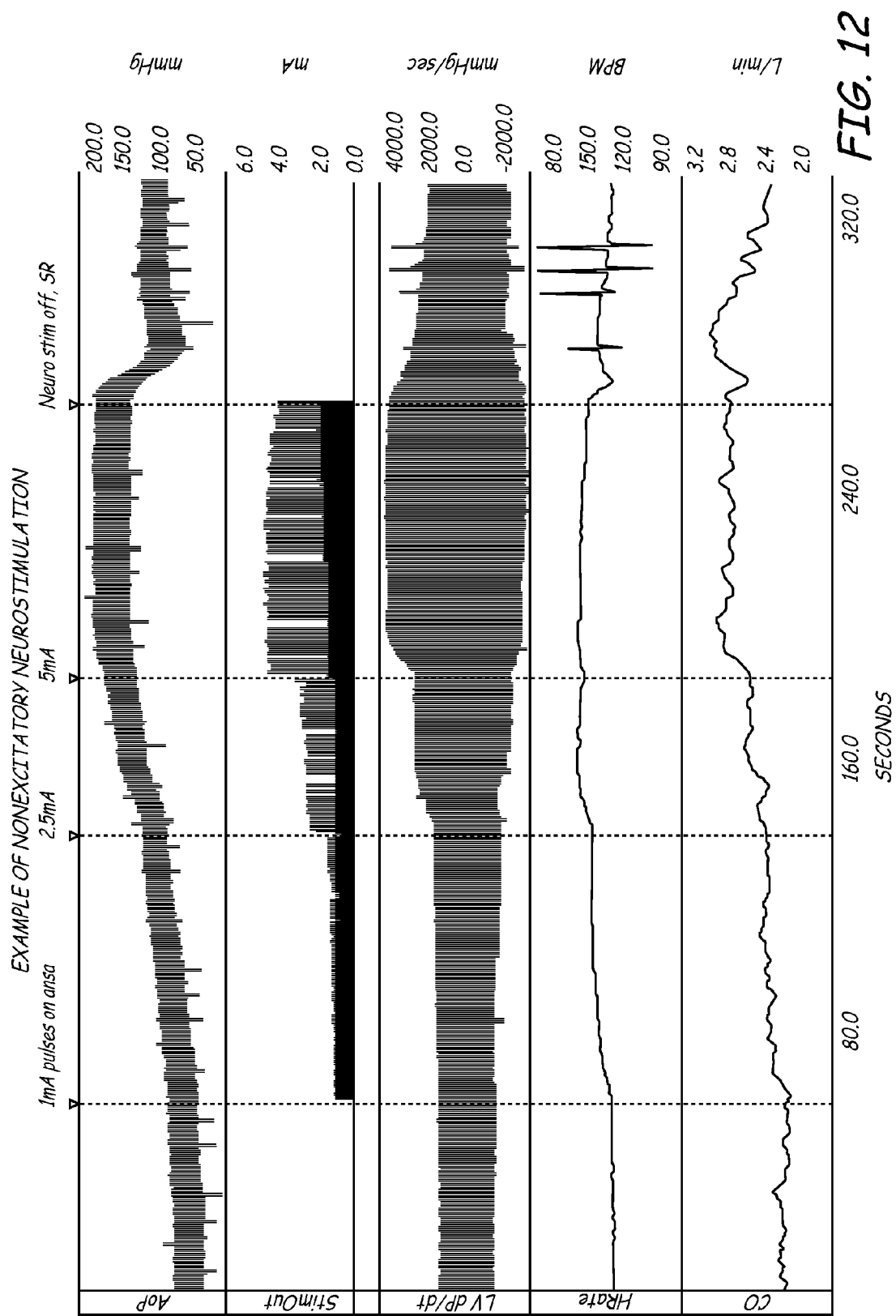
FIG. 12 is a set of traces representing physiologic and therapy activity according to the present invention.

FIG. 12 is a diagram illustrating an example of NES therapy delivery. This diagram illustrates the effects of stimulating sympathetic nerves near the heart with increasing amounts of current (1, 2.5, and 5 mA, respectively). Such NES stimulation during the refractory period results in a dose dependent increase of aortic blood pressure (AoP), contractility (LV dP/dt), heart rate, and cardiac output. The magnitude of the response may be similarly controlled by adjusting the duration and/or number of pulses in the NES pulse train. The NES therapy timing and stimulus parameters are preferably controlled by a microprocessor or hardware and programmable with input values determined by algorithms or clinicians, such as depicted in the system diagrams of FIG. 3A and FIG. 3B.

Detailed Description of Safety Lockout Rules.

Figure 13:
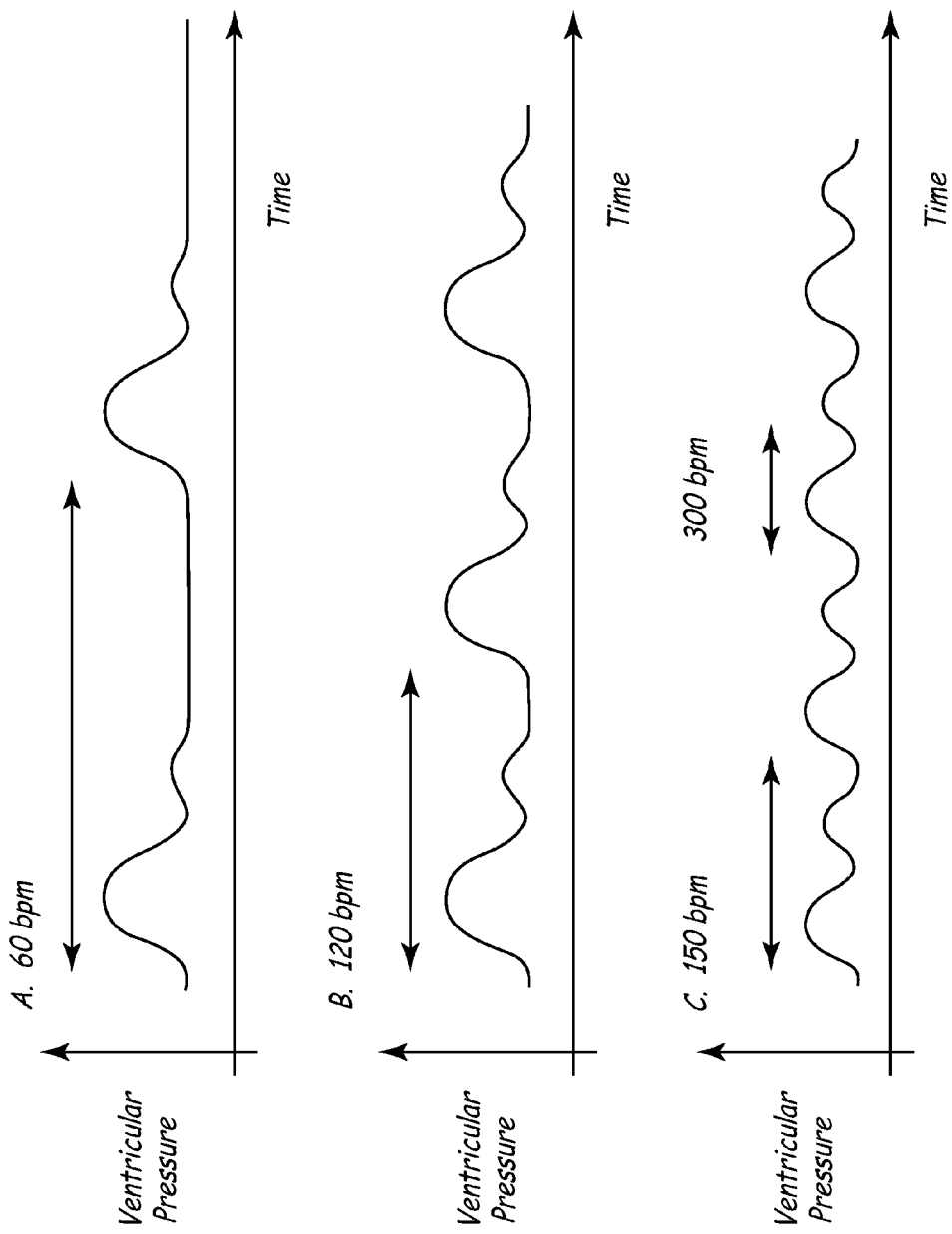
FIG. 13 is a set of three X-Y plots representing physiologic and therapy activity according to the present invention.

FIG. 13A through 13C illustrate the consequences of RPS stimulation during a tachycardia event. The inventors have discovered that it is preferable, if not absolutely necessary, to cease delivery of excitatory RPS stimulation therapy during tachycardias. In the condition depicted in FIG. 13A, the ventricular mechanical rate is low (60 bpm), the amplitude of the potentiation is large, and there is sufficient time in diastole for ventricular filling. In the condition depicted in FIG. 13B the heart rate has effectively doubled (i.e., increased to 120 bpm), and while the amplitude of potentiation remains large the diastolic time is shorter. In the condition depicted in FIG. 13C, the heart rate is even higher (i.e., at about 150 bpm) and the extrasystole encroaches severely on the cardiac cycle's time in diastole. Furthermore, at these high heart rates RPS potentiation diminishes. The RPS stimulation transforms the 150 bpm tachycardia to a ventricular tachycardia with mechanical alternans and an effective rate of 300 bpm. Heart rates this high are poorly tolerated and will further contribute to cardiac dysfunction, heart failure decompensation, and predispose a person subjected to such an effective heart rate to VT or VF.

Figure 14:
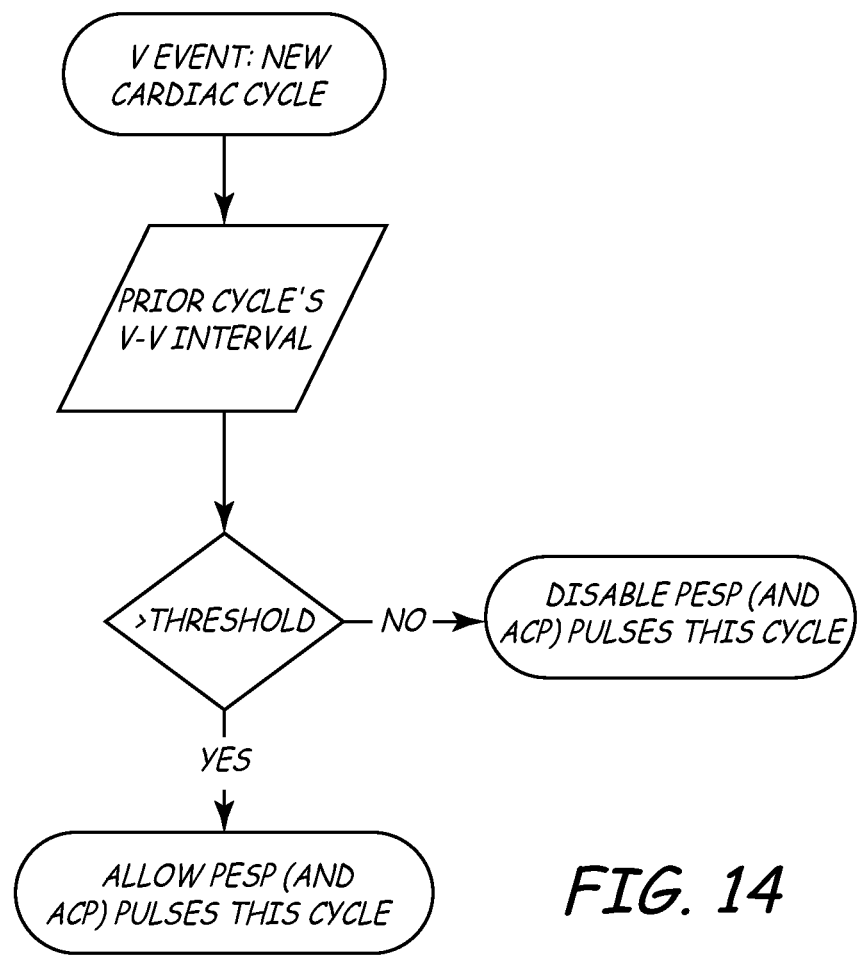
FIG. 14 is a flow chart depicting an aspect of the present invention.

Referring now to FIG. 14, a flow chart for a safety lockout rule for application of excitatory RPS stimulation is depicted. It can be appreciated that each new cardiac cycle begins with a ventricular event (Vevent) that is either a Vpace or Vsense. The safety lockout rule has veto power over the decision to deliver excitatory RPS stimulation to the ventricle and possibly atrial coordinated pacing (ACP) during this cycle. If the prior V-V interval is greater than a threshold value, RPS and/or ACP pulses are enabled for this cycle. Should the V-V interval be too short, stimulation therapy is aborted. This prevents stimulation therapy from further adding to the arrhythmic potential of an intrinsic premature ventricular contraction (PVC). Stimulation with a short coupling interval, particularly if immediately following other short intervals is significantly pro-arrhythmic and is, of course, to be avoided. The safety lockout rule also prevents application of excitatory therapy during various tachycardias including sinus tachycardia, supraventricular tachycardia (SVT), ventricular tachycardia (VT), or ventricular fibrillation (VF). The threshold used may either be a fixed value or derived from other hemodynamic or electrogram based parameters and is typically 400-600 ms. The safety lockout rules may operate using a variety of timing schemes which are microprocessor or hardware controlled and programmable with input values determined by algorithms or clinicians, such as depicted in the system diagrams of FIG. 3A and FIG. 3B.

As set forth in the '956 application, the device may operate by withholding delivery and not initiating delivery of the extra-systolic stimulation therapy if at least one unscheduled depolarization occurs. The device may operate by ceasing delivery of delivery and not initiating delivery of the extra-systolic stimulation therapy in the event that the unscheduled cardiac activity begins an accumulating tachycardia evidence counter of an on-going tachycardia episode or until such time as either the evidence counter reaches a preset threshold and a tachycardia episode is declared or the evidence counter is reset to a nominal or null value. The unscheduled depolarization may comprise a premature atrial or a premature ventricular contraction.

Detailed Description of Start-Stop Rules.

Figure 15:
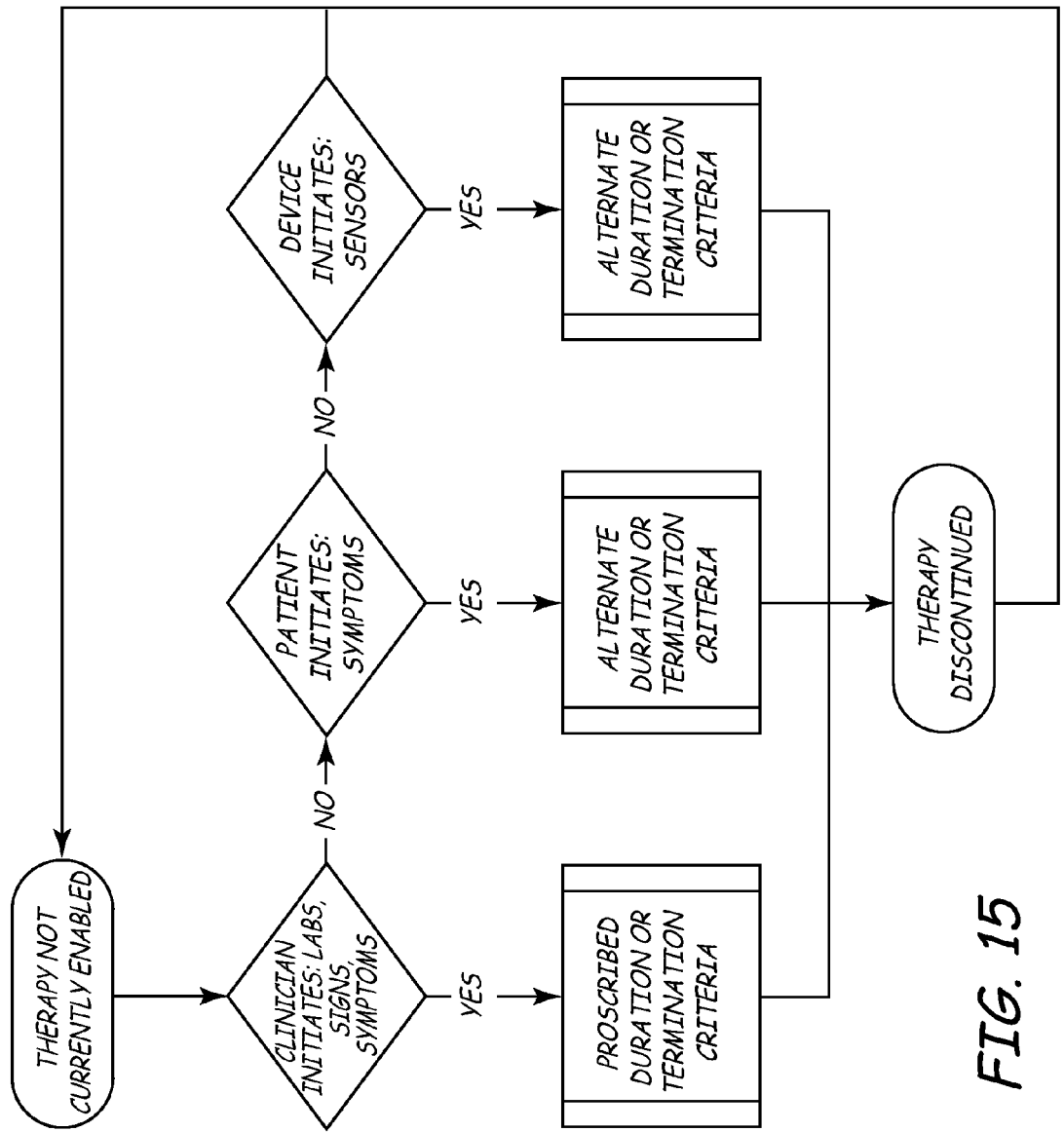
FIG. 15 is a flow chart depicting another aspect of the present invention.

Referring now to FIG. 15, which is a top level flow chart governing initiation and termination of stimulation therapies according to the present invention. If therapy is not currently enabled, therapy can be initiated by a clinician, the patient, or the device. The clinician is able to preempt an assessment by the device or patient to begin stimulation therapy based on consultation with the patient, signs or symptoms of cardiac dysfunction, or lab results. If begun in this manner the therapy may have a duration and termination criteria different from patient or device initiated therapy. Similarly, the patient, as a result of symptoms or anticipated exertion may preempt the device and begin therapy. Finally, the device may automatically begin therapy based on preprogrammed time of day or due to sensor signals, including electrograms, hemodynamic, activity sensor signals, and other physiologic sensor signals. Therapy may be discontinued by clinician command, patient request, or device based criteria that include sufficient therapy duration and sensor assessment of sufficient benefits or risks.

Figure 16:
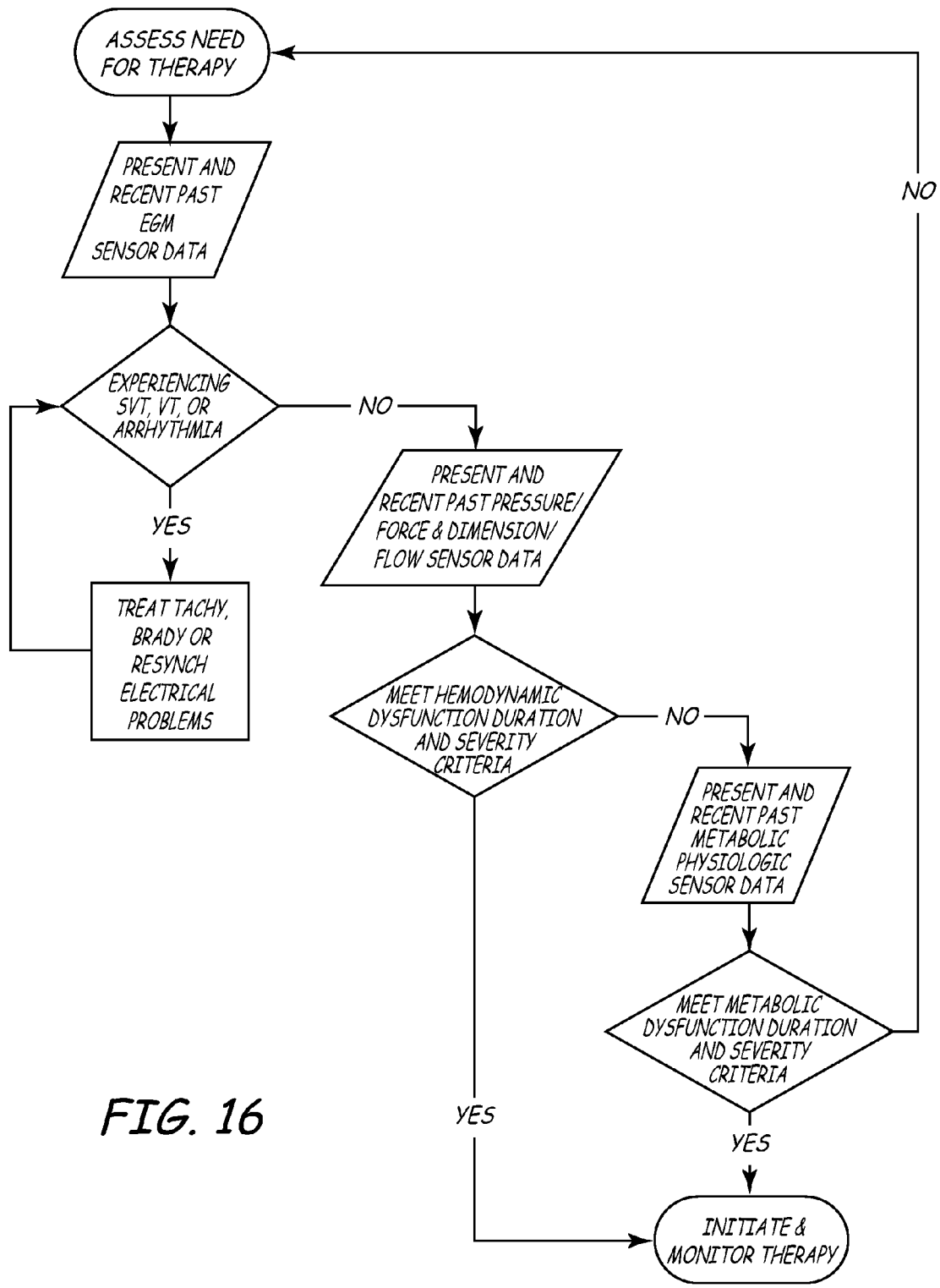
FIG. 16 is a flow chart depicting yet another aspect of the present invention.

In FIG. 16, which is a more detailed flow chart of automated sensor-governed initiation of stimulation therapies. Based on electrogram (EGM) sensor signals derived from a patient (both presently and recently), the device first looks for and treats cardiac rhythm problems before moving on to examine other sensor signal data. If the cardiac rhythm appears satisfactory, then hemodynamic sensors such as pressure and flow are employed. If there is sufficient dysfunction and duration, therapy begins. Metabolic or other physiologic sensor severity and duration assessments as well as a pre-scheduled time of day criteria may also initiate stimulation therapies according to the present invention.

Figure 17:
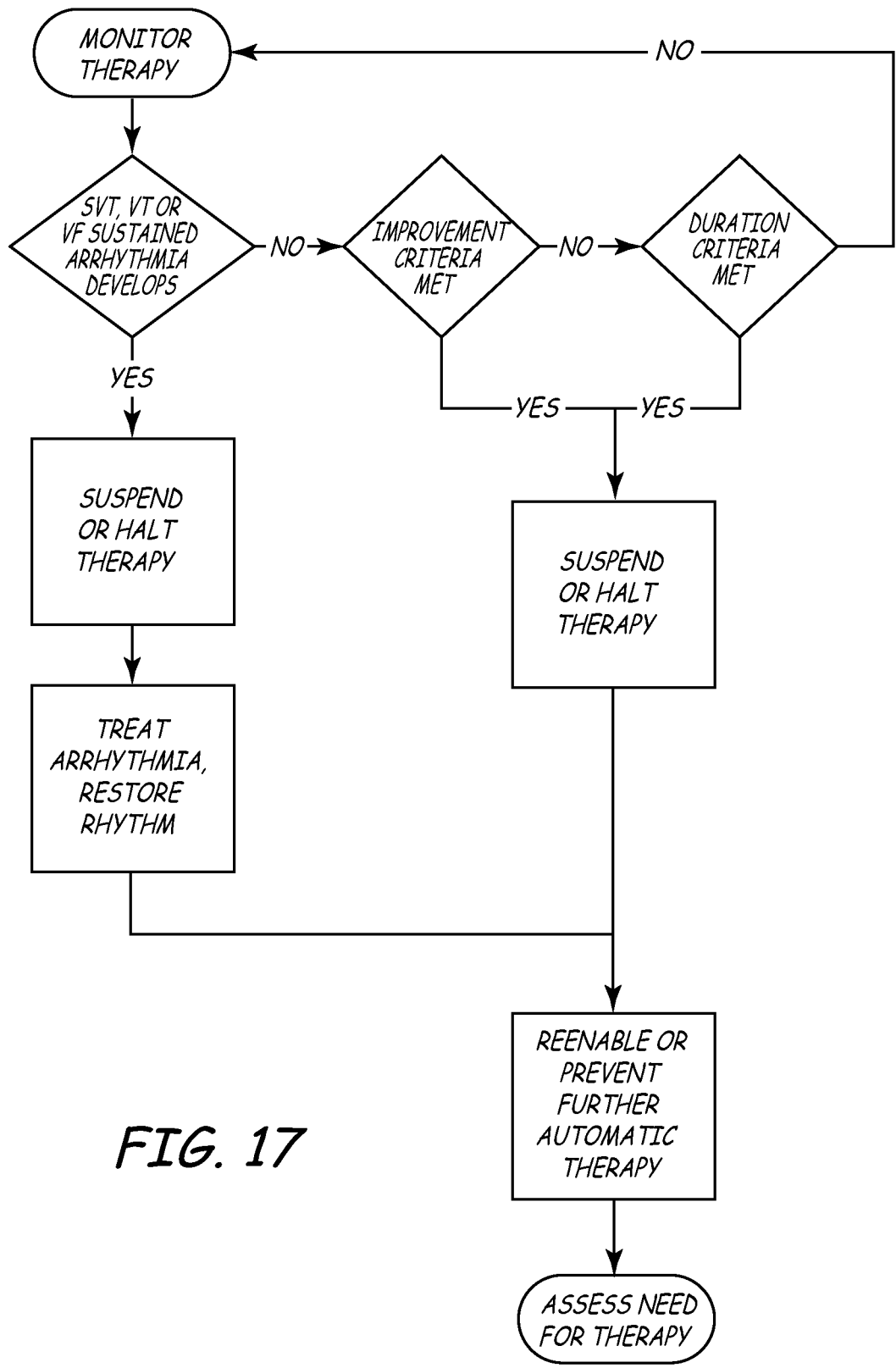
FIG. 17 is a flow chart depicting an additional aspect of the present invention.

With respect to FIG. 17, which is an expanded diagram of suspension or termination of stimulation therapies according to the present invention. If a tachyarrhythmia develops of sufficient rate or duration (e.g., which exceeds a predetermined rate or duration threshold), the therapy is either temporarily suspended or halted altogether and the arrhythmia treated by any of a variety of well-known means such as antitachycardia pacing (ATP), cardioversion, or the like. Upon restoration of a more normal rhythm, the device may or may not re-enable automatic therapy delivery. The device may also readjust its stimulation therapy parameters such as timing and amplitude to achieve a lower arrhythmia risk profile, trading physiologic benefit for arrhythmia risk (on the presumption that the stimulation therapies either caused or predisposed the subject to this arrhythmia). If the rhythm remains satisfactory, the device checks if either duration or combined hemodynamic improvement and duration criteria are met. If so, the therapies are again either temporarily suspended or halted altogether. Automated therapies may be re-enabled after a period of time or left disabled. In order to prevent multiple brief cyclic applications of therapy, the improvement criteria may be different from the initiation criteria to implement a hysteresis-like effect. Therapies may also be disabled upon reaching a fixed number of therapy applications and require an external override to restart.

Figure 18:
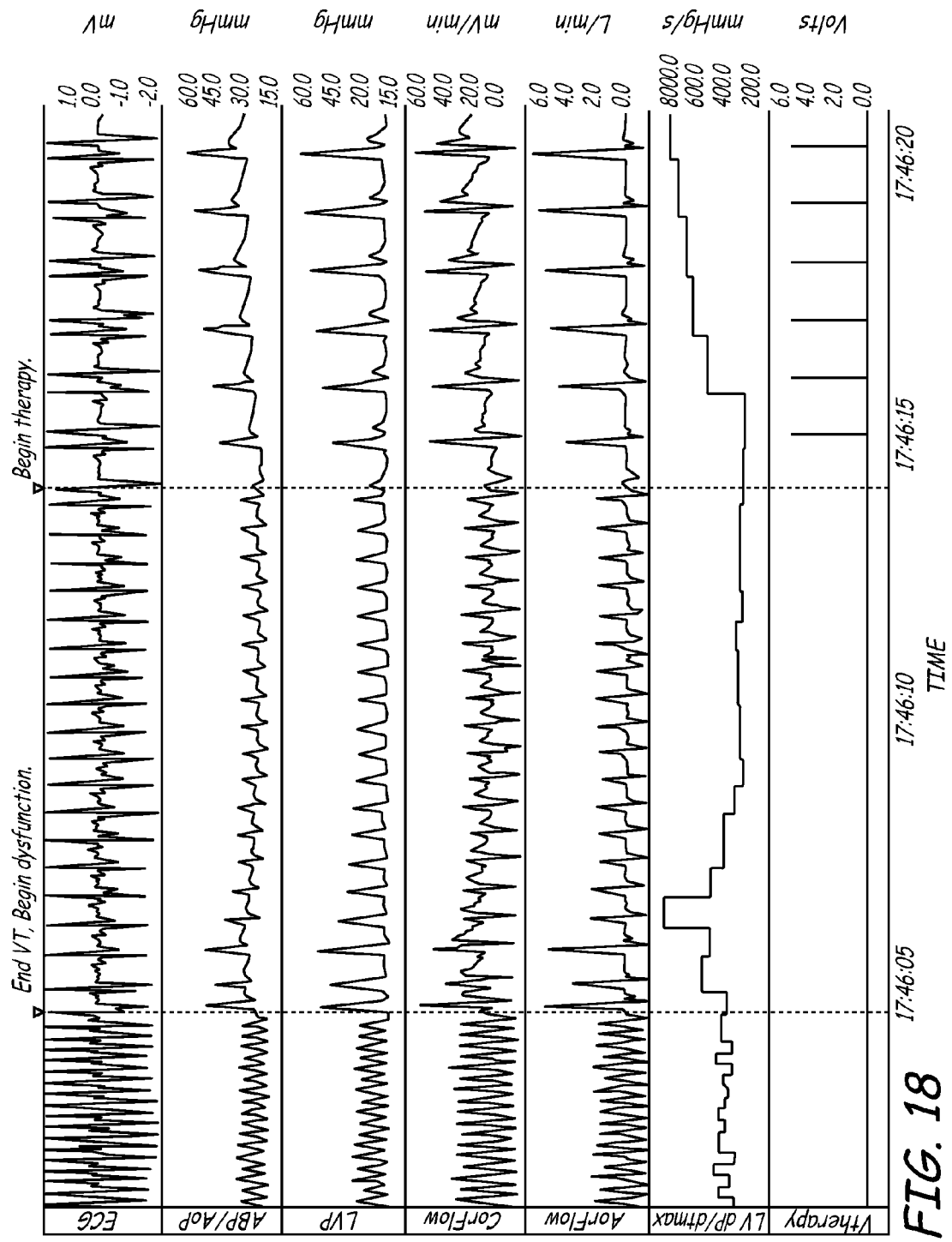
FIG. 18 is a set of traces representing physiologic and therapy activity according to the present invention.

Referring now to FIG. 18, which depicts termination of a tachyarrhythmia and initiation of therapy for cardiac dysfunction, FIG. 18 illustrates some the therapy initiation rules described above. As can be seen with reference to FIG. 18, a tachyarrhythmia is ended at about 17:46:05 and electrogram sensors (here the surface electrocardiogram (ECG) confirm the existence of a reasonable rhythm and rate. However, hemodynamic sensors such as arterial blood pressure (ABP) and left ventricular pressure (LVP) confirm a severe level of dysfunction (e.g. LV dP/dtmax<400 mmHg/s) that is sustained for over 6 seconds and over 12 cardiac cycles. As a result, the decision to initiate stimulation therapies occurs at about 17:46:15. A prompt response of arterial blood pressure, LVP, coronary blood flow, aortic blood flow, and LV dP/dtmax is seen coincident with the application of RPS therapy pulses (Vtherapy).

Figure 19:
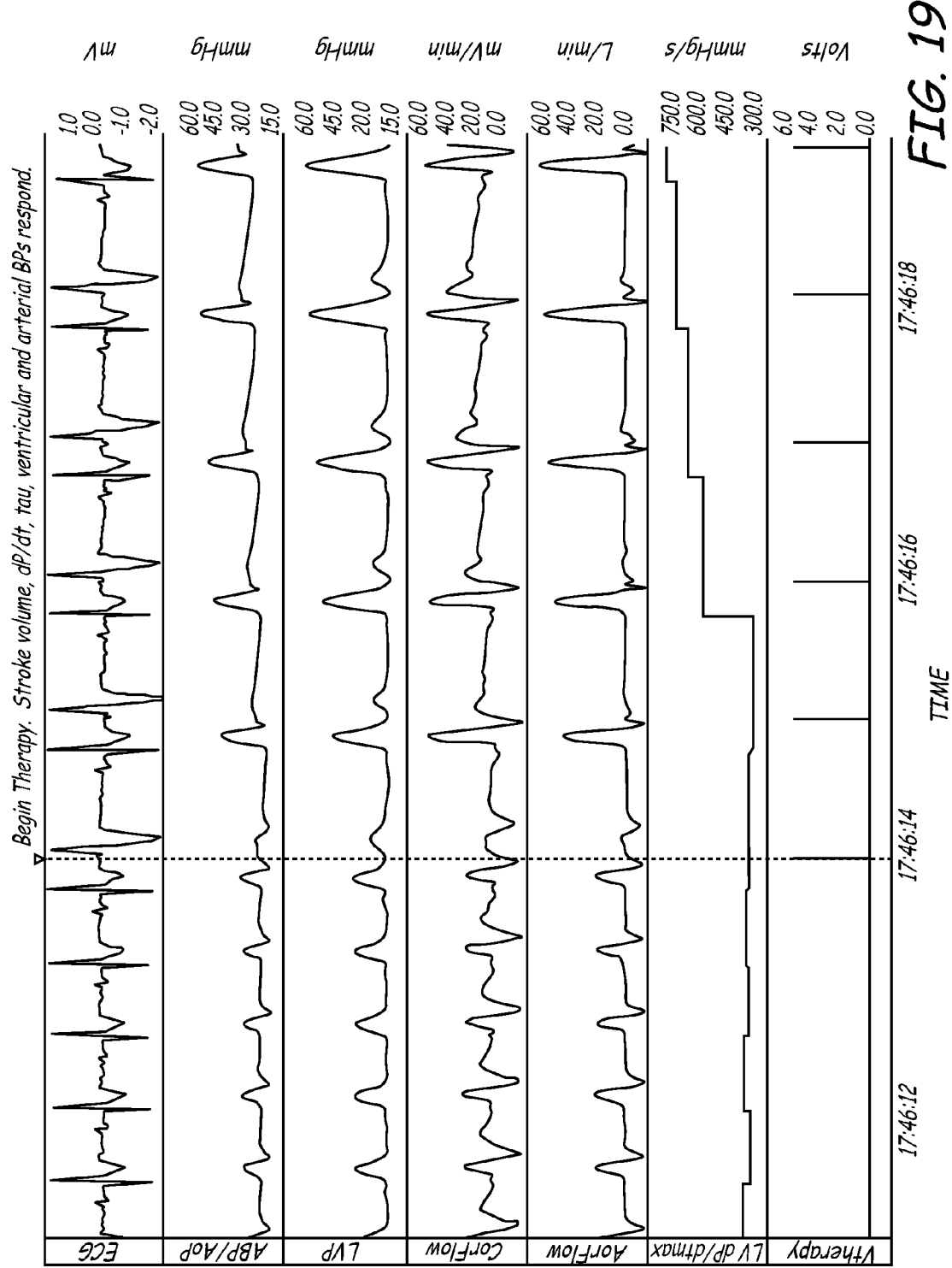
FIG. 19 is a set of traces representing physiologic and therapy activity according to the present invention.

In FIG. 19, an initiation of and response to RPS stimulation therapy is depicted. In other conditions such as HF, not necessarily associated with a preceding or concurrent tachyarrhythmia, cardiac dysfunction may deteriorate to the point where device initiated therapy is required. The onset of such cardiac dysfunction may either be gradual or sudden but upon establishing sufficient severity and duration, RPS stimulation therapy is begun. The excitatory RPS therapy shown here provides much needed increases of arterial blood pressure (ABP), coronary flow (CorFlow) and aortic flow (AorFlow) and the LV dp/dtmax value more than doubles from pre-RPS therapy in approximately five seconds.

Figure 20:
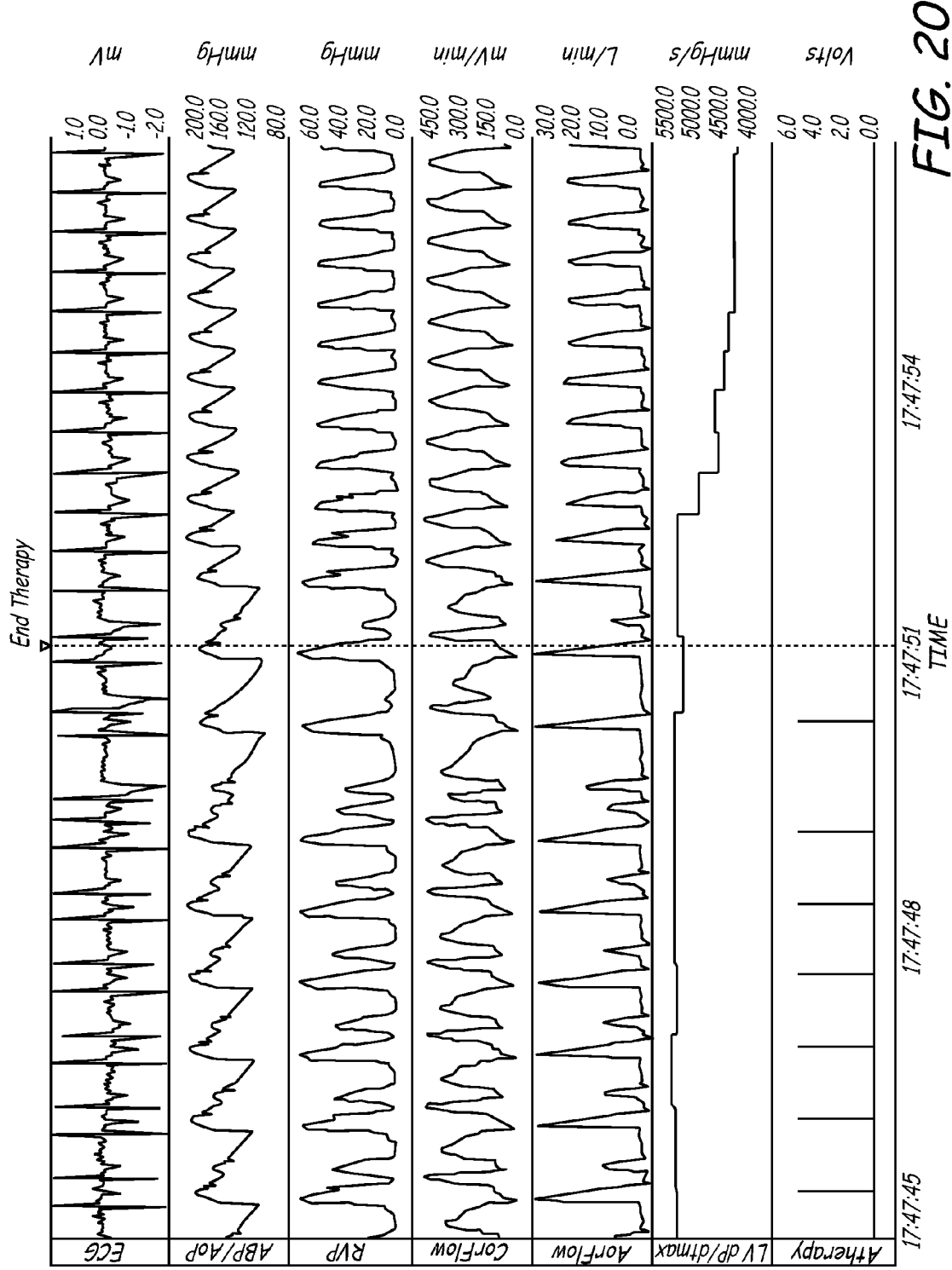
FIG. 20 is a set of traces representing physiologic and therapy activity according to the present invention.

FIG. 20 depicts termination of RPS therapy based on duration and response criteria. In FIG. 20, the termination criteria is met and RPS stimulation therapy is halted. In this case, stimulation therapy consists of atrial-only RPS stimulation therapy pulses (Ath) which capture and reset the sinus node, are conducted to the ventricles, and produce atrial and ventricular RPS due to natural conduction. In this sequence, the patient has maintained a good RV pressure (RVP) and LV dP/dtmax for over 30-60 seconds, and therefore the atrial-only RPS stimulation therapy is halted. Although the heart rate accelerates and contractility diminishes, cardiac function has recovered very significantly from the levels shown in FIG. 18 and FIG. 19 (just described).

Figure 21:
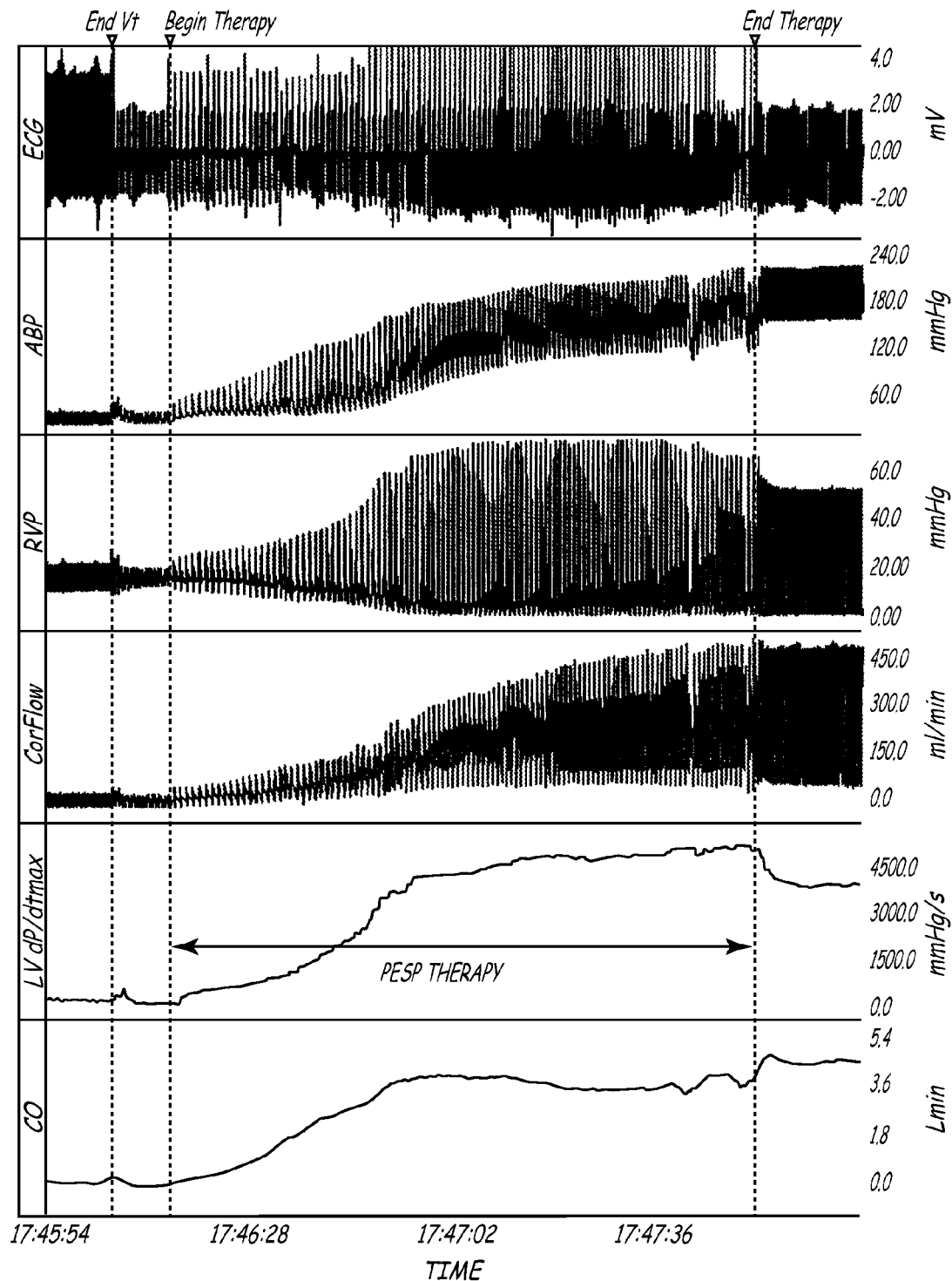
FIG. 21 is a set of traces representing physiologic and therapy activity according to the present invention.

Now turning to FIG. 21 which depiction a dramatic example of lifesaving RPS stimulation therapy. FIG. 21 illustrates (and clearly demonstrates) that post extra-systolic potentiation stimulation therapy can facilitate rapid recovery of cardiac function following a long duration of paced tachyarrhythmia in an anesthetized canine subject.

In FIG. 21, the trace denoted "ECG" is a surface ECG record, the trace denoted "ABP" is a record of arterial blood pressure measured via a catheter in the aorta of the subject, the trace denoted "RVP" is a record of blood pressure measured within the right ventricle. The trace denoted "CorFlow" is a record of blood flow in the coronary artery, the trace denoted "LVdP/dtmax" is a record of the maximum value of the $1^{st}$ derivative of left ventricular pressure per each cardiac cycle, and the trace denoted "CO" is a recording of cardiac output as derived from mean aortic flow. The record depicted in FIG. 21 begins with the final few seconds of a six-minute long, paced tachyarrhythmia (the portion of the traces before the "End VT" marker). This is followed by approximately 10 seconds of normal sinus rhythm (NSR) with severe hemodynamic dysfunction that could be classified as pulseless electrical activity (PEA) or electro-mechanical dissociation (EMD). During this time, coronary blood flow and cardiac output have not visibly increased compared to flows occurring during the tachyarrhythmia. Without adequate blood flow, the heart will remain ischemic and the subject will likely die of PEA. The portion of FIG. 21 denoted by a horizontal arrow marked "RPS Therapy," marks the period during which RPS pacing therapies were delivered in the right ventricular apex of the heart of the subject. During this period, all measured pressures and flows are appreciably augmented on the very first cardiac cycle following delivery of the first pacing (RPS) stimuli. The values continue to increase and begin to recover to normal physiologic levels within approximately one minute. At the end of the RPS therapy delivery segment, there has been sufficient coronary flow to re-perfuse the heart, allowing it to resume function without additional therapy. It cannot be overemphasized that return of spontaneous circulation in this subject occurred without any pharmacological or mechanical support therapy or treatment but instead relied exclusively on electrical stimulation delivered according to the present invention.

Figure 22:
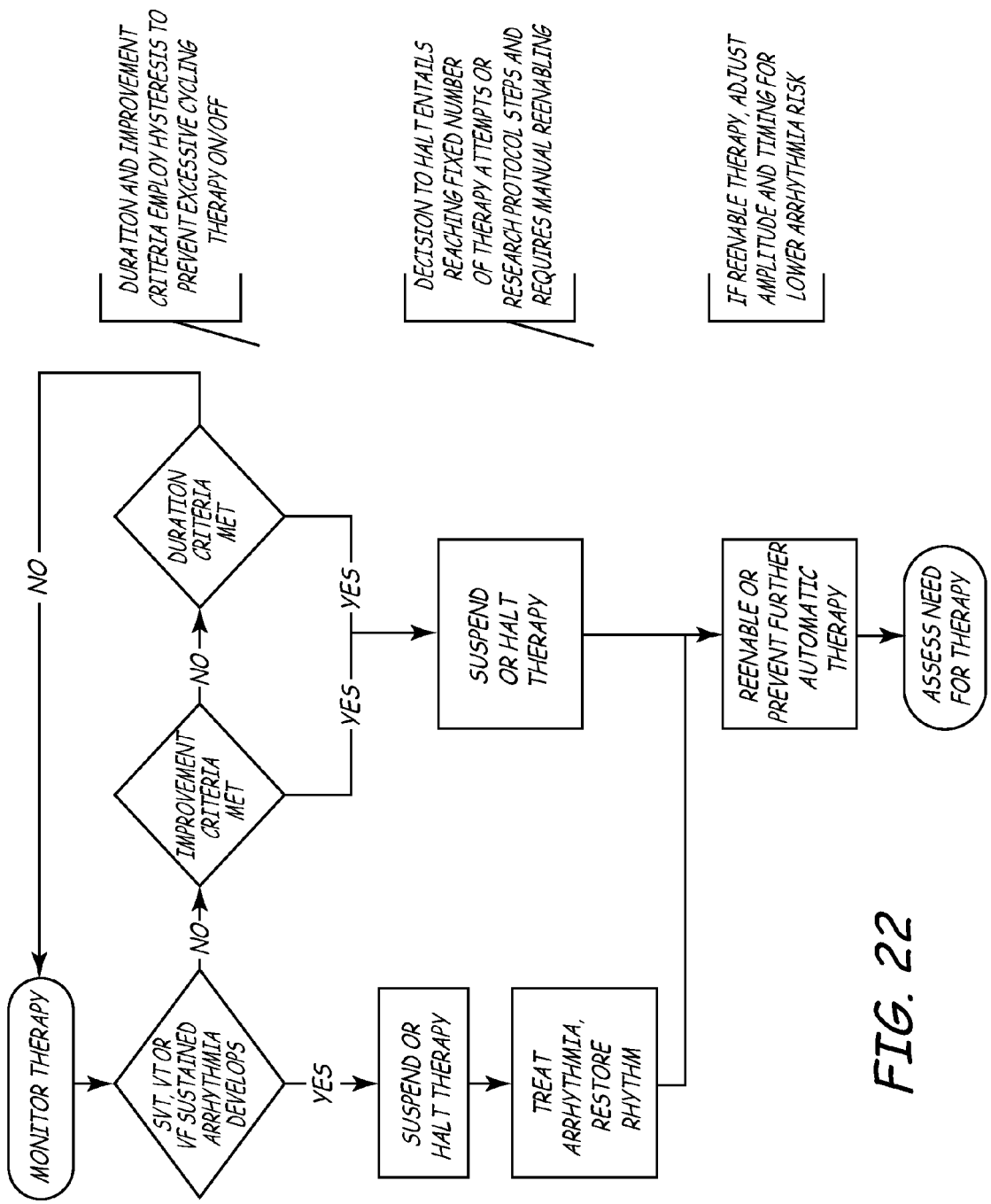
FIG. 22 is a flow chart depicting an additional aspect of the present invention.

Recognition of the need for such therapy may depend on clinicians or an automated device, either implanted or external, and stimulation therapy applied transcutaneously or from electrodes on or near the heart. FIG. 22, which is an annotated version of FIG. 17, contains some added information regarding duration and improvement criteria, halting therapy delivery and adjustment of amplitude and timing of RPS therapy to lower arrhythmia risk.

The start-stop rules may operate using a variety of schemes and sensor inputs as depicted in FIG. 2 which are microprocessor or hardware controlled and programmable with values determined by algorithms or clinicians, such as depicted in the system diagrams of FIG. 3A and FIG. 3B.

Detailed Description of Identification of Refractory and Non-Refractory Intervals.

Figure 23:
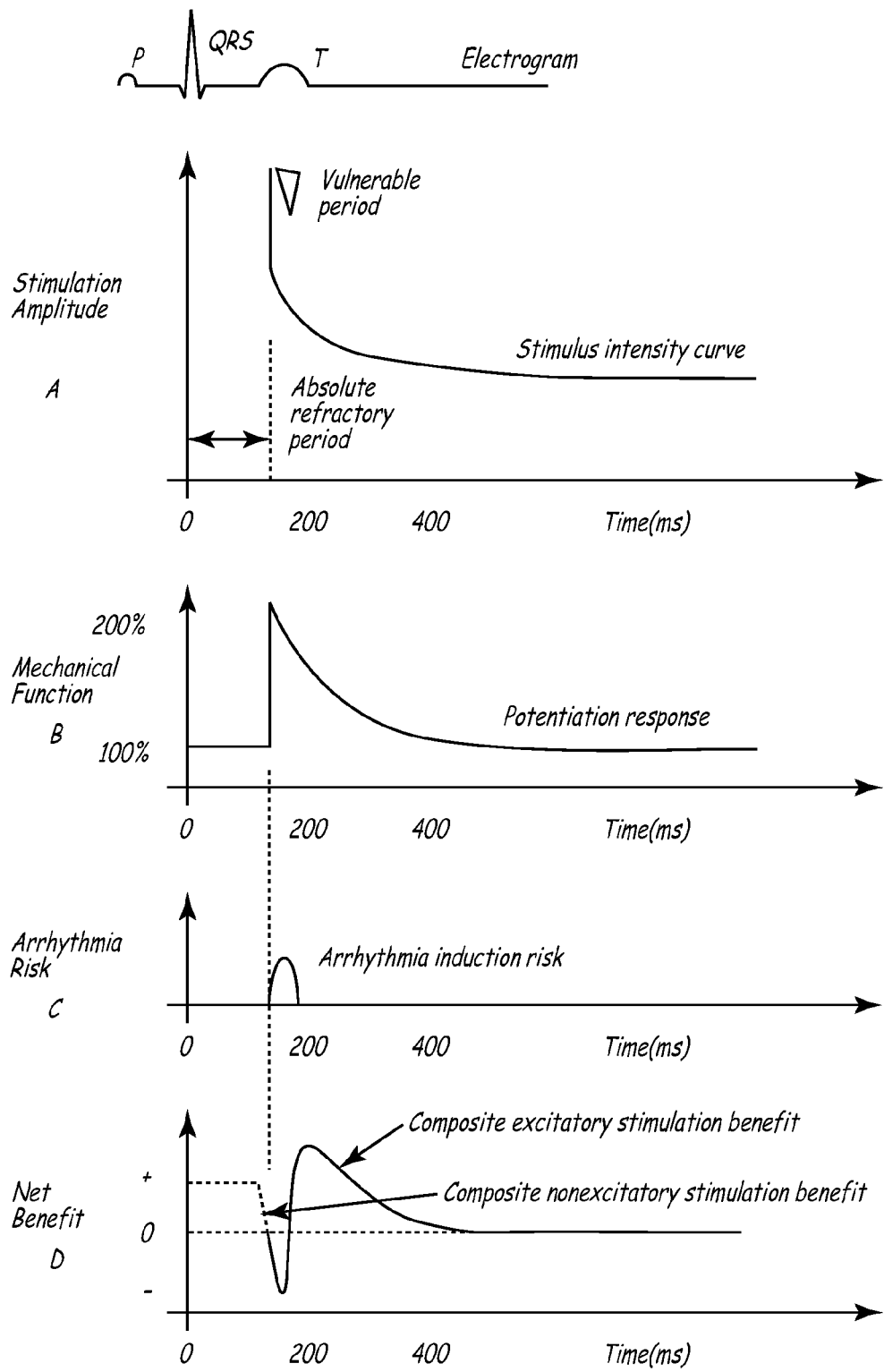
FIG. 23 is a set of four X-Y plots illustrating timing relationships between stimulation amplitude, mechanical function, arrhythmia risk and "net benefit" of therapy delivery according to the present invention.

Turning now to FIG. 23 (A through D) which is a composite illustration composed of four X-Y plots of data showing critical timing sequences between such plots of data with respect to delivery of excitatory (RPS) and nonexcitatory stimulation (NES) therapy. An unlabeled time-aligned surface representative ECG electrogram trace appears at the top of the figures for ease of cross-reference.

In FIG. 23A, a stimulus intensity curve is depicted wherein a primary determinant of the timing associated with arrhythmia risk and hemodynamic benefit derived from RPS excitatory stimulation. It will be appreciated that stimulation pulses of greater amplitude than the curve (at a given moment in time) are necessary to capture and thus provide benefit from RPS stimulation therapy. An absolute refractory period is depicted in FIG. 23A. During this period no depolarizations result and this is ideal for nonexcitatory neurostimulation (NES) with electrodes near the heart. In the period labeled "vulnerable period," which occurs just outside of the absolute refractory period, very high amplitude pulses can cause arrhythmias including repetitive extrasystoles, VT, or VF. For practical purposes, excitatory stimulation pulses are delivered some margin above the threshold so that capture is a binary phenomenon. Stimulation pulse amplitude, however, is also maintained low so that the risk of arrhythmias is very low even when timed to coincide with the vulnerable period (for comparison see FIG. 23C, "arrhythmia induction risk curve"). As is well known in the literature, the magnitude of the potentiation seen on the beat following the extrasystole (the post extrasystole beat) is a function of the extrasystole's timing—becoming greatest just before losing capture (as shown in FIG. 23B, (labeled "potentiation response" curve). The solid curve depicted in FIG. 23D (labeled "Net Benefit" curve), combines physiologic benefit from excitatory RPS stimulation and arrhythmia risk. It is most desirable to stimulate a little bit longer than (i.e., beyond) the refractory/nonrefractory boundary. The dashed Net Benefit curve shows that nonexcitatory neurostimulation (NES) is best delivered on the "short side" of the refractory/nonrefractory boundary (or else excitation could result). The present invention includes methods to help the clinician or automated device find this refractory/nonrefractory boundary and thus achieve the benefits of the intended therapies while controlling risk.

Figure 24:
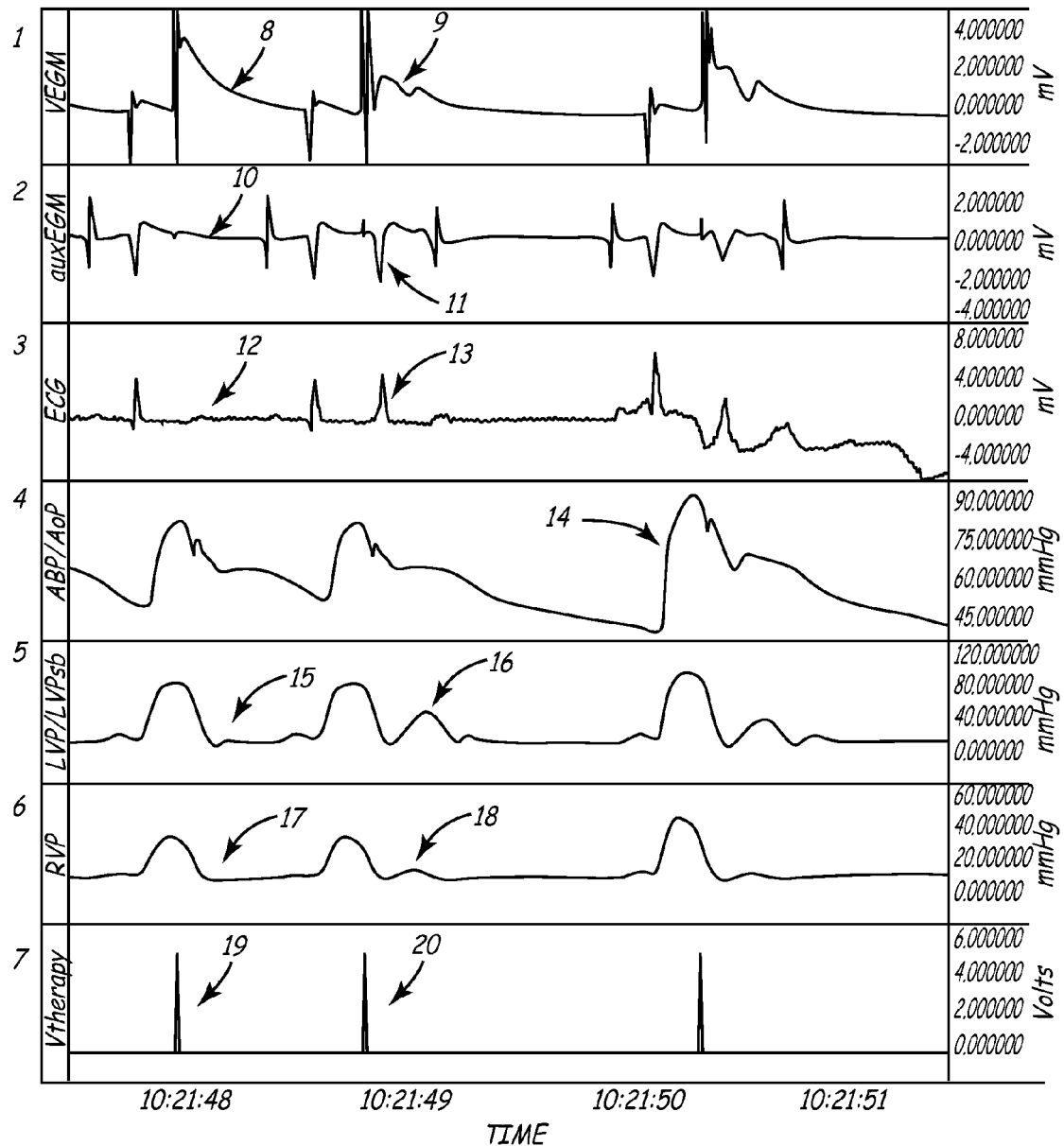
FIG. 24 is a set of traces representing physiologic and therapy activity according to the present invention.

Referring now to FIG. 24, which is a graphical depiction of electrical and hemodynamic detection of cardiac chamber capture. The trace labeled "1" is a ventricular electrogram (VEGM) obtained from the site of application of the stimulation therapy. The trace labeled "2" is a second electrogram that is near both right atrium and right ventricle and is away from the site of application of the pacing therapy. The trace labeled "3" is a surface ECG, traced "4" is a record of arterial blood pressure (ABP), trace "5" is a record of left ventricular pressure (LVP), trace "6" is a record of right ventricular pressure (RVP) and trace "7" is a marker channel record of stimulation therapies applied to the ventricles (Vtherapy). FIG. 24 illustrates embodiments of the concept of the identification of whether or not a cardiac potentiation therapy lies inside or outside the cardiac refractory period.

With respect trace 7, arrow 19 identifies a therapy is delivered to the ventricle that lies inside the refractory period, arrow 20 identifies a therapy that lies outside the refractory period. With respect to trace 1, arrow 8 identifies an electrogram tracing following a therapy that shows no evidence of a resultant depolarization, confirming that the therapy lies in the refractory period, and arrow 9 identifies an electrogram tracing showing a cardiac depolarization following the therapy, confirming that the therapy pulse captured, had sufficient amplitude and duration, and was outside the refractory period.

Similarly, with respect to trace 2, arrows 10 and 11 identify noncapture and capture, respectively, from the electrogram at an auxiliary electrode site suitable to identify pulses inside and outside of the cardiac refractory period by the absence or presence of a ventricular depolarization. With respect to trace 3, arrows 12 and 13 identify the absence and presence of ventricular depolarizations on a surface ECG, respectively.

An embodiment of the invention would be to apply a detection algorithm to electrogram signals (possibly including but not limited to signal traces 1-3) and identifying the presence or absence of an evoked depolarization. This information is then used to identify whether the preceding therapy was inside or outside of the cardiac refractory period.

With respect to trace 4, arrow 14 points to a significantly augmented ABP wherein the arterial pulse pressure on the cardiac cycle following a therapy that lies outside the refractory period was augmented. Similarly, LVP (trace 5) and RVP (trace 6) are also augmented on the cycle following capture. Thus, FIG. 24 illustrates an embodiment of the invention used to detect the presence of pressure, flow, acceleration, impedance change, or other favorable evidence of mechanical augmentation following therapy delivery. This evidence also helps identify whether or not the preceding therapy was delivered inside or outside of the cardiac refractory period.

With respect to traces 5 and 6, arrows 15 and 17 indicate portions of a left and right ventricular pressure waveform, respectively, resulting from stimulation therapy delivered in the cardiac refractory period. As a result, no evidence of an extra-systole is seen following the therapy.

Again with respect to traces 5 and 6, arrows 16 and 18 are pressure waveforms following a therapy delivered outside of the cardiac refractory period. An extra-systole can be seen following this therapy. Another embodiment of the invention is adapted to apply a detection algorithm to a sensor that makes a measurement of cardiac mechanical activity, including but not limited to right ventricular, left ventricular or arterial pressure, dimension, or acceleration and identifying the presence or absence of an extra systole. This information is used to identify whether the preceding therapy was inside or outside of the cardiac refractory period. Evoked R wave detection information may then be used to time or trigger delivery of a stimulation therapy that would cause post extra-systolic potentiation or would be nonexcitatory for neurostimulation, or both.

Figure 25:
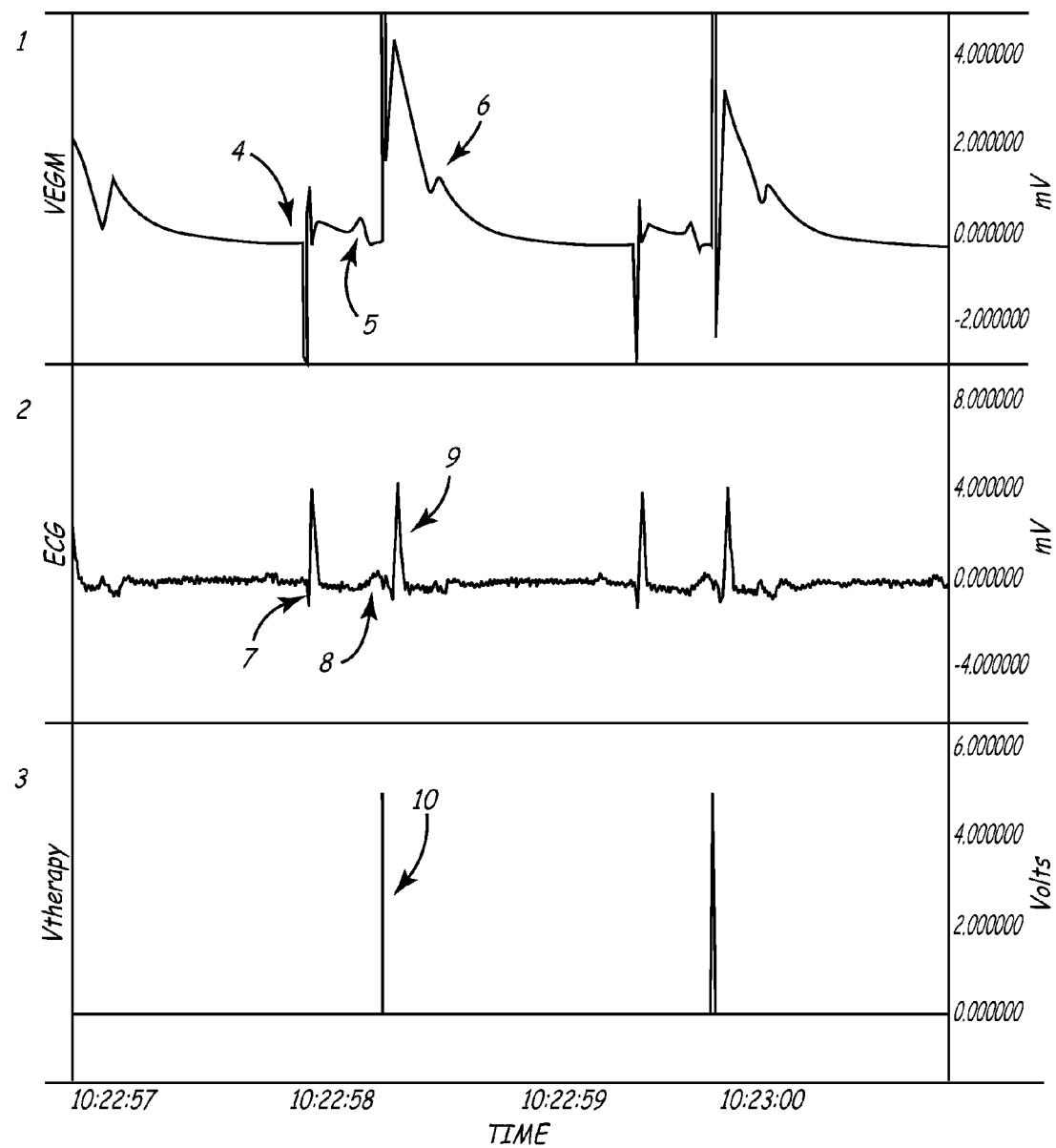
FIG. 25 is a set of traces representing physiologic and therapy activity according to the present invention.

FIG. 25 depicts three traces, VEGM, ECG and Vtherapy, respectively which can be used to determine whether or not capture has occurred by analyzing a T wave. Trace 1 is a ventricular electrogram (VEGM) from the site of application of the stimulation therapy, trace 2 is a surface ECG, and trace 3 is a marker channel record of applied stimulation therapies. With respect to trace 1 and 2, arrows 4 and 7 are electrogram signals indicating a ventricular depolarization and arrows 5 and 8 are signals showing a resulting ventricular repolarization or T-wave. In trace 3, arrow 10 corresponds to a marker of the delivered therapy, which was applied just after the T-wave. In traces 1 and 2, arrows 6 and 9 indicate the resultant depolarization from the applied therapy.

Another embodiment of the therapy capture aspect of this invention is used to identify the T-wave from an electrogram signal following application of a therapy pulse. A further embodiment is to rely directly on the time of occurrence of the T-wave (between the depolarization and repolarization from an electrogram signal) to form an index of the boundary between refractory (before the T-wave) and nonrefractory (after the T-wave) intervals. The T-wave detection information may then be used to time or trigger delivery of a stimulation therapy that would cause post extra-systolic potentiation or would be nonexcitatory for neurostimulation, or both.

Figure 26:
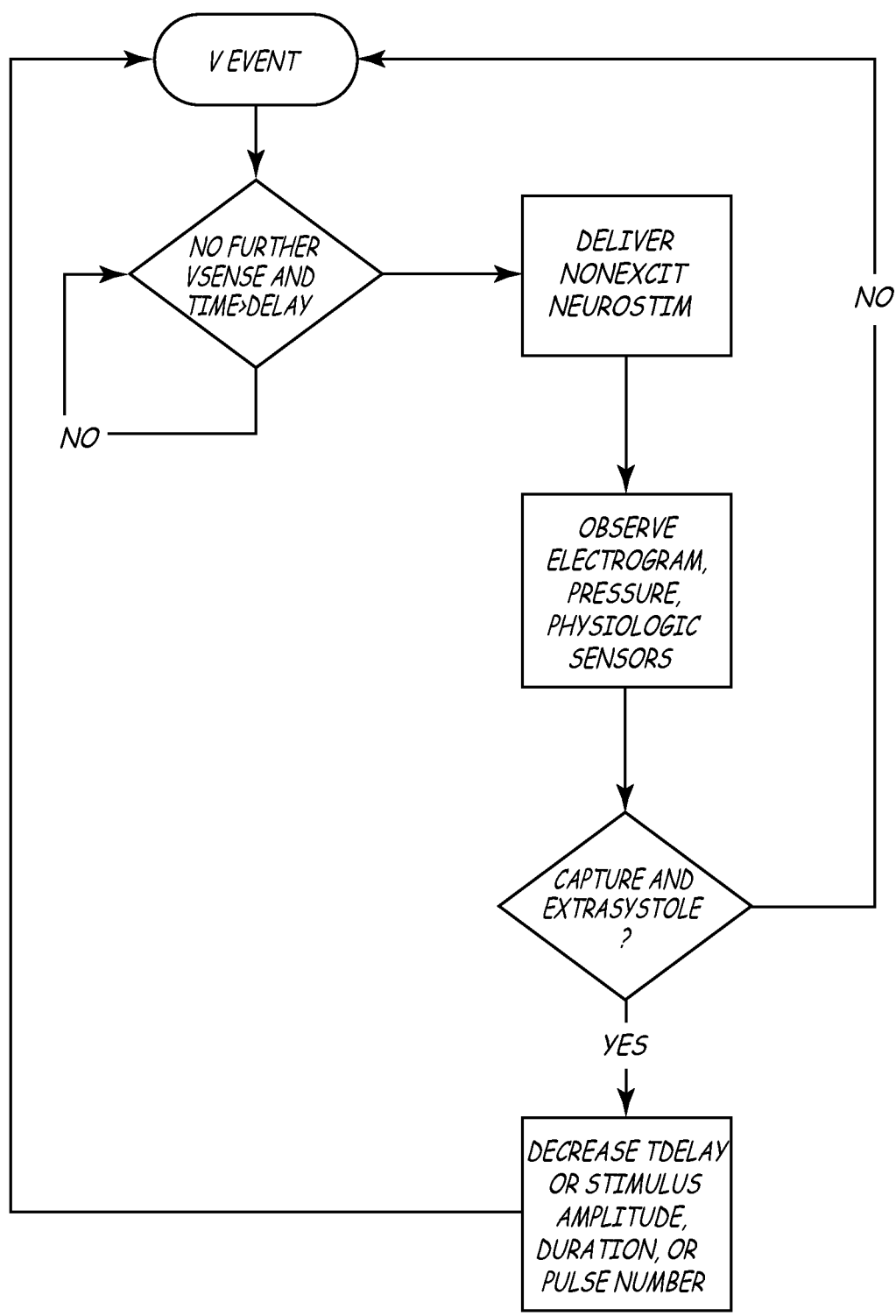
FIG. 26 is a flow chart depicting an additional aspect of the present invention.

FIG. 26 is a flow chart that diagrams response to capture information to apply nonexcitatory neurostimulation (NES) therapy. Following a ventricular pace or sense event, the sensing circuits remain active and a timer counts down a delay until the scheduled delivery of the NES stimulation pulse(s). If there has been no intrinsic event in this interval, the NES pulse(s) are delivered and electrogram or mechanical sensor signals employed (such as described herein above) to determine if capture and an extrasystole occurred. If capture did not occur, the delivery time, stimulation amplitude, or pulse number is decreased and the process repeated. The value for Tdelay is typically 10-120 ms. Tdelay and other stimulus parameters may also be influenced by observations of heart rate or other physiologic sensors in addition to the electrical and mechanical parameters discussed above.

Figure 27:
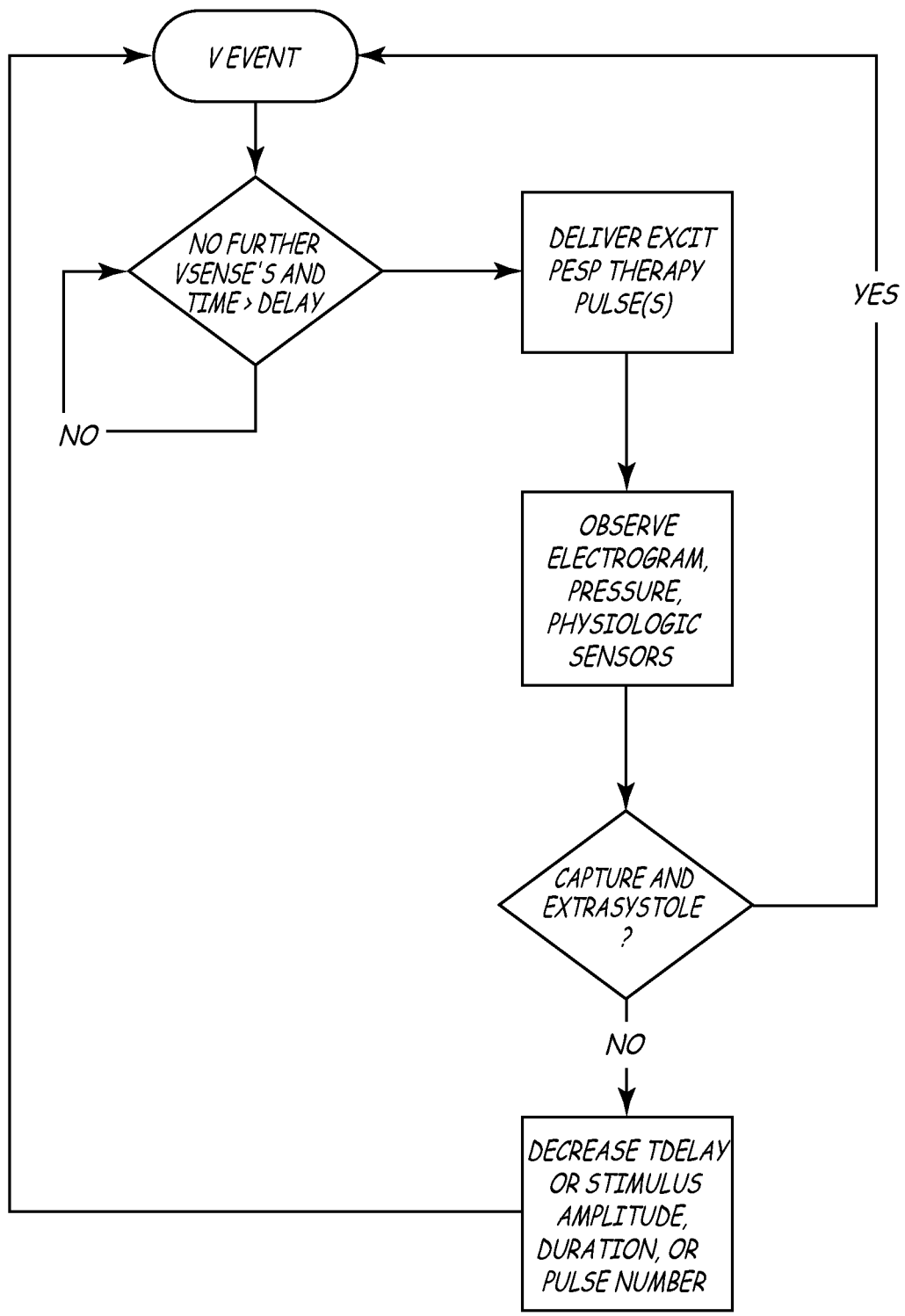
FIG. 27 is a flow chart depicting an additional aspect of the present invention.

FIG. 27 is a flow chart that diagrams response to capture information to apply excitatory RPS therapy. Following a ventricular pace or sense event, the sensing circuits such as depicted in FIG. 3A and FIG. 3B remain active and a timer counts down a delay until the scheduled delivery of the RPS stimulation pulse(s). If there has been no intrinsic event in this interval, the pulse(s) are delivered and electrogram or mechanical sensor signals employed (such as described herein above) to determine if capture and an extrasystole occurred. If capture did not occur, the delivery time, stimulation amplitude, or pulse number is increased and the process repeated. The value for Tdelay is typically 200-300 ms. Tdelay and other stimulus parameters may also be influenced by observations of heart rate or other physiologic sensors in addition to the electrical and mechanical parameters discussed above. This algorithm is also used for the pulse(s) intended to produce RPS when accompanied by NES pulse(s).

The identification of refractory and non-refractory intervals and appropriate timing of pulses may operate using a variety of timing schemes and sensing circuits which are both preferably microprocessor or hardware controlled and programmable with input values determined by algorithms or clinicians, such as depicted in the system diagrams of FIG. 3A and FIG. 3B.

Detailed Description of Management of SVT with RPS Therapy.

Figure 28:
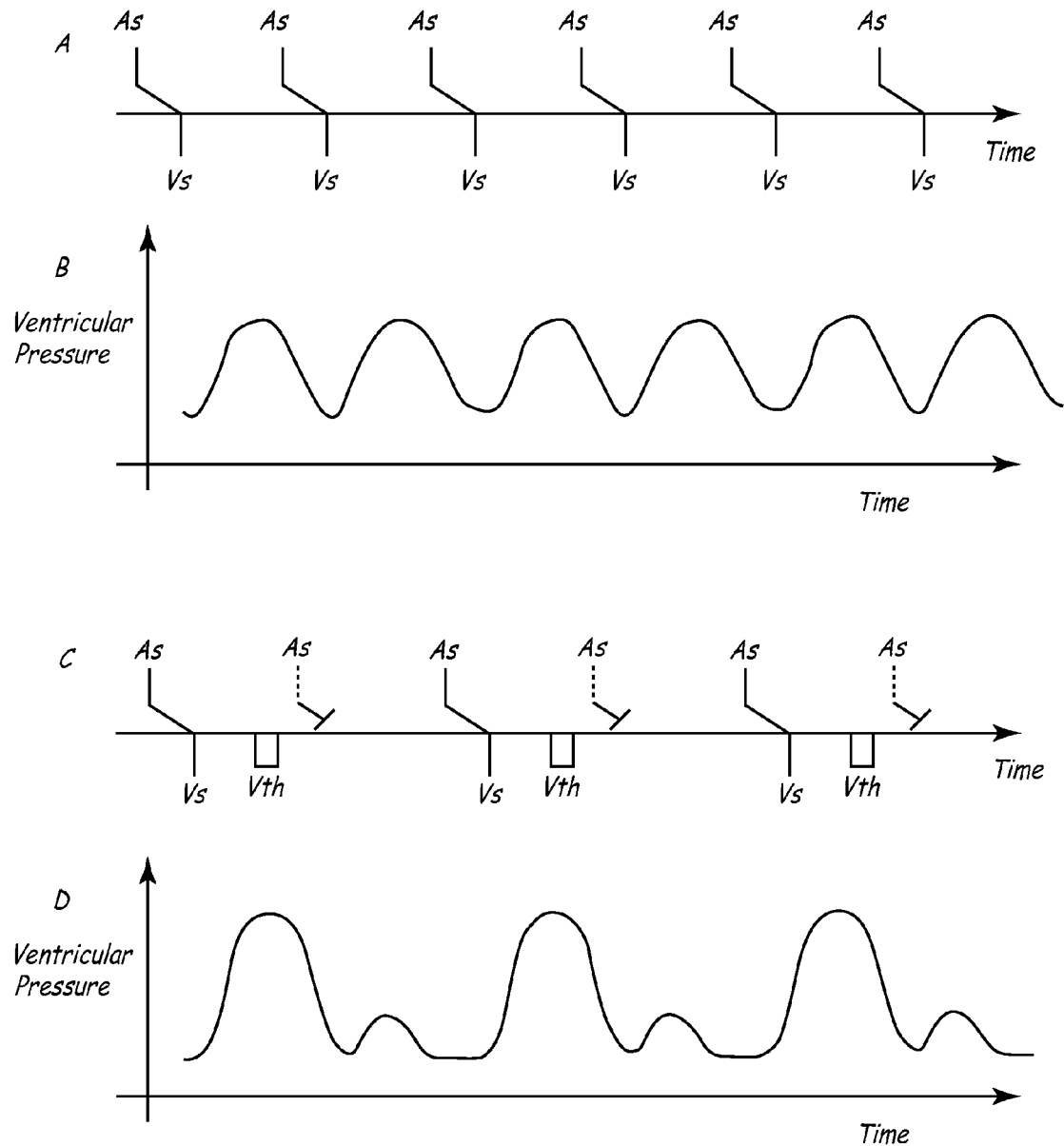
FIG. 28 is a flow chart depicting an additional aspect of the present invention.

FIG. 28 is a series of four X-Y plots (labeled A-D) illustrating deceleration of a rapid SVT by applying RPS therapy according to one embodiment of the present invention. Such a rapid SVT results when ectopic or reentrant rhythms involve the atria or AV node and conduct to the ventricles (trace A). Conduction to the ventricles is so rapid as to impair filling and ejection and as a result pressures and flows are typically impaired (trace B). The introduction of excitatory RPS stimulation pulses (denoted Vth in trace C) creates additional refractory time in the ventricles and a 2:1 rate reduction takes place. Furthermore, potentiation and enhanced mechanical function results (as seen in D). The net result is an effective rate reduction with improved hemodynamic performance. This RPS therapy regimen not only transforms a potentially life threatening SVT into a well tolerated rhythm, but allows more time for termination of the arrhythmia by natural, device, or drug means.

The deceleration of rapid SVT by RPS therapy may operate using a variety of timing schemes and sensing circuits which are both preferably microprocessor or hardware controlled and programmable with input values determined by algorithms or clinicians, such as depicted in the system diagrams of FIG. 3A and FIG. 3B.

Detailed Description of Feedback Control.

Figure 29:
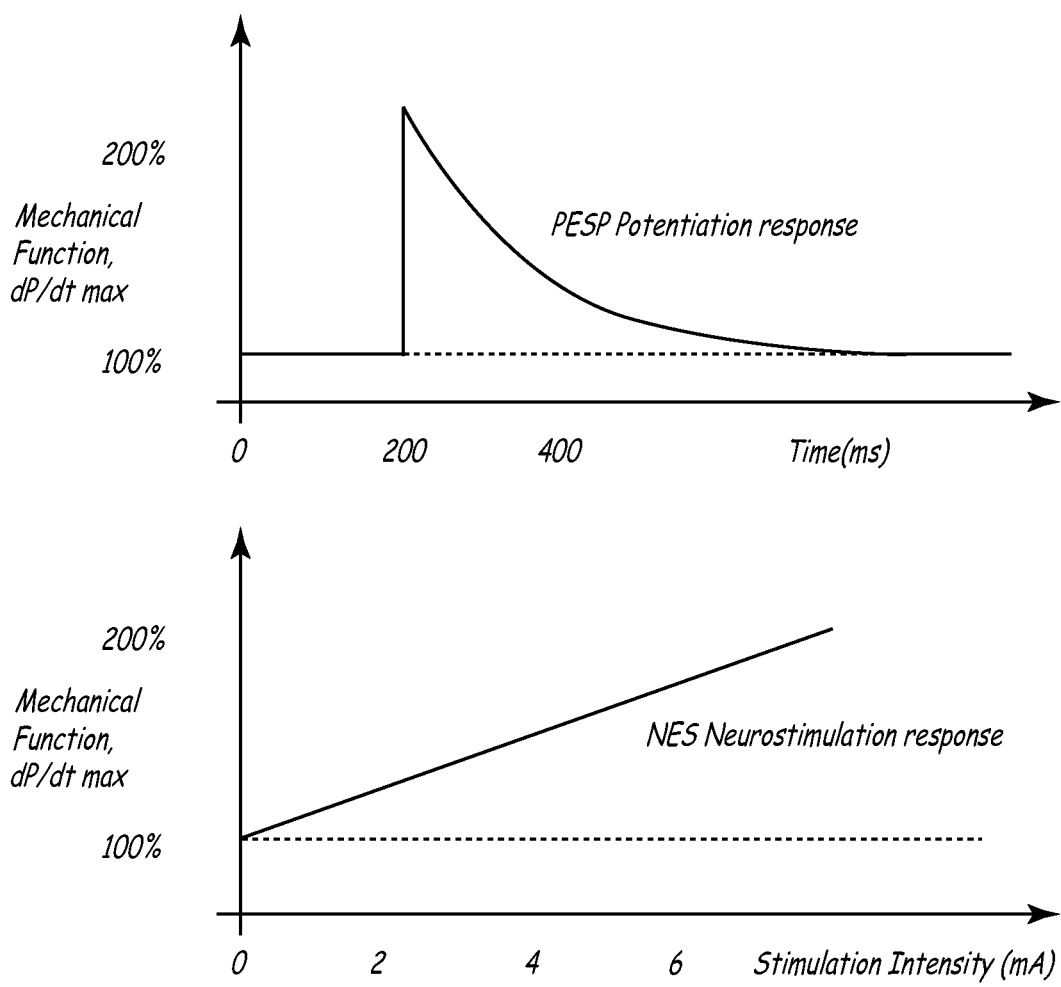
FIG. 29 is a pair of X-Y plots showing the relationship between mechanical function (dP/dtmax) as a function of time and stimulation intensity, respectively.

FIG. 29 is composed of two X-Y plots illustrating basic control relationships for NES and RPS stimulation. In FIG. 29, the index of cardiac mechanical function is taken to be dP/dt max as a percentage of baseline, although other variables such as arterial pulse pressure or cardiac output may be used. In the top X-Y plot appearing near the top of FIG. 29, the RPS potentiation response is seen to be governed by the timing of stimulation that elicits an extrasystole. It is not affected by stimulation intensity and needs to be outside of the refractory period (here shown as 0-200 ms). Non-excitatory neurostimulation, however needs to be nonexcitatory and for electrodes near the heart this means inside the refractory period. NES is also strongly dependent on stimulation intensity (here shown as current in mA but may also include voltage, pulse duration or the number of multiple pulses).

Figure 30:
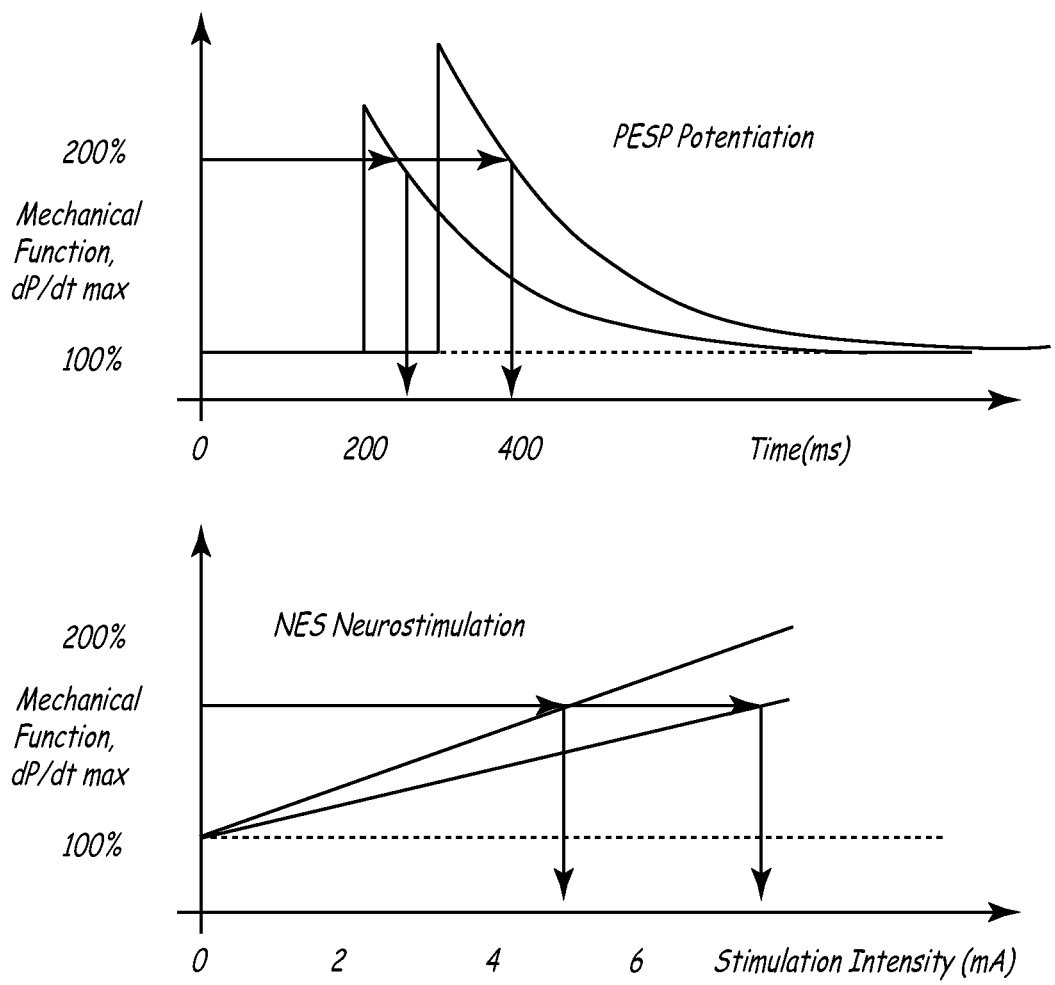
FIG. 30 is a pair of X-Y plots showing the relationship between mechanical function (dP/dtmax) as a function of time and stimulation intensity, respectively.

FIG. 30 is composed of two X-Y plots illustrating the need to adjust stimulation parameters to maintain desired level of enhanced function. Variations across and within subjects of response to stimulation occur and can impact the resulting level of enhanced function. For both RPS potentiation and NES neurostimulation this may take the form of shifts in the absolute level of response (or offset) but for convenience this has been removed by normalizing to a non-stimulated baseline in the recent past of 100%. The remaining variation takes the form of shifts in the slope or the NES response, but for RPS takes on both changes of slope (change of dP/dt max per unit time) as well as shifts in the refractory period where no potentiation results. As a result, a stimulation time that once gave the desired level of enhancement may now be associated with no enhancement, more or less mechanical function enhancement of the heart, and a different slope. In order to maintain a level of beneficial effect on cardiac function, some sort of closed loop control of stimulation is necessary.

Figure 31:
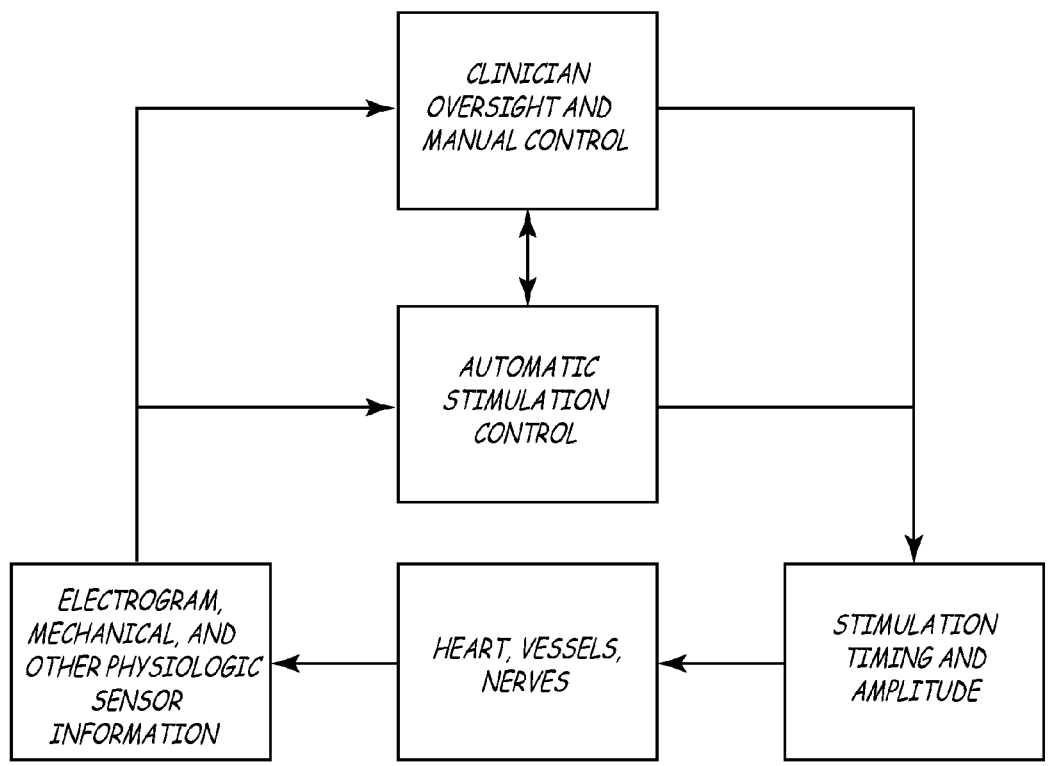
FIG. 31 is a flow chart depicting an additional aspect of the present invention.

FIG. 31 is a flow chart of depicting a means to control the level of enhanced cardiac function. Adjustments in stimulation timing or amplitude act on the heart and associated tissues and organs and are observed by electrical, mechanical, metabolic, or other physiologic sensors. In the most elementary situation, a clinician observes this sensor information and adjusts the stimulation accordingly. This may be thought of as closing the loop but results in a slow response time. Implantable or external device implementations of this invention may also close the loop more promptly by following a control algorithm in a portion of the therapy delivery device termed a controller. As with all practical control systems, provision for manual override and tuning of the controller are provided. This aspect of therapy control may be considered separately from the start/stop and safety lockout rules described elsewhere.

Figure 32:
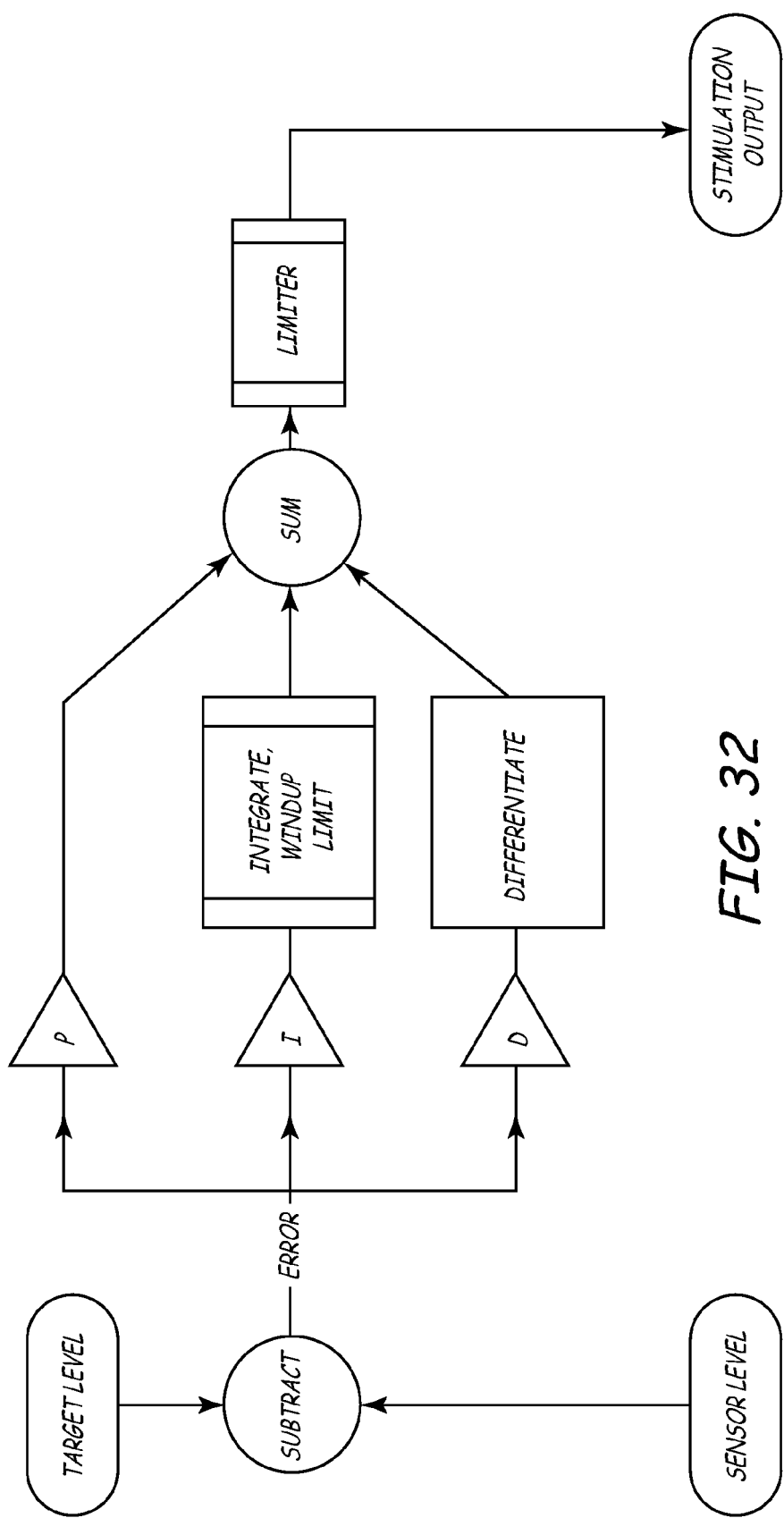
FIG. 32 is a flow chart depicting an additional aspect of the present invention.

FIG. 32 is a block diagram illustrating a basic PID controller for automatic adjustment of stimulation therapy. One of the most basic of automatic control schemes is the PID controller depicted in FIG. 32. A target level (or setpoint) is compared with the actual level derived from a sensor and the difference is referred to as the error. In a PID controller, there is a proportional pathway with an associated multiplicative constant P, a pathway that integrates the error with constant I, and a pathway that works with the derivative of the error with constant D. Practical PID controllers usually implement absolute limits to the commanded output and similarly limit the integral of error (a property called anti-windup limiting). Furthermore these controllers are also usually implemented in a fashion such that the transition from manual or fixed output to automatic control output occurs smoothly (a property called bumpless transfer). In the present application, this controller updates stimulation parameters once per cardiac cycle with relatively straightforward computations and thus is not a significant burden to the processing power of implanted or external medical instrumentation.

Figure 33:
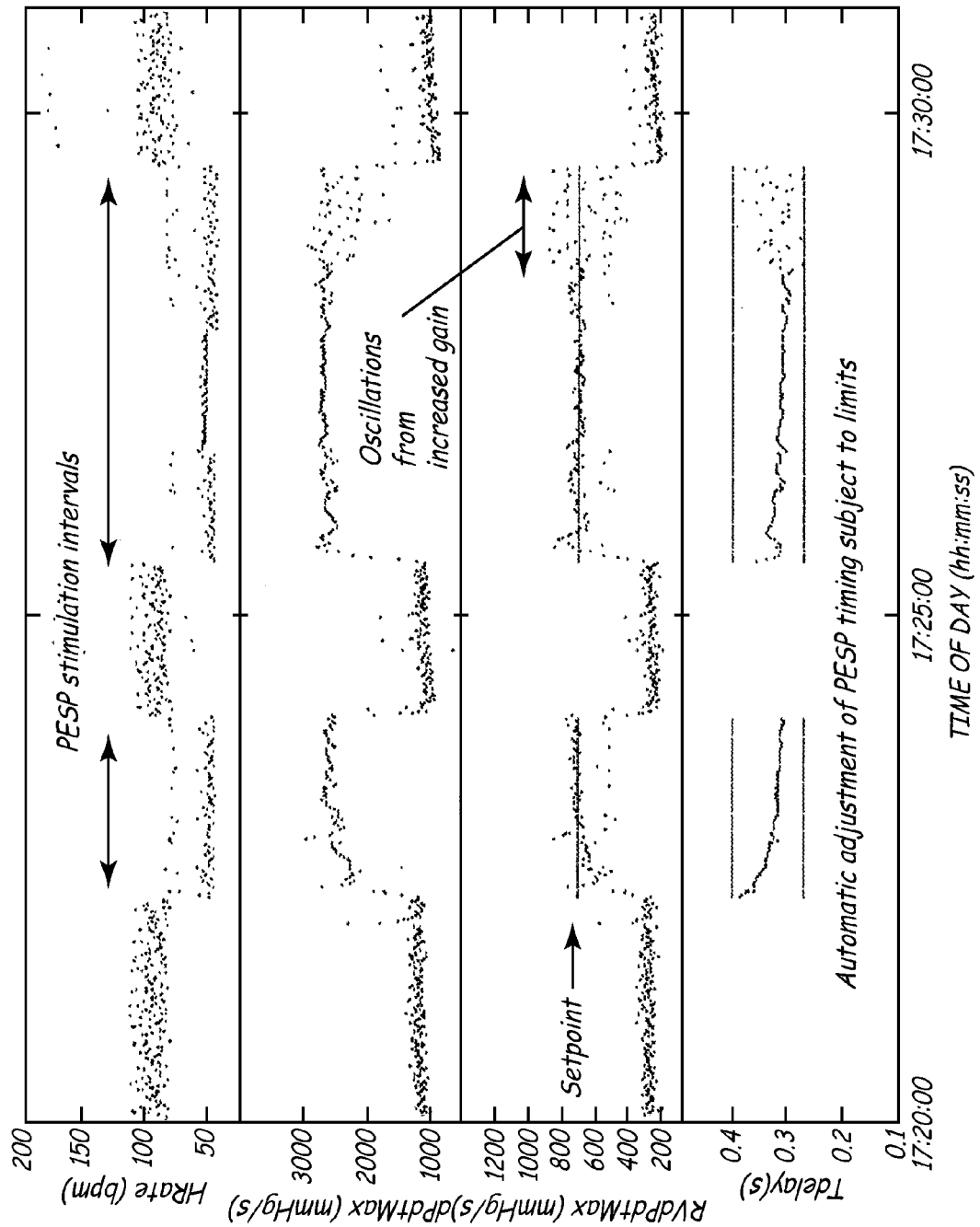
FIG. 33 is a set of plotted empirical data representing physiologic and therapy activity according to the present invention.

FIG. 33 depicts a series of empirical measurements that illustrates the effect of a P+I controller maintaining RPS cardiac enhancement. A P+I controller was employed using RV dP/dt max as the control variable and the results are shown here. A setpoint of 700 mmHg/s was entered (which was significantly greater than the baseline level of 280 mmHg/s). Limits for the RPS therapy pulse's timing were established (here 250 to 400 ms was used) and the therapy initiated. The desired level of enhanced function was achieved rapidly and the mean level of RV dP/dt max remained around the setpoint as the feedback controller continuously adjusted the timing (Tdelay). Incorporation of an integrator in the feedback loop assures the mean error is zero. In this patent disclosure, the inventors report that they increased the controller gain to the point where oscillations developed, an instability phenomenon well known in the area of feedback control. RPS stimulation not only decreased heart rate from 90 to 50 bpm, but also resulted in a simultaneous and sustained increase in LV dP/dt max from about 1100 to 2600 mmHg/s. A significant feature of this invention is that in the process of adjusting RPS stimulation timing to maintain a desired level of enhanced function, the controller automatically adapts to changes in the potentiation response curve. This keeps the controller clear of the refractory period and in an operating region where linear feedback control applies. Similar linear feedback controllers may be applied to NES neurostimulation and combined NES and RPS stimulation. Such controllers also act in concert with rules for starting and stopping stimulation therapy and safety lockout rules as described elsewhere in this invention.

The feedback control may operate using variations of the controllers described which are preferably microprocessor or hardware controlled and programmable by algorithms or clinicians, such as depicted in the system diagrams of FIG. 3A and FIG. 3B.

Detailed Description of Extensions to Tachyarrhythmia Management Devices.

Figure 34:
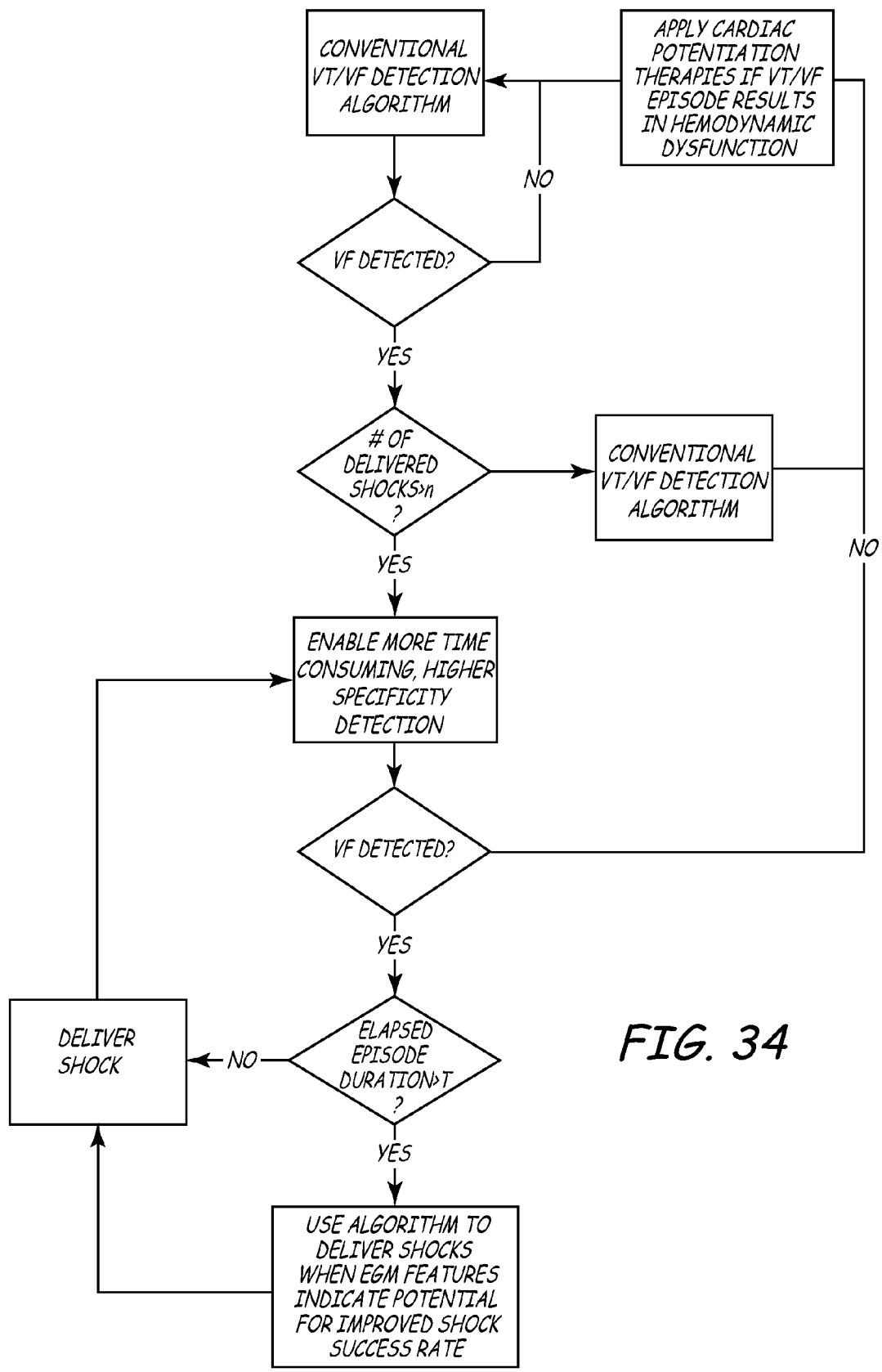
FIG. 34 is a flow chart depicting an additional aspect of the present invention.

FIG. 34 is a flow chart depicting a technique for extending usual shock algorithms for ICDs and AEDs to facilitate NES and/or RPS therapy. Another important aspect of this invention is the recognition that certain seriously compromised states formerly believed almost uniformly fatal such as EMD or PEA, may in fact respond to electrical stimulation therapy. Present generation ICD and AED devices may then be altered to reflect this possibility. This flow chart illustrates some significant changes. First, it introduces the RPS, NES, or combined stimulation therapies described elsewhere in this invention into the device's algorithm by checking for the presence of severe hemodynamic dysfunction after tachyarrhythmia termination and applying therapies. Then, if more than a set number of shocks (n) are delivered in a single episode or cluster of episodes, more time consuming and accurate VF detection rules are instituted to reduce the risk inadvertently shocking rhythms that do not respond to shocks while still maintaining the capability to recognize and treat VF. The potential negative impact of slower VF detection is now balanced by less risk of inadvertent shocks and an implementation of stimulation therapy to assist in recovery of longer duration tachyarrhythmias. Finally, the flow chart introduces a further analysis of surface ECG or intracardiac electrogram signals or other sensors following an extended but unsuccessful effort to end the tachycardia. The device or the device and clinician look for features that are associated with an improved success rate for tachyarrhythmia conversion such as fine VF. Although current thinking is that the survival rate when responding to shocks or ATP therapies this late into a tachycardia episode is too poor to warrant therapies, the stimulation therapy invention described herein appears to have opened the door to further life saving and life sustaining therapies.

An additional aspect of the present invention is to modify existing rhythm recognition algorithms of implanted and external therapy devices to accommodate operating concurrently with therapy pulses delivered by a preexisting external or implanted device respectively. The sharp changes in electrogram slew rate associated with stimulation pulses may be recognized and ignored for the purpose of automated rhythm recognition. Further, closely coupled pairs of ventricular depolarizations with stimulation pulses detected shortly before the second depolarization, in the setting of cardiac dysfunction, are presumed to be RPS extrasystoles and not an intrinsic bigeminal tachycardia rhythm. The devices analyze the effective heart rate and rhythm accordingly and do not falsely detect or treat tachyarrhythmias.

Diagram of Integrated RPS, NES, Defibrillation and Pacing Concepts

Figure 35:
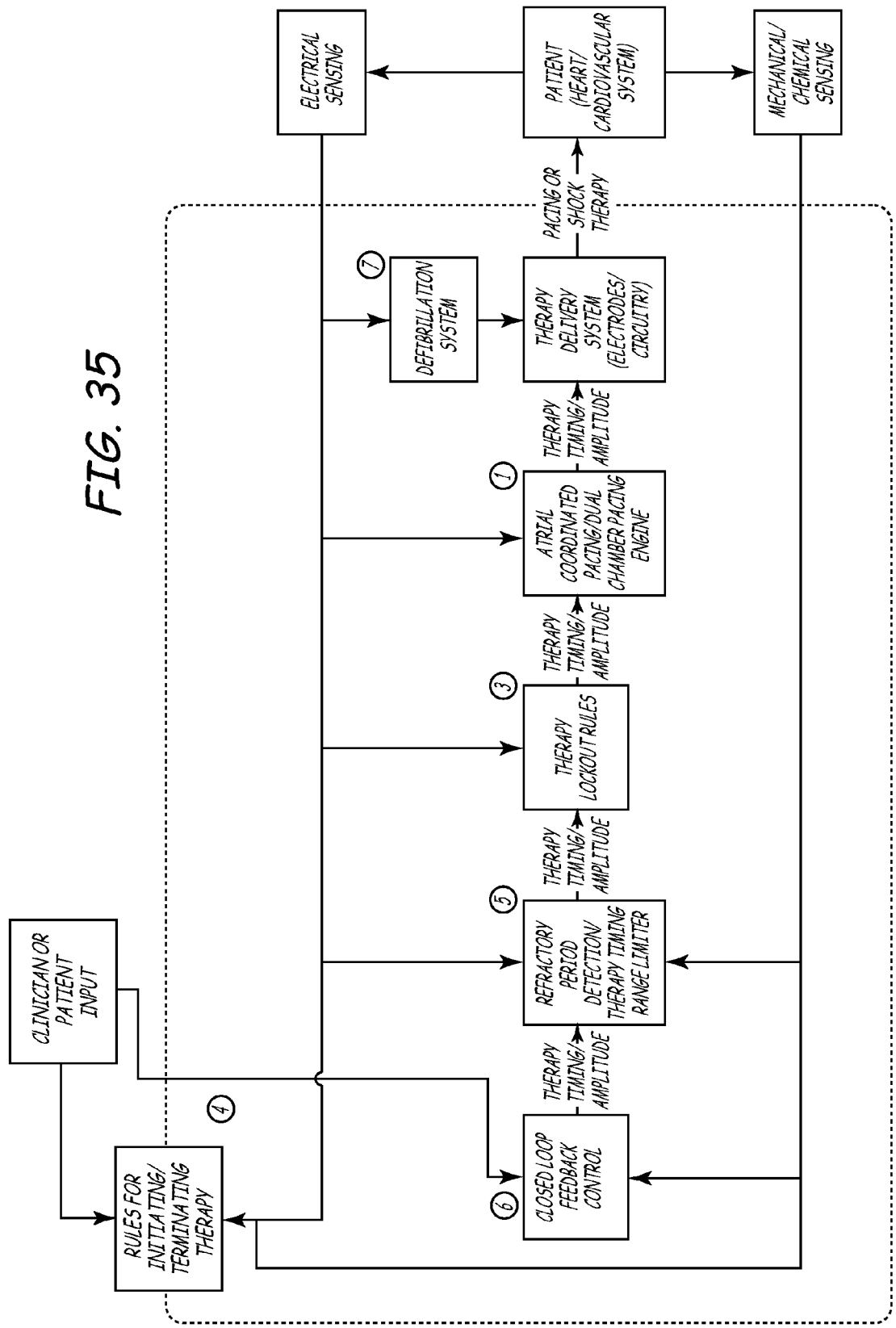
FIG. 35 is a flow chart depicting an additional aspect of the present invention.

FIG. 35 is a flowchart illustrating significant aspects of stimulation therapies according to some aspects of the present invention described herein. Various components of this invention work together to provide safe and effective stimulation therapies for cardiac dysfunction, including arrhythmias and HF, among others. Beginning with the upper left portion of FIG. 35, block 4 incorporates the rules by which therapy as a whole is initiated or terminated, thus this aspect (block 4) encloses the others in the dotted border. This aspect may be an automated algorithm or may require input from a clinician or the patient. Block 6 depicts the closed loop feedback controller that gathers a measure of cardiac function from the mechanical sensors and a desired control point from the clinician or patient. The controller depicted as block 6 then adjusts the timing or the amplitude of the therapy to achieve this desired control point. Block 5 includes the algorithms used to identify the refractory period of the heart which uses as an input either electrical sensing of cardiac depolarizations or repolarizations or mechanical sensing of extra-systoles or potentiation. If non-excitatory neurostimulation (NES) is desired, the algorithm keeps the therapy timing within the refractory period. In the case of RPS stimulation, the refractory period is avoided. Block 5 can also be viewed as a range limiting system, it limits the range of therapy timings that it receives from the feedback controller. Block 3 includes the algorithms that lock out therapy if an abnormal cardiac event such as a premature ventricular contraction or a tachyarrhythmia occurs. Block 1 is the dual-chamber pacing engine of the device, incorporating full dual chamber sensing/pacing capability with the added functionality of atrial coordinated pacing (ACP) with RPS therapies. Finally, block 7 is a defibrillation system including detection of tachyarrhythmic events and application of either shock or pacing therapies such as ATP to terminate these events. The system also includes new rules to increase survivability of long duration episodes of tachycardia or dysfunction normally associated with high-mortality.

While the various components depicted in FIG. 35 preferably are integrated into a single medical device not all such components must be included in any particular medical device. In fact, the components may be distributed between remote devices and coupled wirelessly or otherwise to perform according to the foregoing description. Medical devices employing such components may comprise IMDs, AED or other external medical devices, device programmers, temporary pacing/defibrillation devices and the like.

Figure 36:
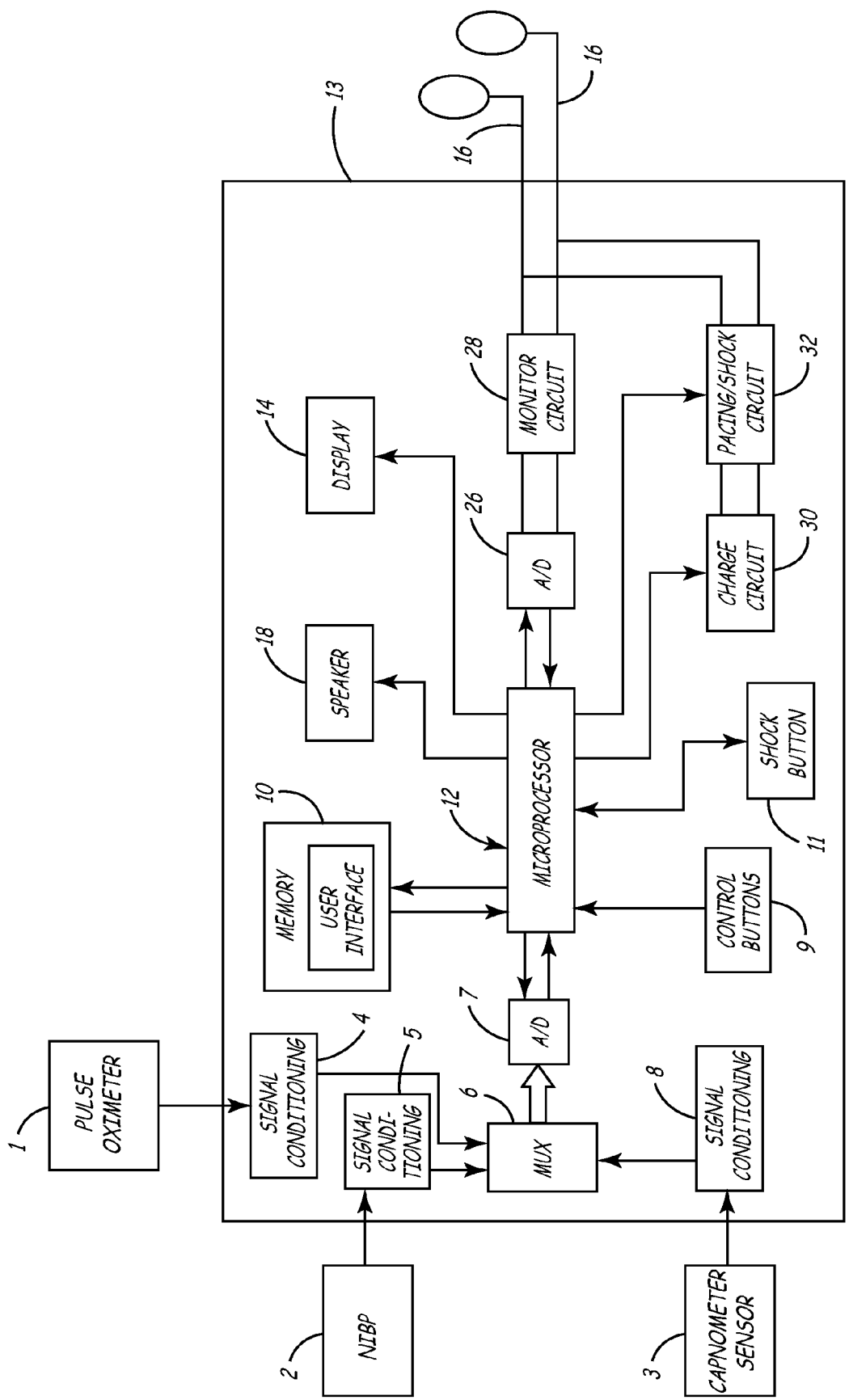
FIG. 36 is a set of traces representing physiologic and therapy activity according to the present invention.

FIG. 36 is a diagram illustrating an embodiment of the present invention embodied into a conventional AED device. In one form of this embodiment, such a conventional AED has a cardiac pacing system adapted for TCP (such as pace/sense circuit 32). While not depicted, the user interface would be reconfigured to display appropriate pacing and sensing indicators and enhanced microprocessor capability to handle TCP.

In another form of this embodiment, a conventional AED is configured for RPS and/or NES therapy delivery according to the present invention. Suitable AED circuitry for delivery of RPS and/or NES therapy may be located within pace/sense circuit 32. While not depicted, the user interface would be reconfigured to display appropriate pacing and sensing indicators and enhanced microprocessor capability to handle RPS and NES therapy. This form of the invention is preferably based almost exclusively upon electrical signals derived from surface electrodes.

In yet form of this embodiment, an AED would beneficially include various physiologic sensors to better assess the degree of cardiac dysfunction and response to delivered therapies (e.g., defibrillation, RPS, NES, TCP and the like). As depicted in FIG. 36 one or more sensors 1,2,3 may be coupled to the AED to assess the need and efficacy of therapy. Examples of such sensors include a pulse oximeter 1, a non-invasive blood pressure sensor 2, a capnometer (i.e., an expired $CO_2$ sensor) 3 and the like. In combination with such sensors signal conditioning circuitry 4,5,8 are preferably coupled to amplify and filter such signals and make them available to the microprocessor and related circuitry of the AED.

One significant advantage of all forms of this embodiment that include RPS results from the fact that conventional AED defibrillation frequently immediately terminates a lethal rhythm but often fails to restore adequate cardiac function. As a result, a victim of sudden cardiac arrest oftentimes rapidly or eventually succumbs to cardiac dysfunction or EMD/PEA. An AED configured to deliver RPS therapy promptly following termination of the tachyarrhythmia beneficially attempts to restore adequate cardiac function. Prompt restoration of cardiac mechanical function is exceptionally critical immediately following termination of such a potentially lethal tachyarrhythmia and is provided by this aspect of the present invention.

The following examples are intended as illustrative and are not intended to be limiting of the scope of the claimed invention.

Example 1

AED Example with Presentation of VF

Despite the increasing availability to quick access defibrillation by the public and quickening response times, the prognosis of a victim of a sudden cardiac arrest surviving to a hospital discharge is low, with many of these victims succumbing to electromechanical dissociation (EMD) or pulseless electrical activity (PEA). Current AED technology is equipped to treat tachyarrhythmias but has no means to treat EMD/PEA.

An AED equipped with the features detailed in this invention would address these scenarios. In an example implementation, the AED would appear identical to the first responder. The responder would place two transthoracic self-adhesive electrodes on the patient and depress a start button on the device. The AED would then obtain a surface ECG from the transthoracic electrodes and apply a VF detection algorithm to the signal. If VF was detected, the AED would apply a defibrillation shock and then apply a re-detection algorithm. If VF stopped or was never present, the device would check to see if the patient was in a bradyarrhythmia or asystole and then would apply pacing therapies through the transthoracic electrodes if needed. Furthermore, upon sensing a sinus rhythm or during a paced rhythm, the device would request for the responder to obtain a pulse from the victim. If a pulse was not detected, the responder would press a button on the AED, which would initiate RPS/NES therapies, delivered through the transthoracic electrodes. The device would periodically request additional pulse checks and would have an abort button clearly labeled, allowing the responder to terminate therapy should the victim regain consciousness.

Alternatively, the AED would be connected to a sensor that made a non-invasive measurement of cardiac function such as a pulse oximeter or a non-invasive blood pressure device such as a inflatable arm cuff. Such a system would not require the responder to make assessments of the victims pulse and would automatically start and stop RPS/NES therapy as needed.

Example 2

ICD Example with Presentation of VT

ICD systems provides patients with greatly improved survivability from episodes of sudden cardiac arrest when compared to patients treated with AED's mainly because there is minimal time to wait between the onset of the arrhythmia and delivery of therapy when the device is implanted and always ready to detect events. However, some patients, especially those with more pronounced HF, may not tolerate well even the shortest of VF episodes and may have depressed cardiac function long after the arrhythmia is terminated. Additionally, circumstances may arise that lengthen the duration of the tachyarrhythmia before the device delivers a therapy. Some tachyarrhythmias pose detection problems for ICD's, which may postpone delivery of therapy. An arrhythmia could also require several shocks to terminate, further prolonging the episode.

During a tachyarrhythmia, the coronary blood flow perfusing the heart can become severely impaired, leading to ischemia and a temporary loss in cardiac contractility referred to as stunning. If the loss in contractility is severe enough to prevent restoration of coronary flow once the arrhythmia is terminated, further ischemia will result, leading to further diminishment of contractility in a downward spiral. A therapy to quickly restore contractility can break this cycle and lead to restoration of sustained cardiac function.

An example of a RPS/NES stimulation therapy would include treating impaired cardiac mechanical function following a tachyarrhythmia. In an example scenario, an ICD equipped with such a therapy would log the duration of any detected tachyarrhythmia. If the duration of the episode exceeded a programmable threshold before being terminated, indicating that the likelihood was high that cardiac mechanical function was severely impaired, the device would initiate a NES/RPS therapy for a fixed duration following the episode to provide a quick boost in hemodynamics to hasten re-perfusion of the heart and allow a more complete recovery from the tachyarrhythmia. Alternatively, an RV pressure sensor could detect RV pulse pressure following the episode and compare it to a baseline value measured and stored before the episode was detected. Should the RV pulse pressure fall shy of the baseline value for too great of a time following the tachyarrhythmia, indicating prolonged periods of depressed cardiac mechanical function, the ICD would initiate RPS/NES therapies and then terminate the therapies after the RV pressure reached some percentage of the baseline measurement, indicating that the cardiac function was restored.

Example 3

HF Example with Presentation of Acute Decompensation

Advanced stage HF patients experience sudden worsening of heart failure associated symptoms which require hospitalization. The transition from chronic compensated HF to acute decompensated HF may result from a number of factors including dietary indiscretion, progress of HF disease, and acute myocardial infarction. When severe, symptoms may progress in a few hours to a stage where these patients need to be admitted to a critical care hospital bed, monitored by physiologic sensors, and treated with a variety of drugs including intravenous inotropes. A patient experiencing such a decompensation commonly exhibits low cardiac output at rest, poor contractile function and low dP/dt max, slow relaxation and high tau, elevated diastolic ventricular pressures, and reduced ventricular developed pressures.

Cardiac resynchronization therapy delivered by an implanted device is an important adjunct to good medical therapy. Such a resynchronization device possesses electrodes and circuitry suited to deliver NES and/or RPS stimulation therapy. Implantable monitoring technology to continuously monitor cardiac performance using RV pressure is undergoing clinical trials. In this scenario, the implantable device is equipped to provide stimulation therapies and monitor hemodynamic function as taught by this invention.

Upon detection of a rise of RV diastolic pressure and decreased contractility assessed by dP/dt from a mean value established over the past 2-4 weeks, RPS therapy may be initiated with a single 2.0 V, 0.5 ms ventricular pulse delivered 260 ms after a Vsense event from a RV apex bipolar lead. At this point the patient may only experience a mild worsening of HF symptoms.

In this scenario, the response to this therapy is an almost immediate doubling of dP/dt max, increased stroke volume and ejection fraction, increased cardiac output, and reduced heart rate. Over the course of a few hours, the improved hemodynamics allow the kidneys to remove excess salt and water and RV diastolic pressure falls back to baseline levels. Stimulation therapy is painless and automatically started and discontinued without being noticed by the patient. Interrogation of the implanted device's memory reveals the episode described above and is credited with preventing hospitalization or an emergency department visit.

Example 4

SVT Example with Poor Toleration of High Rate

Supraventricular tachycardias that result in rapid ventricular rates may be poorly tolerated, particularly in patients with a history of heart failure. In this scenario the patient experiences first symptoms of dizziness and palpitations (a sensation of a fluttering within the chest). Upon evaluation by emergency medical personnel, the heart rate is found to be 220 bpm. Over the next few minutes, the patient's blood pressure drops, and the patient becomes pale, sweaty and confused. An AED device instrumented with NES and RPS therapies as described in this invention is attached to the patient by a pair of adhesive pad electrodes.

The fast but narrow ECG complexes allow the device to diagnose a serious SVT and the operator is presented with the option of a trial of RPS stimulation or cardioversion. After administering a sedative/analgesic, a 5 minute trial of RPS stimulation is begun by delivering 20 ms pulses of 60 mA timed 250 ms after surface ECG ventricular sense events. Vital signs, evaluated by the emergency personnel document that heart rate drops from 220 to 110 bpm and that blood pressure increases from 90/50 to 120/60. The patient becomes more lucid and notably more pink. Before the 2 minute trial is completed, the rhythm spontaneously converts to a sinus rhythm at 120 bpm. The AED recognizes this and ends its stimulation therapy immediately.

A patient with a history of HF may not tolerate a tachyarrhythmia well for more than a few minutes. If the rate is high enough, patients often loose consciousness and their rhythms deteriorate into VF. Despite prompt and good care, defibrillation after a prolonged several minutes of cardiac ischemia may result in EMD/PEA or asystole and death. This patient was indicated for urgent pharmacologic or electrical cardioversion shock therapy and avoided both.

While the foregoing has been described as employing RPS alone (with incidental NES therapy due to the location of the surface electrode and magnitude of the stimulation), it may be desirable to intentionally invoke NES alone or in combination with RPS therapy. This may be advantageously employed by using one or more dedicated electrodes.

The above-described methods and apparatus are believed to be of particular benefit for patient's suffering heart failure including cardiac dysfunction, chronic HF, and the like and all variants as described herein and including those known to those of skill in the art to which the invention is directed. It will understood that the present invention offers the possibility of monitoring and therapy of a wide variety of acute and chronic cardiac dysfunctions. The current invention provides a system and method for delivering therapy for cardiac hemodynamic dysfunction, which without limitation, may include one of the following features:

Therapy for cardiac dysfunction that might otherwise require inotropic drugs such as dobutamine, calcium, or milrinone;

Therapy for cardiac dysfunction that might otherwise require mechanical aids such as intra-aortic balloon pumps, cardiac compression devices, or LV assist device pumps;

An implantable or external device that continuously monitors the patient, automatically administering therapy when physiologic sensors indicate need or the patient experiences symptoms;

Treatment for cardiac dysfunction as a result of drug overdose or hypothermia;

Combined with negative inotrope drug treatments such as beta blockers to improve patient tolerance of these treatments;

Therapy for post ischemic cardiac dysfunction or stunning such as following coronary vessel occlusion, thrombolytic drugs, angioplasty, or cardiac bypass surgery;

Support for the dysfunction that is associated with coming off cardiac bypass and the use of cardioplegia;

Therapy for rapid and poorly tolerated supra-ventricular tachycardias (SVT) by regularizing 2:1 AV block, lowering mechanical heart rate and improving mechanical function, and may facilitate arrhythmia termination;

Management of dysfunction following tachycardic events including AT, AF, SVT, VT, or VF including elective cardioversion and urgent defibrillation and resuscitation;

Severe bouts of heart failure, worsening to cardiogenic shock, electromechanical dissociation (EMD) or pulseless electrical activity (PEA)

Acute deterioration of cardiac function associated with hypoxia or metabolic disorders;

Intermittent therapy for HF such as prior or during exertion or for worsening symptoms;

Continuous therapy for HF to modify heart rate, improve filling and mechanical efficiency, and facilitate reverse remodeling and other recovery processes;

Scheduled therapy for HF including use for a specified interval of time at a particular time of day or scheduled delivery every N cardiac cycles;

Atrial RPS therapy to increase atrial contractility, facilitate better ventricular filling, and AV synchrony; and/or Reducing AF burden as a result of reduced atrial loading and better ventricular function during therapy.

Consequently, the expression "heart failure" as used in above and in the following claims shall be understood to embrace each of the foregoing and conditions related thereto. All patents and other publications identified above are incorporated herein by reference.

While the present invention has been illustrated and described with particularity in terms of preferred embodiments, it should be understood that no limitation of the scope of the invention is intended thereby. The scope of the invention is defined only by the claims appended hereto. It should also be understood that variations of the particular embodiments described herein incorporating the principles of the present invention will occur to those of ordinary skill in the art and yet be within the scope of the appended claims.

The invention claimed is:

1. A method of cardiac pacing, comprising:
sensing depolarizations of an atrium and a ventricle of a patient's heart using an implantable cardiac pacemaker;
delivering atrial pacing pulses to the atrium of the patient's heart using the pacemaker;
at a selected time following a conducted depolarization of the atrium resulting in a sensed ventricular depolarization, delivering an atrial coupled (ACP) atrial pacing pulse;
wherein the selected time is selected such that an atrial paced beat resulting from the delivered ACP atrial pacing pulse is not conducted to the ventricle because the ventricle is in a refractory state;
examining the sensed depolarizations for an occurrence of an unscheduled depolarization; and
responsive to occurrence of one unscheduled depolarization, ceasing delivery of the ACP atrial pacing pulses,
wherein ceasing delivery of the ACP atrial pacing pulses further comprises withholding delivery and not initiating delivery of the ACP atrial pacing pulses in the event that the unscheduled depolarization begins an accumulating tachycardia evidence counter of an ongoing tachycardia episode or until such time as either the evidence counter reaches a preset threshold and a tachycardia episode is declared or the evidence counter is reset to a nominal or null value.

2. A method according to claim 1 wherein said unscheduled depolarization comprises a premature atrial contraction or a premature ventricular contraction.

3. A method according to claim 1, wherein ceasing delivery of the ACP atrial pacing pulses further comprises one of:
withholding delivery and not initiating delivery of the ACP atrial pacing pulses for at least one subsequent cardiac cycle.

4. A method according to claim 1, wherein ceasing delivery of the ACP atrial pacing pulses further comprises one of:
withholding delivery and not initiating delivery of the ACP pacing pulses in the event that the unscheduled depolarization comprises a depolarization indicative of a tachycardia episode.

5. A method according to claim 1 wherein said unscheduled depolarization comprises a premature ventricular contraction.

6. A method of cardiac pacing, comprising:
sensing depolarizations of an atrium and a ventricle of a patient's heart using an implantable cardiac pacemaker;
delivering atrial pacing pulses to the atrium of the patient's heart using the pacemaker; and at a selected time following a conducted depolarization of the atrium resulting in a sensed ventricular depolarization, delivering an atrial coupled (ACP) atrial pacing pulse;

wherein the selected time is selected such that an atrial paced beat resulting from the delivered ACP atrial pacing pulse is not conducted to the ventricle because the ventricle is in a refractory state;

wherein the conducted atrial depolarization comprises a sensed atrial depolarization;

examining the sensed depolarizations for an occurrence of an unscheduled depolarization; and responsive to occurrence of one unscheduled depolarization, ceasing delivery of the ACP atrial pacing pulses, wherein ceasing delivery of the ACP atrial pacing pulses further comprises withholding delivery and not initiating delivery of the ACP atrial pacing pulses in the event that the unscheduled depolarization begins an accumulating tachycardia evidence counter of an ongoing tachycardia episode or until such time as either the evidence counter reaches a preset threshold and a tachycardia episode is declared or the evidence counter is reset to a nominal or null value.

7. A method according to claim 6 wherein said unscheduled depolarization comprises a premature atrial contraction or a premature ventricular contraction.

8. A method according to claim 6, wherein ceasing delivery of the ACP atrial pacing pulses further comprises one of:
withholding delivery and not initiating delivery of the ACP atrial pacing pulses for at least one subsequent cardiac cycle.

9. A method according to claim 6, wherein ceasing delivery of the ACP pacing pulses further comprises one of:
withholding delivery and not initiating delivery of the ACP pacing pulses in the event that the unscheduled depolarization depolarization comprises a depolarization indicative of a tachycardia episode.

10. A method according to claim 6 wherein said unscheduled depolarization comprises a premature ventricular contraction.

11. An implantable cardiac pacemaker, comprising:
means for sensing depolarizations of an atrium and a ventricle of a patient's heart;
means for delivering atrial pacing pulses to the atrium of the patient's heart; and
means for, at a selected time following a conducted depolarization of the atrium resulting in a sensed ventricular depolarization, delivering an ACP atrial pacing pulse;
wherein the selected time is selected such that an atrial paced beat resulting from the delivered ACP atrial pacing pulse is not conducted to the ventricle because the ventricle is in a refractory state;
means for examining the sensed depolarizations for an occurrence of an unscheduled depolarization; and
means for, responsive to occurrence of one unscheduled depolarization, ceasing delivery of the ACP atrial pacing pulses,
wherein ceasing delivery of the ACP atrial pacing pulses further comprises withholding delivery and not initiating delivery of the ACP atrial pacing pulses in the event that the unscheduled depolarization begins an accumulating tachycardia evidence counter of an ongoing tachycardia episode or until such time as either the evidence counter reaches a preset threshold and a tachycardia episode is declared or the evidence counter is reset to a nominal or null value.

12. An apparatus according to claim 11 wherein said unscheduled depolarization comprises a premature atrial contraction or a premature ventricular contraction.

13. An apparatus according to claim 11, wherein ceasing delivery of the ACP atrial pacing pulses further comprises one of:
withholding delivery and not initiating delivery of the ACP atrial pacing pulses for at least one subsequent cardiac cycle.

14. An apparatus according to claim 11, wherein ceasing delivery of the ACP atrial pacing pulse further comprises one of:
withholding delivery and not initiating delivery of the ACP pacing pulses in the event that the unscheduled depolarization comprises a depolarization indicative of a tachycardia episode.

15. An apparatus according to claim 11 wherein said unscheduled depolarization comprises a premature ventricular contraction.

16. An implantable cardiac pacemaker, comprising:
means for sensing depolarizations of an atrium and a ventricle of a patient's heart;
means for delivering atrial pacing pulses to the atrium of the patient's heart; and
means for, at a selected time following a conducted depolarization of the atrium resulting in a sensed ventricular depolarization, delivering an ACP atrial pacing pulse;
wherein the selected time is selected such that an atrial paced beat resulting from the delivered ACP atrial pacing pulse is not conducted to the ventricle because the ventricle is in a refractory state;
wherein the conducted atrial depolarization comprises a sensed atrial depolarization;
means for examining the sensed depolarizations for an occurrence of an unscheduled depolarization; and
means for, responsive to occurrence of one unscheduled depolarization, ceasing delivery of the ACP atrial pacing pulses,
wherein ceasing delivery of the ACP atrial pacing pulses further comprises withholding delivery and not initiating delivery of the ACP atrial pacing pulses in the event that the unscheduled depolarization begins an accumulating tachycardia evidence counter of an ongoing tachycardia episode or until such time as either the evidence counter reaches a preset threshold and a tachycardia episode is declared or the evidence counter is reset to a nominal or null value.

17. An apparatus according to claim 16 wherein said unscheduled depolarization comprises a premature atrial contraction or a premature ventricular contraction.

18. An apparatus according to claim 16, wherein ceasing delivery of the ACP atrial pacing pulse further comprises one of:
withholding delivery and not initiating delivery of the ACP atrial pacing pulses for at least one subsequent cardiac cycle.

19. An apparatus according to claim 16, wherein ceasing delivery of the ACP atrial pacing pulse further comprises one of:
withholding delivery and not initiating delivery of the ACP pacing pulses in the event that the unscheduled depolarization comprises a depolarization indicative of a tachycardia episode.

20. An apparatus according to claim 16 wherein said unscheduled depolarization comprises a premature ventricular contraction.

* * * * *